US009540621B2

(12) United States Patent
Quinn et al.

(10) Patent No.: US 9,540,621 B2
(45) Date of Patent: *Jan. 10, 2017

(54) NPP1 FUSION PROTEINS

(71) Applicant: Synageva BioPharma Corp., Lexington, MA (US)

(72) Inventors: Anthony Quinn, Chestnut Hill, MA (US); Alex J. Harvey, Athens, GA (US); Zhinan Xia, Wellesley, MA (US)

(73) Assignee: ALEXION PHARMACEUTICALS, INC., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/449,364

(22) Filed: Aug. 1, 2014

(65) Prior Publication Data

US 2014/0377859 A1     Dec. 25, 2014

Related U.S. Application Data

(63) Continuation of application No. 13/583,973, filed as application No. PCT/US2011/028233 on Mar. 11, 2011, now Pat. No. 8,846,603.

(60) Provisional application No. 61/340,066, filed on Mar. 12, 2010.

(51) Int. Cl.
| | |
|---|---|
| *C12N 9/96* | (2006.01) |
| *C12N 15/00* | (2006.01) |
| *C12N 15/52* | (2006.01) |
| *C12N 15/63* | (2006.01) |
| *C12N 15/85* | (2006.01) |
| *C12N 9/16* | (2006.01) |
| *C12N 9/00* | (2006.01) |
| *C12N 9/22* | (2006.01) |

(52) U.S. Cl.
CPC . *C12N 9/16* (2013.01); *C12N 9/00* (2013.01); *C12N 9/22* (2013.01); *C12N 9/96* (2013.01); *C07K 2319/00* (2013.01); *C07K 2319/01* (2013.01); *C07K 2319/02* (2013.01); *C07K 2319/33* (2013.01); *C12Y 301/04001* (2013.01); *Y10S 530/827* (2013.01)

(58) Field of Classification Search
CPC ............ C07K 2319/33; C07K 2319/02; C07K 2319/01; C07K 2319/00; C12N 9/96; C12N 9/00; C12Y 301/04001
See application file for complete search history.

(56) References Cited

U.S. PATENT DOCUMENTS

| | | |
|---|---|---|
| 6,455,495 B1 | 9/2002 | Orgel et al. |
| 7,960,529 B2 | 6/2011 | Crine et al. |
| 8,846,603 B2 | 9/2014 | Quinn et al. |
| 2009/0180989 A1 | 7/2009 | Harvey |
| 2009/0298167 A1 | 12/2009 | Bloom et al. |
| 2014/0154774 A1 | 6/2014 | Quinn et al. |

FOREIGN PATENT DOCUMENTS

| | | |
|---|---|---|
| DE | 20121960 | 2/2004 |
| EP | 2368999 B1 | 9/2011 |
| WO | 2006059113 | 6/2006 |
| WO | WO/2006/059113 | * 6/2006 ............ C07K 14/33 |
| WO | WO2011/113027 | 9/2011 |

OTHER PUBLICATIONS

Goding et al., Biochimica et Biophysica Acta (2003) 1638, 1-19.*
Flanagan et al., "Soluble Fc Fusion Proteins for Biomedical Research," in Monoclonal Antibodies, Methods and Protocols, ed. By Albitar, Methods in Molecular Biology, (2007) 378, 33-52.*
Belli et al., Eur. J. Biochem. (1993) 217, 421-428.*
Belli, Sabina I., et al., Identification and Characterization of a Soluble Form of the Plasma Cell Membrane Glycoprotein PC-1 (5'-Nucleotide Phosphodiesterase), Eur. J. Biochem, 217, 421-428, Feb. 1993.
Rutsch et al., "Mutations in ENPP1 are Associated with 'Idiopathic' Infantile Arterial Calcification," Nature Genetics, 34:(4)379-381 (2003).
Nishioka et al., "Enhancement of Drug Delivery to Bone: Characterization of Human Tissue-Nonspecific Alkaline Phosphatase Tagged with an Acidic Oligopeptide," Mol. Genet, Metab. 88(3):244-255 (2006).
Johnson et al., "Linked Deficiencies in Extracellular PP(i) and Osteopontin Mediate Pathologic Calcification Associated with Defective PC-1 and ANK Expression," Journal of Bone and Mineral Research. 18(6):994-1004.(2003).
Millan et al., "Enzyme Replacement Therapy for Murine Hypophosphatasia," Journal of Bone and Mineral Research, 23(6):777-787 (2008).
Supplementary Search Report dated Jul. 31, 2013 from European Application No. 11754231.6.
Goding et al., "Physiological and Pathophysiological Functions of the Ecto-Nucleotide Pyrophosphatases/Phosphodiesterase Family," Biochimica et Biophysica Acta, 1638:1-19 (2003).
Flanagan et al., "Soluble Fc Fusion Proteins for Biomedical Research," in Monoclonal Antibodies, Methods and Protocols, et. by Albitar, Methods in Molecular Biology, (2007) vol. 378, 33-52.
Wang et al., "Pharmacokinetic and Biodistribution Studies of a Bone-Targeting Drug Delivery System Based on N-(2-Hydroxypropyl) Methacrylamide Copolymers," Molecular Pharmaceutics, 3(6):717-725 (2006).
Guan et al., "Peptide-Targeted Polyglutamic Acid Doxorubicin Conjugates for the Treatment of αvβ6-Positive Cancers," Bioconjugate Chem., 19:1813-1821 (2008).
Gijsbers et al., "Functional Characterization of the Non-Catalytic Ectodomains of the Nucleotide Pyrophosphatase/Phosphodiesterase NPP1," Biochem. J. 371:321-330 (2003).

(Continued)

*Primary Examiner* — Karlheinz R Skowronek
*Assistant Examiner* — Catherine Mader
(74) *Attorney, Agent, or Firm* — McDermott Will & Emery LLP

(57) ABSTRACT

The present invention provides a novel fusion polypeptide containing a catalytic portion of NPP1 fused to a targeting moiety, nucleic acids encoding the fusion polypeptide, a vector containing the nucleic acid integrated thereinto, a host cell transformed with the vector and pharmaceutical compositions comprising the fusion polypeptide.

16 Claims, 20 Drawing Sheets

(56) References Cited

OTHER PUBLICATIONS

Schetter et al., "Nucleoporins NPP-1, NPP-3, NPP-4, NPP11 and NPP-13 are Required for Proper Spindle Orientation in C. Elegans," Developmental Biology, 289:360-371 (2005).

Gijsbers et al., "The Hydrolysis of Lysophospholipids and Nucleotides by Autotaxin (NPP2) Involves a Single Catalytic Site," FEBS Letters, 538:60-64 (2003).

Johnson et al., "Chondrogenesis Mediated by PPi Depletion Promotes Spontaneous Aortic Calcificiation in NNP1-/1Mice," Arterioscler Thromb Vasc Biology, 25:686-691 (2005).

Stefan et al., "NPP-type ectophosphodiesterases: Unity in Diversity" Trend in Biochemical Sciences 30(10);542:550 (2005).

International Search Report dated Nov. 24, 2011 from Corresponding PCT Application No. PCT/US2011/028233.

International Preliminary Report on Patentability dated Sep. 18, 2012 from Corresponding PCT Application No. PCT/US2011/028233.

International Search Report dated Apr. 26. 2012 from PCT Application No. PCT/US2011/051858.

International Preliminary Report on Patentability dated Sep. 17, 2013 from PCT Application No. PCT/US2011/051858.

Lomashvili, et al., "Phosphate-Induced Vascular Calcification: Role of Pyrophosphate and Osteopontin," Journal of American Society of Nephrology, 1392-1401, Mar. 4, 2004.

O'Neill, et al., "Treatment with pyrophosphate inhibits uremic vascular calcification," International Society of Nephrology, 512-517, Mar. 2011.

Supplementary European Search Report from EP 11 86 1101, Jun. 25, 2014.

NCBI Accession No. NM_006208, Mar. 2001.

Goding et al., "Ecto-phosphodiesterase/pyrophosphatase of Lymphocytes and Non-lymphoid Cells: Structure and Function of the PC-1 Family," Immunological Reviews, 161:11-26 (1998).

Murphy et al., "Synthesis and in Vitro Hydroxyapatite Binding of Peptides Conjugated to Calcium-Binding Moieties," Biomacromolecules, 8:2237-2243 (2007).

Zhang et al., "Investigation of the Role of ENPP1 and TNAP Genes in Chondrocalcinosis," Rheumatology, 46:586-589 (2007).

Huang, "Receptor-Fc Fusion Therapeutics, traps, and Mimetibody Technology," Current Opinion in Biotechnology, 20:692-699 (2009).

Schmidt, "Fusion Proteins as Biopharmaceuticals—Applications and Challenges," Current Opinion in Drug Discovery & Development, 12:1-12 (2009).

Beck et al., "Therapeutic Fc-fusion Proteins and Peptides as Successful Alternatives to Antibodies," 3:5, 415-416 (2011).

Chamow, S. M. et al., "Immunoadhesins: Principles and Applications," Trends Biotechnol., 14(2); 52-60 (1996).

van Meeteren et al, Inhibition of Autotaxin by Lysophosphatidic Acid and Sphingosine 1-Phosphate, J. Biol. Chem., 280:21155-61 (2005).

\* cited by examiner

NPP1 (wild-type)

MERDGCAGGGSRGGEGGRAPREGPAGNGRDRGRSHAAEAPGDPQAAASLLAPMDVGEEPLEKAARA
RTAKDPNTYKVLSLVLSVCVLTTILGCIFGLKPSCAKEVKSCKGRCFERTFGNCRCDAACVELGNCCLDYQET
CIEPEHIWTCNKFRCGEKRLTRSLCACSDDCKDKGDCCINYSSVCQGEKSWVEEPCESINEPQCPAGFETP
PTLLFSLDGFRAEYLHTWGGLLPVISKLKKCGTYTKNMRPVYPTKTFPNHYSIVTGLYPESHGIIDNKMYDP
KMNASFSLKSKEKFNPEWYKGEPIWVTAKYQGLKSGTFFWPGSDVEINGIFPDIYKMYNGSVPFEERILAV
LQWLQLPKDERPHFYTLYLEEPDSSGHSYGPVSSEVIKALQRVDGMVGMLMDGLKELNLHRCLNLILISD
HGMEQGSCKKYIYLNKYLGDVKNIKVIYGPAARLRPSDVPDKYYSFNYEGIARNLSCREPNQHFKPYLKHF
LPKRLHFAKSDRIEPLTFYLDPQWQLALNPSERKYCGSGFHGSDNVFSNMQALFVGYGPGFKHGIEADTF
ENIEVYNLMCDLLNLTPAPNNGTHGSLNHLLKNPVYTPKHPKEVHPLVQCPFTRNPRDNLGCSCNPSILPI
EDFQTQFNLTVAEEKIIKHETLPYGRPRVLQKENTICLLSQHQFMSGYSQDILMPLWTSYTVDRNDSFSTE
DFSNCLYQDFRIPLSPVHKCSFYKNNTKVSYGFLSPPQLNKNSSGIYSEALLTTNIVPMYQSFQVIWRYFHD
TLLRKYAEERNGVNVVSGPVFDFDYDGRCDSLENLRQKRRVIRNQEILIPTHFFIVLTSCKDTSQTPLHCENL
DTLAFILPHRTDNSESCVHGKHDSSWVEELLMLHRARITDVEHITGLSFYQQRKEPVSDILKLKTHLPTFSQ
ED  (SEQ ID NO:1)

Fig. 1 sssNPP1 (NPP1 catalytic domain with no TAG)

AGFETPPTLLFSLDGFRAEYLHTWGGLLPVISKLKKCGTYTKNMRPVYPTKTFPNHYSIVTGLYPESHGIIDN
KMYDPKMNASFSLKSKEKFNPEWYKGEPIWVTAKYQGLKSGTFFWPGSDVEINGIFPDIYKMYNGSVPF
EERILAVLQWLQLPKDERPHFYTLYLEEPDSSGHSYGPVSSEVIKALQRVDGMVGMLMDGLKELNLHRCL
NLILISDHGMEQGSCKKYIYLNKYLGDVKNIKVIYGPAARLRPSDVPDKYYSFNYEGIARNLSCREPNQHFK
PYLKHFLPKRLHFAKSDRIEPLTFYLDPQWQLALNPSERKYCGSGFHGSDNVFSNMQALFVGYGPGFKHG
IEADTFENIEVYNLMCDLLNLTPAPNNGTHGSL (SEQ ID NO:2)

Fig. 2

TAGsssNPP1 (N-terminus D8)

IGVLLTQRTLLSLVLALLFPSMASMDDDDDDDDAGFETPPTLLFSLDGFRAEYLHTWGGLLPVISKLKKCG
TYTKNMRPVYPTKTFPNHYSIVTGLYPESHGIIDNKMYDPKMNASFSLKSKEKFNPEWYKGEPIWVTAKY
QGLKSGTFFWPGSDVEINGIFPDIYKMYNGSVPFEERILAVLQWLQLPKDERPHFYTLYLEEPDSSGHSYG
PVSSEVIKALQRVDGMVGMLMDGLKELNLHRCLNLILISDHGMEQGSCKKYIYLNKYLGDVKNIKVIYGPA
ARLRPSDVPDKYYSFNYEGIARNLSCREPNQHFKPYLKHFLPKRLHFAKSDRIEPLTFYLDPQWQLALNPSE
RKYCGSGFHGSDNVFSNMQALFVGYGPGFKHGIEADTFENIEVYNLMCDLLNLTPAPNNGTHGSL (SEQ
ID NO:3)

Fig. 3

TAGsssNPP1 (C-terminus D10)

IGVLLTQRTLLSLVLALLFPSMASMAGFETPPTLLFSLDGFRAEYLHTWGGLLPVISKLKKCGTYTKNMRPV
YPTKTFPNHYSIVTGLYPESHGIIDNKMYDPKMNASFSLKSKEKFNPEWYKGEPIWVTAKYQGLKSGTFF
WPGSDVEINGIFPDIYKMYNGSVPFEERILAVLQWLQLPKDERPHFYTLYLEEPDSSGHSYGPVSSEVIKAL
QRVDGMVGMLMDGLKELNLHRCLNLILISDHGMEQGSCKKYIYLNKYLGDVKNIKVIYGPAARLRPSDVP
DKYYSFNYEGIARNLSCREPNQHFKPYLKHFLPKRLHFAKSDRIEPLTFYLDPQWQLALNPSERKYCGSGFH
GSDNVFSNMQALFVGYGPGFKHGIEADTFENIEVYNLMCDLLNLTPAPNNGTHGSLDDDDDDDDDD
(SEQ ID NO:4)

Fig. 4

TAGssNPP1 (N-terminus D8)

ATGGGTGTACTGCTCACACAGAGGACGCTGCTCAGTCTGGTCCTTGCACTCCTGTTTCCAAGCATGGCGAGCA
TGGATGACGATGATGACGACGATGACGCAGGGTTTGAAACGCCTCCTACACTCTTGTTTTCTTTGGATGGATT
CAGGGCAGAATATTTGCACACTTGGGGTGGACTTCTTCCTGTTATTAGCAAACTCAAAAAATGTGGAACATAT
ACTAAAAACATGAGACCGGTGTATCCAACAAAAACTTTCCCCAATCACTACAGCATTGTCACCGGATTGTATCC
AGAATCTCATGGCATAATCGACAATAAGATGTATGATCCCAAAATGAATGCTTCCTTTTCACTTAAAAGTAAAG
AGAAATTTAATCCGGAGTGGTACAAAGGAGAACCAATTTGGGTCACAGCTAAGTATCAAGGCCTCAAGTCTG
GCACATTTTTCTGGCCAGGATCAGATGTGGAAATTAACGGAATTTTCCCAGACATCTATAAAATGTATAATGGT
TCAGTGCCATTTGAAGAAGGATTTTGGCTGTTCTTCAGTGGCTGCAGCTTCCAAAAGATGAAAGACCACACT
TTTACACTTTGTATTTGGAAGAACCAGATTCTTCAGGTCATTCATATGGACCAGTCAGCAGTGAAGTCATCAAA
GCCTTGCAGAGGGTTGATGGTATGGTTGGTATGCTGATGGATGGTCTGAAAGAGCTGAACTTGCACAGATGC
CTGAACCTCATCCTTATTTCAGATCATGGCATGGAACAAGGCAGTTGTAAGAAATACATATATCTGAATAAGTA
TTTGGGGGATGTTAAAAATATTAAAGTTATCTATGGACCTGCAGCTCGATTGAGACCCTCTGATGTCCCAGATA
AATACTATTCATTTAACTATGAAGGCATTGCCCGAAATCTTTCTTGCCGGGAACCAAACCAGCACTTCAAACCT
TATCTGAAACATTTCTTGCCTAAGCGTTTGCACTTTGCTAAGAGTGATAGAATTGAGCCCTTGACATTCTATTTG
GACCCTCAGTGGCAACTTGCATTGAATCCCTCAGAAAGGAAATATTGTGGAAGTGGATTTCATGGCTCTGACA
ATGTGTTTTCAAATATGCAAGCCCTCTTTGTTGGCTATGGACCTGGATTCAAGCATGGCATTGAGGCTGACACC
TTTGAAAACATTGAAGTCTATAACTTGATGTGTGATTTGCTGAATTTGACACCGGCTCCTAATAACGGAACTCA
TGGAAGTCTTAACCACCTTCTGAAGAATCCTGTTTATACGCCAAAGCATCCCAAAGAAGTGCACCCCCTGGTGC
AGTGCCCCTTCACAAGAAACCCCAGAGATAACCTTGGCTGCTCATGTAACCCTTCCATTTTGCCGATTGAGGAT
TTTCAAACACAGTTCAATCTGACCGTGGCAGAAGAGAAGATTATTAAGCATGAAACTTTGCCCTATGGAAGAC
CTAGAGTTCTCCAGAAGGAAAACACCATCTGTCTTCTTTCCCAGCACCAGTTTATGAGTGGATACAGCCAAGAC
ATCTTGATGCCCCTTTGGACATCCTATACCGTGGACAGAAATGACAGTTTCTCTACGGAAGACTTCTCCAACTG
TCTGTACCAGGACTTTAGAATTCCTCTTAGTCCTGTCCATAAATGTTCATTTTATAAAAATAACACCAAAGTGAG
TTACGGGTTCCTCTCCCCACCACAACTGAATAAGAATTCAAGTGGAATATATTCTGAAGCCTTGCTTACTACAA
ATATAGTGCCAATGTACCAGAGTTTTCAAGTTATATGGCGCTACTTTCATGACACCCTCTTGCGAAAGTATGCA
GAAGAAAGAAATGGTGTCAATGTCGTCAGTGGTCCTGTGTTTGACTTTGATTATGATGGACGTTGTGATTCCT
TGGAGAATTTGAGGCAAAAAGAAGAGTCATCCGTAACCAAGAAATTTTGATTCCAACTCATTTCTTCATTGTG
CTGACAAGCTGTAAAGATACATCTCAGACGCCTTTGCACTGTGAAAACCTGGACACCTTGGCTTTCATTTTGCC
TCACAGGACTGATAACAGCGAGAGCTGTGTGCATGGGAAGCATGACTCCTCATGGGTTGAAGAATTGTTGAT
GTTGCACAGAGCACGGATCACAGACGTCGAGCACATCACTGGACTCAGCTTTTATCAACAAAGAAAAGAGCC
AGTTTCAGACATTTTGAAGTTGAAAACACATTTGCCAACCTTTAGCCAAGAAGATTGA (SEQ ID NO:5)

Fig. 5

TAGssNPP1 (N-terminus D8; signal peptide sequence underlined and the targeting moiety in bold)

<u>IGVLLTQRTLLSLVLALLFPSMASM</u>DDDDDDDDAGFETPPTLLFSLDGFRAEYLHTWGGLLPVISKLKKCG
TYTKNMRPVYPTKTFPNHYSIVTGLYPESHGIIDNKMYDPKMNASFSLKSKEKFNPEWYKGEPIWVTAKY
QGLKSGTFFWPGSDVEINGIFPDIYKMYNGSVPFEERILAVLQWLQLPKDERPHFYTLYLEEPDSSGHSYG
PVSSEVIKALQRVDGMVGMLMDGLKELNLHRCLNLILISDHGMEQGSCKKYIYLNKYLGDVKNIKVIYGP
AARLRPSDVPDKYYSFNYEGIARNLSCREPNQHFKPYLKHFLPKRLHFAKSDRIEPLTFYLDPQWQLALNP
SERKYCGSGFHGSDNVFSNMQALFVGYGPGFKHGIEADTFENIEVYNLMCDLLNLTPAPNNGTHGSLN
HLLKNPVYTPKHPKEVHPLVQCPFTRNPRDNLGCSCNPSILPIEDFQTQFNLTVAEEKIIKHETLPYGRPRV
LQKENTICLLSQHQFMSGYSQDILMPLWTSYTVDRNDSFSTEDFSNCLYQDFRIPLSPVHKCSFYKNNTK
VSYGFLSPPQLNKNSSGIYSEALLTTNIVPMYQSFQVIWRYFHDTLLRKYAEERNGVNVVSGPVFDFDYD
GRCDSLENLRQKRRVIRNQEILIPTHFFIVLTSCKDTSQTPLHCENLDTLAFILPHRTDNSESCVHGKHDSS
WVEELLMLHRARITDVEHITGLSFYQQRKEPVSDILKLKTHLPTFSQED  (SEQ ID NO:6)

Fig. 6 ssNPP1 (2238bp)

ATGGGTGTACTGCTCACACAGAGGACGCTGCTCAGTCTGGTCCTTGCACTCCTGTTTCCAAGCATGGCGAGCA
TGGCAGGGTTTGAAACGCCTCCTACACTCTTGTTTTCTTTGGATGGATTCAGGGCAGAATATTTGCACACTTGG
GGTGGACTTCTTCCTGTTATTAGCAAACTCAAAAAATGTGGAACATATACTAAAAACATGAGACCGGTGTATC
CAACAAAAACTTTCCCCAATCACTACAGCATTGTCACCGGATTGTATCCAGAATCTCATGGCATAATCGACAAT
AAGATGTATGATCCCAAAATGAATGCTTCCTTTTCACTTAAAAGTAAAGAGAAATTTAATCCGGAGTGGTACA
AAGGAGAACCAATTTGGGTCACAGCTAAGTATCAAGGCCTCAAGTCTGGCACATTTTCTGGCCAGGATCAGA
TGTGGAAATTAACGGAATTTTCCCAGACATCTATAAAATGTATAATGGTTCAGTGCCATTTGAAGAAAGGATTT
TGGCTGTTCTTCAGTGGCTGCAGCTTCCAAAAGATGAAAGACCACACTTTTACACTTTGTATTTGGAAGAACCA
GATTCTTCAGGTCATTCATATGGACCAGTCAGCAGTGAAGTCATCAAAGCCTTGCAGAGGGTTGATGGTATGG
TTGGTATGCTGATGGATGGTCTGAAAGAGCTGAACTTGCACAGATGCCTGAACCTCATCCTTATTTCAGATCAT
GGCATGGAACAAGGCAGTTGTAAGAAATACATATATCTGAATAAGTATTTGGGGGATGTTAAAAATATTAAA
GTTATCTATGGACCTGCAGCTCGATTGAGACCCTCTGATGTCCCAGATAAATACTATTCATTTAACTATGAAGG
CATTGCCCGAAATCTTTCTTGCCGGGAACCAAACCAGCACTTCAAACCTTATCTGAAACATTTCTTGCCTAAGC
GTTTGCACTTTGCTAAGAGTGATAGAATTGAGCCCTTGACATTCTATTTGGACCCTCAGTGGCAACTTGCATTG
AATCCCTCAGAAAGGAAATATTGTGGAAGTGGATTTCATGGCTCTGACAATGTGTTTTCAAATATGCAAGCCC
TCTTTGTTGGCTATGGACCTGGATTCAAGCATGGCATTGAGGCTGACACCTTTGAAAACATTGAAGTCTATAAC
TTGATGTGTGATTTGCTGAATTTGACACCGGCTCCTAATAACGGAACTCATGGAAGTCTTAACCACCTTCTGAA
GAATCCTGTTTATACGCCAAAGCATCCCAAAGAAGTGCACCCCCTGGTGCAGTGCCCCTTCACAAGAAACCCC
AGAGATAACCTTGGCTGCTCATGTAACCCTTCCATTTTGCCGATTGAGGATTTTCAAACACAGTTCAATCTGAC
CGTGGCAGAAGAGAAGATTATTAAGCATGAAACTTTGCCCTATGGAAGACCTAGAGTTCTCCAGAAGGAAAA
CACCATCTGTCTTCTTTCCCAGCACCAGTTTATGAGTGGATACAGCCAAGACATCTTGATGCCCCTTTGGACATC
CTATACCGTGGACAGAAATGACAGTTTCTCTACGGAAGACTTCTCCAACTGTCTGTACCAGGACTTTAGAATTC
CTCTTAGTCCTGTCCATAAATGTTCATTTTATAAAAATAACACCAAAGTGAGTTACGGGTTCCTCTCCCCACCAC
AACTGAATAAGAATTCAAGTGGAATATATTCTGAAGCCTTGCTTACTACAAATATAGTGCCAATGTACCAGAG
TTTTCAAGTTATATGGCGCTACTTTCATGACACCCTCTTGCGAAAGTATGCAGAAGAAAGAAATGGTGTCAAT
GTCGTCAGTGGTCCTGTGTTTGACTTTGATTATGATGGACGTTGTGATTCCTTGGAGAATTTGAGGCAAAAAA
GAAGAGTCATCCGTAACCAAGAAATTTTGATTCCAACTCATTTCTTCATTGTGCTGACAAGCTGTAAAGATACA
TCTCAGACGCCTTTGCACTGTGAAAACCTGGACACCTTGGCTTTCATTTTGCCTCACAGGACTGATAACAGCGA
GAGCTGTGTGCATGGGAAGCATGACTCCTCATGGGTTGAAGAATTGTTGATGTTGCACAGAGCACGGATCAC
AGACGTCGAGCACATCACTGGACTCAGCTTTTATCAACAAAGAAAAGAGCCAGTTTCAGACATTTTGAAGTTG
AAAACACATTTGCCAACCTTTAGCCAAGAAGAT (SEQ ID NO:7)

Fig. 7 ssNPP1 (signal peptide sequence underlined)

<u>IGVLLTQRTLLSLVLALLFPSMASM</u>AGFETPPTLLFSLDGFRAEYLHTWGGLLPVISKLKKCGTYTKNMRPV
YPTKTFPNHYSIVTGLYPESHGIIDNKMYDPKMNASFSLKSKEKFNPEWYKGEPIWVTAKYQGLKSGTFF
WPGSDVEINGIFPDIYKMYNGSVPFEERILAVLQWLQLPKDERPHFYTLYLEEPDSSGHSYGPVSSEVIKAL
QRVDGMVGMLMDGLKELNLHRCLNLILISDHGMEQGSCKKYIYLNKYLGDVKNIKVIYGPAARLRPSDV
PDKYYSFNYEGIARNLSCREPNQHFKPYLKHFLPKRLHFAKSDRIEPLTFYLDPQWQLALNPSERKYCGSG
FHGSDNVFSNMQALFVGYGPGFKHGIEADTFENIEVYNLMCDLLNLTPAPNNGTHGSLNHLLKNPVYTP
KHPKEVHPLVQCPFTRNPRDNLGCSCNPSILPIEDFQTQFNLTVAEEKIIKHETLPYGRPRVLQKENTICLLS
QHQFMSGYSQDILMPLWTSYTVDRNDSFSTEDFSNCLYQDFRIPLSPVHKCSFYKNNTKVSYGFLSPPQL
NKNSSGIYSEALLTTNIVPMYQSFQVIWRYFHDTLLRKYAEERNGVNVVSGPVFDFDYDGRCDSLENLRQ
KRRVIRNQEILIPTHFFIVLTSCKDTSQTPLHCENLDTLAFILPHRTDNSESCVHGKHDSSWVEELLMLHRA
RITDVEHITGLSFYQQRKEPVSDILKLKTHLPTFSQED (SEQ ID NO:8)

Fig. 8 sNPP1

ATGGGTGTACTGCTCACACAGAGGACGCTGCTCAGTCTGGTCCTTGCACTCCTGTTTCCAAGCATGGCGAGCA
TGCCAAGTTGTGCCAAAGAAGTTAAAAGTTGCAAAGGTCGCTGTTTCGAGAGAACATTTGGGAACTGTCGCT
GTGATGCTGCCTGTGTTGAGCTTGGAAACTGCTGTTTGGATTACCAGGAGACGTGCATAGAACCAGAACATAT
ATGGACTTGCAACAAATTCAGGTGTGGTGAGAAAAGATTGACCAGAAGCCTCTGTGCCTGTTCAGATGATTGC
AAGGACAAGGGCGACTGCTGCATCAACTACAGTTCAGTGTGTCAAGGTGAGAAAAGTTGGGTGGAAGAACC
ATGTGAGAGCATTAATGAGCCACAGTGCCCAGCAGGGTTTGAAACGCCTCCTACACTCTTGTTTTCTTTGGATG
GATTCAGGGCAGAATATTTGCACACTTGGGGTGGACTTCTTCCTGTTATTAGCAAACTCAAAAAATGTGGAAC
ATATACTAAAAACATGAGACCGGTGTATCCAACAAAAACTTTCCCCAATCACTACAGCATTGTCACCGGATTGT
ATCCAGAATCTCATGGCATAATCGACAATAAGATGTATGATCCCAAAATGAATGCTTCCTTTTCACTTAAAAGT
AAAGAGAAATTTAATCCGGAGTGGTACAAAGGAGAACCAATTTGGGTCACAGCTAAGTATCAAGGCCTCAAG
TCTGGCACATTTTTCTGGCCAGGATCAGATGTGGAAATTAACGGAATTTTCCCAGACATCTATAAAATGTATAA
TGGTTCAGTGCCATTTGAAGAAAGGATTTTGGCTGTTCTTCAGTGGCTGCAGCTTCCAAAAGATGAAAGACCA
CACTTTTACACTTTGTATTTGGAAGAACCAGATTCTTCAGGTCATTCATATGGACCAGTCAGCAGTGAAGTCAT
CAAAGCCTTGCAGAGGGTTGATGGTATGGTTGGTATGCTGATGGATGGTCTGAAAGAGCTGAACTTGCACAG
ATGCCTGAACCTCATCCTTATTTCAGATCATGGCATGGAACAAGGCAGTTGTAAGAAATACATATATCTGAATA
AGTATTTGGGGGATGTTAAAAATATTAAAGTTATCTATGGACCTGCAGCTCGATTGAGACCCTCTGATGTCCCA
GATAAATACTATTCATTTAACTATGAAGGCATTGCCCGAAATCTTTCTTGCCGGGAACCAAACCAGCACTTCAA
ACCTTATCTGAAACATTTCTTGCCTAAGCGTTTGCACTTTGCTAAGAGTGATAGAATTGAGCCCTTGACATTCTA
TTTGGACCCTCAGTGGCAACTTGCATTGAATCCCTCAGAAAGGAAATATTGTGGAAGTGGATTTCATGGCTCT
GACAATGTGTTTTCAAATATGCAAGCCCTCTTTGTTGGCTATGGACCTGGATTCAAGCATGGCATTGAGGCTG
ACACCTTTGAAAACATTGAAGTCTATAACTTGATGTGTGATTTGCTGAATTTGACACCGGCTCCTAATAACGGA
ACTCATGGAAGTCTTAACCACCTTCTGAAGAATCCTGTTTATACGCCAAAGCATCCCAAAGAAGTGCACCCCCT
GGTGCAGTGCCCCTTCACAAGAAACCCCAGAGATAACCTTGGCTGCTCATGTAACCCTTCCATTTTGCCGATTG
AGGATTTTCAAACACAGTTCAATCTGACCGTGGCAGAAGAGAAGATTATTAAGCATGAAACTTTGCCCTATGG
AAGACCTAGAGTTCTCCAGAAGGAAAACACCATCTGTCTTCTTTCCCAGCACCAGTTTATGAGTGGATACAGCC
AAGACATCTTGATGCCCCTTTGGACATCCTATACCGTGGACAGAAATGACAGTTTCTCTACGGAAGACTTCTCC
AACTGTCTGTACCAGGACTTTAGAATTCCTCTTAGTCCTGTCCATAAATGTTCATTTTATAAAAATAACACCAAA
GTGAGTTACGGGTTCCTCTCCCCACCACAACTGAATAAGAATTCAAGTGGAATATATTCTGAAGCCTTGCTTAC
TACAAATATAGTGCCAATGTACCAGAGTTTTCAAGTTATATGGCGCTACTTTCATGACACCCTCTTGCGAAAGT
ATGCAGAAGAAAGAAATGGTGTCAATGTCGTCAGTGGTCCTGTGTTTGACTTTGATTATGATGGACGTTGTGA
TTCCTTGGAGAATTTGAGGCAAAAAAGAAGAGTCATCCGTAACCAAGAAATTTTGATTCCAACTCATTTCTTCA
TTGTGCTGACAAGCTGTAAAGATACATCTCAGACGCCTTTGCACTGTGAAAACCTGGACACCTTGGCTTTCATT
TTGCCTCACAGGACTGATAACAGCGAGAGCTGTGTGCATGGGAAGCATGACTCCTCATGGGTTGAAGAATTG
TTGATGTTGCACAGAGCACGGATCACAGACGTCGAGCACATCACTGGACTCAGCTTTTATCAACAAAGAAAAG
AGCCAGTTTCAGACATTTTGAAGTTGAAAACACATTTGCCAACCTTTAGCCAAGAAGAT (SEQ ID NO:9)

Fig. 9 sNPP1

IGVLLTQRTLLSLVLALLFPSMASMPSCAKEVKSCKGRCFERTFGNCRCDAACVELGNCCLDYQETCIEPE
HIWTCNKFRCGEKRLTRSLCACSDDCKDKGDCCINYSSVCQGEKSWVEEPCESINEPQCPAGFETPPTLLF
SLDGFRAEYLHTWGGLLPVISKLKKCGTYTKNMRPVYPTKTFPNHYSIVTGLYPESHGIIDNKMYDPKMN
ASFSLKSKEKFNPEWYKGEPIWVTAKYQGLKSGTFFWPGSDVEINGIFPDIYKMYNGSVPFEERILAVLQ
WLQLPKDERPHFYTLYLEEPDSSGHSYGPVSSEVIKALQRVDGMVGMLMDGLKELNLHRCLNLILISDHG
MEQGSCKKYIYLNKYLGDVKNIKVIYGPAARLRPSDVPDKYYSFNYEGIARNLSCREPNQHFKPYLKHFLPK
RLHFAKSDRIEPLTFYLDPQWQLALNPSERKYCGSGFHGSDNVFSNMQALFVGYGPGFKHGIEADTFENI
EVYNLMCDLLNLTPAPNNGTHGSLNHLLKNPVYTPKHPKEVHPLVQCPFTRNPRDNLGCSCNPSILPIED
FQTQFNLTVAEEKIIKHETLPYGRPRVLQKENTICLLSQHQFMSGYSQDILMPLWTSYTVDRNDSFSTEDF
SNCLYQDFRIPLSPVHKCSFYKNNTKVSYGFLSPPQLNKNSSGIYSEALLTTNIVPMYQSFQVIWRYFHDTL
LRKYAEERNGVNVVSGPVFDFDYDGRCDSLENLRQKRRVIRNQEILIPTHFFIVLTSCKDTSQTPLHCENLD
TLAFILPHRTDNSESCVHGKHDSSWVEELLMLHRARITDVEHITGLSFYQQRKEPVSDILKLKTHLPTFSQE
D (SEQ ID NO:10)

Fig. 10

TAGsNPP1 (N-terminus D8)

ATGGGTGTACTGCTCACACAGAGGACGCTGCTCAGTCTGGTCCTTGCACTCCTGTTTCCAAGCATGGCGAGCA
TGGATGACGATGATGACGACGATGACCCAAGTTGTGCCAAAGAAGTTAAAAGTTGCAAAGGTCGCTGTTTCG
AGAGAACATTTGGGAACTGTCGCTGTGATGCTGCCTGTGTTGAGCTTGGAAACTGCTGTTTGGATTACCAGGA
GACGTGCATAGAACCAGAACATATATGGACTTGCAACAAATTCAGGTGTGGTGAGAAAAGATTGACCAGAAG
CCTCTGTGCCTGTTCAGATGATTGCAAGGACAAGGGCGACTGCTGCATCAACTACAGTTCAGTGTGTCAAGGT
GAGAAAAGTTGGGTGGAAGAACCATGTGAGAGCATTAATGAGCCACAGTGCCCAGCAGGGTTTGAAACGCC
TCCTACACTCTTGTTTTCTTTGGATGGATTCAGGGCAGAATATTTGCACACTTGGGGTGGACTTCTTCCTGTTAT
TAGCAAACTCAAAAAATGTGGAACATATACTAAAAACATGAGACCGGTGTATCCAACAAAAACTTTCCCCAAT
CACTACAGCATTGTCACCGGATTGTATCCAGAATCTCATGGCATAATCGACAATAAGATGTATGATCCCAAAAT
GAATGCTTCCTTTTCACTTAAAAGTAAAGAGAAATTTAATCCGGAGTGGTACAAAGGAGAACCAATTTGGGTC
ACAGCTAAGTATCAAGGCCTCAAGTCTGGCACATTTTTCTGGCCAGGATCAGATGTGGAAATTAACGGAATTT
TCCCAGACATCTATAAAATGTATAATGGTTCAGTGCCATTTGAAGAAAGGATTTTGGCTGTTCTTCAGTGGCTG
CAGCTTCCAAAAGATGAAAGACCACACTTTTACACTTTGTATTTGGAAGAACCAGATTCTTCAGGTCATTCATA
TGGACCAGTCAGCAGTGAAGTCATCAAAGCCTTGCAGAGGGTTGATGGTATGGTTGGTATGCTGATGGATGG
TCTGAAAGAGCTGAACTTGCACAGATGCCTGAACCTCATCCTTATTTCAGATCATGGCATGGAACAAGGCAGT
TGTAAGAAATACATATATCTGAATAAGTATTTGGGGGATGTTAAAAATATTAAAGTTATCTATGGACCTGCAG
CTCGATTGAGACCCTCTGATGTCCCAGATAAATACTATTCATTTAACTATGAAGGCATTGCCCGAAATCTTTCTT
GCCGGGAACCAAACCAGCACTTCAAACCTTATCTGAAACATTTCTTGCCTAAGCGTTTGCACTTTGCTAAGAGT
GATAGAATTGAGCCCTTGACATTCTATTTGGACCCTCAGTGGCAACTTGCATTGAATCCCTCAGAAAGGAAAT
ATTGTGGAAGTGGATTTCATGGCTCTGACAATGTGTTTTCAAATATGCAAGCCCTCTTTGTTGGCTATGGACCT
GGATTCAAGCATGGCATTGAGGCTGACACCTTTGAAAACATTGAAGTCTATAACTTGATGTGTGATTTGCTGA
ATTTGACACCGGCTCCTAATAACGGAACTCATGGAAGTCTTAACCACCTTCTGAAGAATCCTGTTTATACGCCA
AAGCATCCCAAAGAAGTGCACCCCCTGGTGCAGTGCCCCTTCACAAGAAACCCCAGAGATAACCTTGGCTGCT
CATGTAACCCTTCCATTTTGCCGATTGAGGATTTTCAAACACAGTTCAATCTGACCGTGGCAGAAGAGAAGATT
ATTAAGCATGAAACTTTGCCCTATGGAAGACCTAGAGTTCTCCAGAAGGAAAACACCATCTGTCTTCTTTCCCA
GCACCAGTTTATGAGTGGATACAGCCAAGACATCTTGATGCCCCTTTGGACATCCTATACCGTGGACAGAAAT
GACAGTTTCTCTACGGAAGACTTCTCCAACTGTCTGTACCAGGACTTTAGAATTCCTCTTAGTCCTGTCCATAAA
TGTTCATTTTATAAAAATAACACCAAAGTGAGTTACGGGTTCCTCTCCCCACCACAACTGAATAAGAATTCAAG
TGGAATATATTCTGAAGCCTTGCTTACTACAAATATAGTGCCAATGTACCAGAGTTTTCAAGTTATATGGCGCT
ACTTTCATGACACCCTCTTGCGAAAGTATGCAGAAGAAAGAAATGGTGTCAATGTCGTCAGTGGTCCTGTGTT
TGACTTTGATTATGATGGACGTTGTGATTCCTTGGAGAATTTGAGGCAAAAAAGAAGAGTCATCCGTAACCAA
GAAATTTTGATTCCAACTCATTTCTTCATTGTGCTGACAAGCTGTAAAGATACATCTCAGACGCCTTTGCACTGT
GAAAACCTGGACACCTTGGCTTTCATTTGCCTCACAGGACTGATAACAGCGAGAGCTGTGTGCATGGGAAGC
ATGACTCCTCATGGGTTGAAGAATTGTTGATGTTGCACAGAGCACGGATCACAGACGTCGAGCACATCACTGG
ACTCAGCTTTTATCAACAAAGAAAAGAGCCAGTTTCAGACATTTTGAAGTTGAAAACACATTTGCCAACCTTTA
GCCAAGAAGAT (SEQ ID NO:11)

Fig. 11

TAGsNPP1 (N-terminus D8)

<u>IGVLLTQRTLLSLVLALLFPSMASM</u>DDDDDDDDPSCAKEVKSCKGRCFERTFGNCRCDAACVELGNCCL
DYQETCIEPEHIWTCNKFRCGEKRLTRSLCACSDDCKDKGDCCINYSSVCQGEKSWVEEPCESINEPQCP
AGFETPPTLLFSLDGFRAEYLHTWGGLLPVISKLKKCGTYTKNMRPVYPTKTFPNHYSIVTGLYPESHGIID
NKMYDPKMNASFSLKSKEKFNPEWYKGEPIWVTAKYQGLKSGTFFWPGSDVEINGIFPDIYKMYNGSV
PFEERILAVLQWLQLPKDERPHFYTLYLEEPDSSGHSYGPVSSEVIKALQRVDGMVGMLMDGLKELNLH
RCLNLILISDHGMEQGSCKKYIYLNKYLGDVKNIKVIYGPAARLRPSDVPDKYYSFNYEGIARNLSCREPNQ
HFKPYLKHFLPKRLHFAKSDRIEPLTFYLDPQWQLALNPSERKYCGSGFHGSDNVFSNMQALFVGYGPGF
KHGIEADTFENIEVYNLMCDLLNLTPAPNNGTHGSLNHLLKNPVYTPKHPKEVHPLVQCPFTRNPRDNL
GCSCNPSILPIEDFQTQFNLTVAEEKIIKHETLPYGRPRVLQKENTICLLSQHQFMSGYSQDILMPLWTSYT
VDRNDSFSTEDFSNCLYQDFRIPLSPVHKCSFYKNNTKVSYGFLSPPQLNKNSSGIYSEALLTTNIVPMYQS
FQVIWRYFHDTLLRKYAEERNGVNVVSGPVFDFDYDGRCDSLENLRQKRRVIRNQEILIPTHFFIVLTSCK
DTSQTPLHCENLDTLAFILPHRTDNSESCVHGKHDSSWVEELLMLHRARITDVEHITGLSFYQQRKEPVSD
ILKLKTHLPTFSQED (SEQ ID NO:12)

Fig. 12

TAGsNPP1 (C-terminus D8)

GTGGGTGTACTGCTCACACAGAGGACGCTGCTCAGTCTGGTCCTTGCACTCCTGTTTCCAAGCATGGCGAGCA
TGCCAAGTTGTGCCAAAGAAGTTAAAAGTTGCAAAGGTCGCTGTTTCGAGAGAACATTTGGGAACTGTCGCT
GTGATGCTGCCTGTGTTGAGCTTGGAAACTGCTGTTTGGATTACCAGGAGACGTGCATAGAACCAGAACATAT
ATGGACTTGCAACAAATTCAGGTGTGGTGAGAAAAGATTGACCAGAAGCCTCTGTGCCTGTTCAGATGATTGC
AAGGACAAGGGCGACTGCTGCATCAACTACAGTTCAGTGTGTCAAGGTGAGAAAAGTTGGGTGGAAGAACC
ATGTGAGAGCATTAATGAGCCACAGTGCCCAGCAGGGTTTGAAACGCCTCCTACACTCTTGTTTTCTTTGGATG
GATTCAGGGCAGAATATTTGCACACTTGGGGTGGACTTCTTCCTGTTATTAGCAAACTCAAAAAATGTGGAAC
ATATACTAAAAACATGAGACCGGTGTATCCAACAAAAACTTTCCCCAATCACTACAGCATTGTCACCGGATTGT
ATCCAGAATCTCATGGCATAATCGACAATAAGATGTATGATCCCAAAATGAATGCTTCCTTTTCACTTAAAAGT
AAAGAGAAATTTAATCCGGAGTGGTACAAAGGAGAACCAATTTGGGTCACAGCTAAGTATCAAGGCCTCAAG
TCTGGCACATTTTTCTGGCCAGGATCAGATGTGGAAATTAACGGAATTTTCCCAGACATCTATAAAATGTATAA
TGGTTCAGTGCCATTTGAAGAAAGGATTTTGGCTGTTCTTCAGTGGCTGCAGCTTCCAAAAGATGAAAGACCA
CACTTTTACACTTTGTATTTGGAAGAACCAGATTCTTCAGGTCATTCATATGGACCAGTCAGCAGTGAAGTCAT
CAAAGCCTTGCAGAGGGTTGATGGTATGGTTGGTATGCTGATGGATGGTCTGAAAGAGCTGAACTTGCACAG
ATGCCTGAACCTCATCCTTATTTCAGATCATGGCATGGAACAAGGCAGTTGTAAGAAATACATATATCTGAATA
AGTATTTGGGGGATGTTAAAAATATTAAAGTTATCTATGGACCTGCAGCTCGATTGAGACCCTCTGATGTCCCA
GATAAATACTATTCATTTAACTATGAAGGCATTGCCCGAAATCTTTCTTGCCGGGAACCAAACCAGCACTTCAA
ACCTTATCTGAAACATTTCTTGCCTAAGCGTTTGCACTTTGCTAAGAGTGATAGAATTGAGCCCTTGACATTCTA
TTTGGACCCTCAGTGGCAACTTGCATTGAATCCCTCAGAAAGGAAATATTGTGGAAGTGGATTTCATGGCTCT
GACAATGTGTTTTCAAATATGCAAGCCCTCTTTGTTGGCTATGGACCTGGATTCAAGCATGGCATTGAGGCTG
ACACCTTTGAAAACATTGAAGTCTATAACTTGATGTGTGATTTGCTGAATTTGACACCGGCTCCTAATAACGGA
ACTCATGGAAGTCTTAACCACCTTCTGAAGAATCCTGTTTATACGCCAAAGCATCCCAAAGAAGTGCACCCCCT
GGTGCAGTGCCCCTTCACAAGAAACCCCAGAGATAACCTTGGCTGCTCATGTAACCCTTCCATTTTGCCGATTG
AGGATTTTCAAACACAGTTCAATCTGACCGTGGCAGAAGAGAAGATTATTAAGCATGAAACTTTGCCCTATGG
AAGACCTAGAGTTCTCCAGAAGGAAAACACCATCTGTCTTCTTTCCCAGCACCAGTTTATGAGTGGATACAGCC
AAGACATCTTGATGCCCCTTTGGACATCCTATACCGTGGACAGAAATGACAGTTTCTCTACGGAAGACTTCTCC
AACTGTCTGTACCAGGACTTTAGAATTCCTCTTAGTCCTGTCCATAAATGTTCATTTTATAAAAATAACACCAAA
GTGAGTTACGGGTTCCTCTCCCCACCACAACTGAATAAGAATTCAAGTGGAATATATTCTGAAGCCTTGCTTAC
TACAAATATAGTGCCAATGTACCAGAGTTTTCAAGTTATGGCGCTACTTTCATGACACCCTCTTGCGAAAGT
ATGCAGAAGAAAGAAATGGTGTCAATGTCGTCAGTGGTCCTGTGTTTGACTTTGATTATGATGGACGTTGTGA
TTCCTTGGAGAATTTGAGGCAAAAAGAAGAGTCATCCGTAACCAAGAAATTTTGATTCCAACTCATTTCTTCA
TTGTGCTGACAAGCTGTAAAGATACATCTCAGACGCCTTTGCACTGTGAAAACCTGGACACCTTGGCTTTCATT
TTGCCTCACAGGACTGATAACAGCGAGAGCTGTGTGCATGGGAAGCATGACTCCTCATGGGTTGAAGAATTG
TTGATGTTGCACAGAGCACGGATCACAGACGTCGAGCACATCACTGGACTCAGCTTTTATCAACAAAGAAAAG
AGCCAGTTTCAGACATTTTGAAGTTGAAAACACATTTGCCAACCTTTAGCCAAGAAGATGATGACGATGATGA
CGACGATTGA (SEQ ID NO:13)

Fig. 13

TAGsNPP1 (C-terminus D8; signal peptide sequence underlined and the targeting moiety in bold)

<u>QGVLLTQRTLLSLVLALLFPSMASM</u>PSCAKEVKSCKGRCFERTFGNCRCDAACVELGNCCLDYQETCIEPEHIWTCN
KFRCGEKRLTRSLCACSDDCKDKGDCCINYSSVCQGEKSWVEEPCESINEPQCPAGFETPPTLLFSLDGFRAEYLHT
WGGLLPVISKLKKCGTYTKNMRPVYPTKTFPNHYSIVTGLYPESHGIIDNKMYDPKMNASFSLKSKEKFNPEWYKG
EPIWVTAKYQGLKSGTFFWPGSDVEINGIFPDIYKMYNGSVPFEERILAVLQWLQLPKDERPHFYTLYLEEPDSSGH
SYGPVSSEVIKALQRVDGMVGMLMDGLKELNLHRCLNLILISDHGMEQGSCKKYIYLNKYLGDVKNIKVIYGPAARL
RPSDVPDKYYSFNYEGIARNLSCREPNQHFKPYLKHFLPKRLHFAKSDRIEPLTFYLDPQWQLALNPSERKYCGSGFH
GSDNVFSNMQALFVGYGPGFKHGIEADTFENIEVYNLMCDLLNLTPAPNNGTHGSLNHLLKNPVYTPKHPKEVHP
LVQCPFTRNPRDNLGCSCNPSILPIEDFQTQFNLTVAEEKIIKHETLPYGRPRVLQKENTICLLSQHQFMSGYSQDIL
MPLWTSYTVDRNDSFSTEDFSNCLYQDFRIPLSPVHKCSFYKNNTKVSYGFLSPPQLNKNSSGIYSEALLTTNIVPMY
QSFQVIWRYFHDTLLRKYAEERNGVNVVSGPVFDFDYDGRCDSLENLRQKRRVIRNQEILIPTHFFIVLTSCKDTSQT
PLHCENLDTLAFILPHRTDNSESCVHGKHDSSWVEELLMLHRARITDVEHITGLSFYQQRKEPVSDILKLKTHLPTFS
QEDDDDDDDD (SEQ ID NO:14)

Fig. 14

Linker peptide

GGGGSGGGGS (SEQ ID NO:15 )

Fig. 15

The amino acid sequence of the Fc region

EPKSCDKTHTCPPCPAPEAAGAPSVFLFPPKPKDTLMISRTPEVTCVVVDVSH EDPEVKFNWY
VDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDSDGSFFLYS
KLTVDKSRWQ QGNVFSCSVMHEALHNHYTQKSLSLSPGK (SEQ ID NO:16 )

Fig. 16

The amino acid sequence of TAGsssNPP1 (N-terminus D8) + Fc + Linker

<u>IGVLLTQRTLLSLVLALLFPSMASM</u>EPKSCDKTHTCPPCPAPEAAGAPSVFLFPPKPKDTLMISRTPEVTCV
VVDVSHEDPEVKFNWYVDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWESNGQPENNYKTTPPVLDS
DGSFFLYS KLTVDKSRWQ QGNVFSCSVM HEALHNHYTQ KSLSLSPGK DDDDDDDD
*GGGGSGGGGS*AGFETPPTLLFSLDGFRAEYLHTWGGLLPVISKLKKCGTYTKNMRPVYPTKTFPNHYSIVT
GLYPESHGIIDNKMYDPKMNASFSLKSKEKFNPEWYKGEPIWVTAKYQGLKSGTFFWPGSDVEINGIFPDI
YKMYNGSVPFEERILAVLQWLQLPKDERPHFYTLYLEEPDSSGHSYGPVSSEVIKALQRVDGMVGMLMD
GLKELNLHRCLNLILISDHGMEQGSCKKYIYLNKYLGDVKNIKVIYGPAARLRPSDVPDKYYSFNYEGIARNL
SCREPNQHFKPYLKHFLPKRLHFAKSDRIEPLTFYLDPQWQLALNPSERKYCGSGFHGSDNVFSNMQALF
VGYGPGFKHGIEADTFENIEVYNLMCDLLNLTPAPNNGTHGSL (SEQ ID NO:17 )

Fig. 17

The amino acid sequence of TAGsssNPP1 (C-terminus D8) + Fc + Linker

IGVLLTQRTLLSLVLALLFPSMASM*EPKSCDKTHTCPPCPAPEAAGAPSVFLFPPKPKDTLMISRTPEVTCV VVDVSHEDPEVKFNWYVDGVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWESNGQPENNYKTTPPVLDSD GSFFLYSKLTVDKSRWQQGNVFSCSVMHEALHNHYTQKSLSLSPGK*AGFETPPTLLFSLDGFRAEYLHTW GGLLPVISKLKKCGTYTKNMRPVYPTKTFPNHYSIVTGLYPESHGIIDNKMYDPKMNASFSLKSKEKFNPE WYKGEPIWVTAKYQGLKSGTFFWPGSDVEINGIFPDIYKMYNGSVPFEERILAVLQWLQLPKDERPHFYT LYLEEPDSSGHSYGPVSSEVIKALQRVDGMVGMLMDGLKELNLHRCLNLILISDHGMEQGSCKKYIYLNKY LGDVKNIKVIYGPAARLRPSDVPDKYYSFNYEGIARNLSCREPNQHFKPYLKHFLPKRLHFAKSDRIEPLTFYL DPQWQLALNPSERKYCGSGFHGSDNVFSNMQALFVGYGPGFKHGIEADTFENIEVYNLMCDLLNLTPAP NNGTHGSL*GGGGSGGGGS* DDDDDDDD (SEQ ID NO: 18)

NPP1 FUSION PROTEINS

RELATED APPLICATION

This application is a continuation of U.S. patent application Ser. No. 13/583,973, which is the National Stage of International Application No. PCT/US2011/028233, filed Mar. 11, 2011, which claims the benefit of U.S. Provisional Application No. 61/340,066, filed on Mar. 12, 2010. The entire teachings of the above applications are incorporated herein by reference.

SEQUENCE LISTING

The instant application contains a Sequence Listing that was submitted electronically in ASCII format and is hereby incorporated by reference in its entirety. Said ASCII copy, created on Jul. 31, 2014, is named 077USCON_SEQ_List.txt and is 84,422 bytes in size.

BACKGROUND OF THE INVENTION

Ectonucleotide pyrophosphatase/phosphodiesterase 1 (NPP1/ENPP1/PC-1) is a type II transmembrane glycoprotein that forms a homodimer. The protein cleaves a variety of substrates, including phosphodiester bonds of nucleotides and nucleotide sugars and pyrophosphate bonds of nucleotides and nucleotide sugars. NPP1 protein functions to hydrolyze nucleoside 5' triphoshtase to either corresponding monophosphates and also hydrolyzes diadenosine polyphosphates. Mutations in the NPP1 gene have been associated with idiopathic infantile arterial calcification (IIAC), insulin resistance, hypophosphatemic rickets, and ossification of the posterior longitudinal ligament of the spine.

IIAC, a rare autosomal recessive and nearly always fatal disorder, is characterized by calcification of the internal elastic lamina of muscular arteries and stenosis due to myointimal proliferation. There are more than 160 cases of IIAC that have been reported world-wide. The symptoms of the disease most often appear by early infancy, and the disease is lethal by 6 months of age, generally because of ischemic cardiomyopathy, and other complications of obstructive arteriopathy including renal artery stenosis. In more than a dozen reported cases of IIAC, periarticular calcifications of large joints also developed in infancy. Rutsch et al. (2003) reported that mutations in ENPP1 are associated with IIAC characterized by the spontaneous periarticular and aortic calcifications in early life and systemic lowering of nucleotide pyrophosphatase/phosphodiesterase activity in the affected individuals.

Although defects in the NPP1 protein have been implicated in such serious disease as IIAC, there is no treatment available in the art for those who are affected by the disease. Therefore, a dire need exists for an effective and safe composition, formulation and medicament for the treatment of IIAC, insulin resistance, hypophosphatemic rickets, and ossification of the posterior longitudinal ligament of the spine.

SUMMARY OF THE INVENTION

The present invention includes fusion proteins of truncated domains of NPP1 (i.e., an NPP1 component) fused to a targeting moiety. The targeting moiety functions to enhance the efficiency in targeting the NPP1 fusion protein to a site clinical or biological importance (e.g., site of calcification in a subject that needs lowering of calcification). Without wishing to limit the invention to any particular theory or mechanism of operation it is believed that the NPP1 component function to inhibit calcification by enhancing the formation of pyrophosphate (PPi) and/or by cleaving pyrophosphate to produce soluble phosphate (Pi) and/or by increasing the availability of adenosine monophosphate (AMP) and/or adenosine. It is contemplated that the targeting moiety can be attached to the N-terminus and/or the C-terminus of the NPP1 component at any useful position. Additionally, the NPP1 fusion protein disclosed herein can also include one or more of Fc fragment, PEG, polypeptide linker or other additional polypeptides to enhance the enzymatic activity, stability or targeting.

The fusion proteins of the invention can be used to treat a wide variety of conditions in a subject. Any condition that can be beneficially treated by the administering of a fusion protein of the invention is included within the scope of the invention. For example, treatment of conditions that can be improved by reducing and/or eliminating one or more calcification structures and/or preventing calcification structures from forming in a subject such as a mammal, for example, a human patient is within the scope of the invention. Conditions such as arterial blockage are contemplated for treatment by employing fusion proteins of the invention. In one particularly useful embodiment, the condition to be treated is generalized arterial calcification of infancy also referred to as idiopathic arterial calcification of infancy and arterial media calcification of infancy. Conditions such as insulin resistance, hypophosphatemic rickets, and ossification of the posterior longitudinal ligament of the spine are also contemplated for treatment.

Fusion proteins of the invention can be produced in any useful protein expression system including, without limitation, cell culture (e.g., CHO cells, COS cells, HEK293), bacteria such as *Escherichia coli* (*E. coli*) and transgenic animals, including, but not limited to, mammals and avians (e.g., chickens, quail, duck and turkey).

The manufacture of pharmaceutical compositions (or pharmaceutical formulations) is well known in the art and such pharmaceutical compositions are contemplated for use in accordance with fusion proteins of the invention.

Generally, the dosage of fusion protein administered to a subject will vary depending upon known factors such as age, health and weight of the recipient, type of concurrent treatment, frequency of treatment, and the like. Usually, a dosage of active ingredient (i.e., fusion protein) can be between about 0.0001 and about 50 milligrams per kilogram of body weight. Precise dosage, frequency of administration and time span of treatment can be determined by a physician skilled in the art of administration of therapeutic proteins.

BRIEF DESCRIPTION OF THE DRAWINGS

FIG. 1 illustrates the amino acid sequence of wild-type NPP1 protein. The cytosolic and transmembrane regions are underlined. The potential N-glycosylation sites are in bold. PSCAKE in italics is the start of soluble NPP1 which includes the cysteine rich region.

FIG. 2 illustrates the amino acid sequence of the catalytic domain(s) of NPP1 protein having no target moiety attached ("sssNPP1").

FIG. 3 illustrates the amino acid sequence of TAGsss-NPP1. The targeting moiety of eight consecutive aspartic acid residues is fused to the N-terminus of the sssNPP1. The signal peptide is underlined and the targeting moiety is indicated in bold.

FIG. 4 illustrates the amino acid sequence of TAGsss-NPP1 that contains the targeting moiety of ten consecutive aspartic acid residues fused to the C-terminus of the sss-NPP1. The signal peptide is underlined and the targeting moiety is indicated in bold.

FIG. 5 illustrates the nucleic acid sequence of TAGss-NPP1 fusion protein. The targeting moiety of eight consecutive aspartic acid residues is fused to the N-terminus of the ssNPP1.

FIG. 6 illustrates the amino acid sequence of TAGssNPP1 fusion protein. The targeting moiety of eight consecutive aspartic acid residues is fused to the N-terminus of the ssNPP1. The signal peptide is underlined and the targeting moiety is indicated in bold.

FIG. 7 illustrates the nucleic acid sequence of ssNPP1.

FIG. 8 illustrates the amino acid sequence of ssNPP1. The signal peptide is underlined.

FIG. 9 illustrates the nucleic acid sequence of sNPP1.

FIG. 10 illustrates the amino acid sequence of sNPP1. The signal peptide is underlined.

FIG. 11 illustrates the nucleic acid sequence of TAG-sNPP1. The targeting moiety of eight consecutive aspartic acid residues is fused to the N-terminus of the sNPP1.

FIG. 12 illustrates the amino acid sequence of TAG-sNPP1. The targeting moiety of eight consecutive aspartic acid residues is fused to the N-terminus of the ssNPP1. The signal peptide is underlined and the targeting moiety is indicated in bold.

FIG. 13 illustrates the nucleic acid sequence of TAG-sNPP1. The targeting moiety of eight consecutive aspartic acid residues is fused to the C-terminus of the sNPP1.

FIG. 14 illustrates the amino acid sequence of TAG-sNPP1. The targeting moiety of eight consecutive aspartic acid residues is fused to the N-terminus of the sNPP1. The signal peptide is underlined and the targeting moiety is indicated in bold.

FIG. 15 illustrates the amino acid sequence of a linker peptide.

FIG. 16 illustrates the amino acid sequence of an immunoglobulin Fc segment.

FIG. 17 illustrates the amino acid sequence of TAGsss-NPP1 which contains the targeting moiety of eight consecutive aspartic acid residues fused to the N-terminus of the sssNPP1 via a peptide linker. The Fc segment is fused to N-terminus of the target moiety. The signal peptide is underlined and the targeting moiety is indicated in bold. The peptide linker is in italics.

FIG. 18 illustrates the amino acid sequence of TAGsss-NPP1 which contains the targeting moiety of eight consecutive aspartic acid residues fused to the C-terminus of the sssNPP1 via a peptide linker. The Fc segment is fused to N-terminus of the sssNPP1. The signal peptide is underlined and the targeting moiety is indicated in bold. The peptide linker is in italics.

Figure 22B:
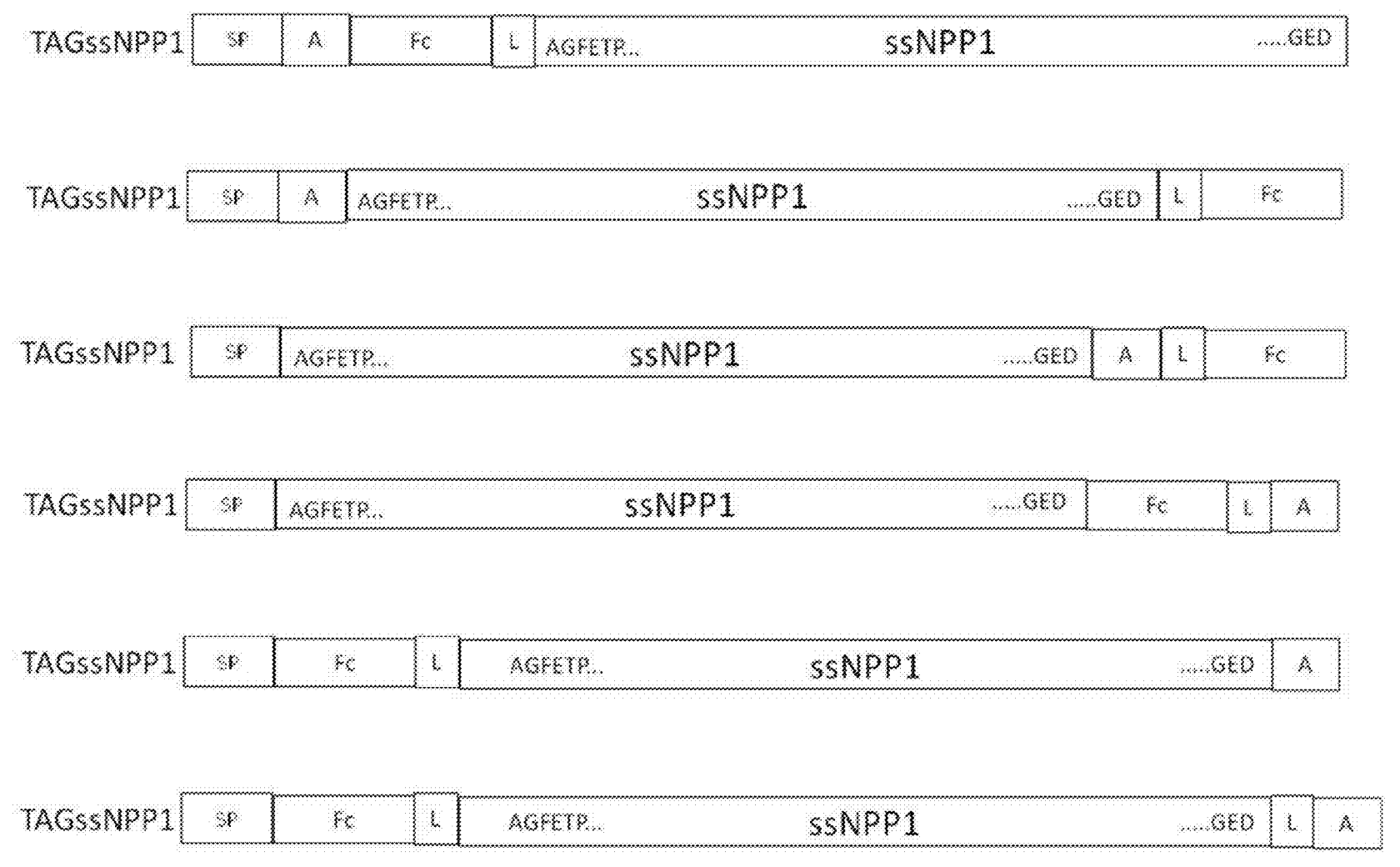

FIGS. 22A-22C illustrate schematics of TAGNPP1 fusion protein constructs described herein.

DETAILED DESCRIPTION OF THE INVENTION

Figure 19:
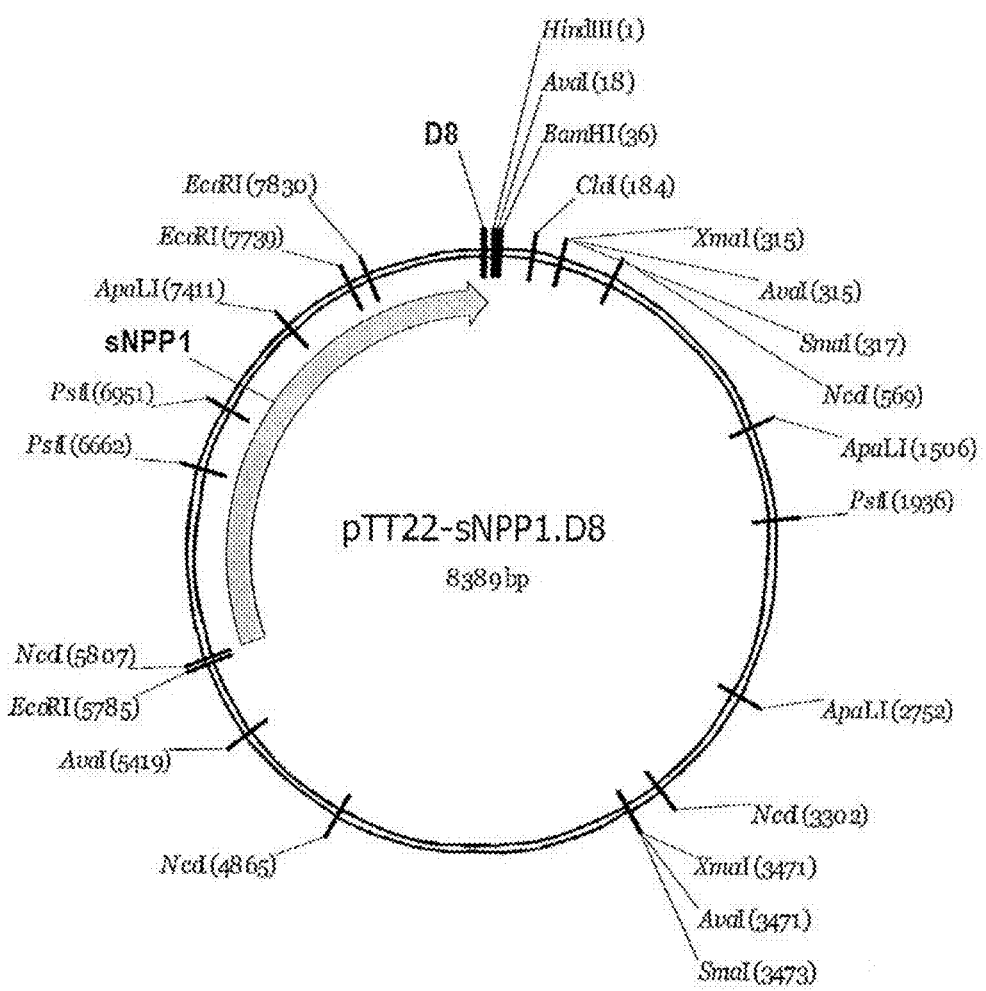
FIG. 19 is a schematic representation of an expression vector (i.e., pTT22) containing a TAGsNPP1 construct. The targeting moiety of eight consecutive aspartic acid residues fused to the C-terminus of the sNPP1.
Figure 20:
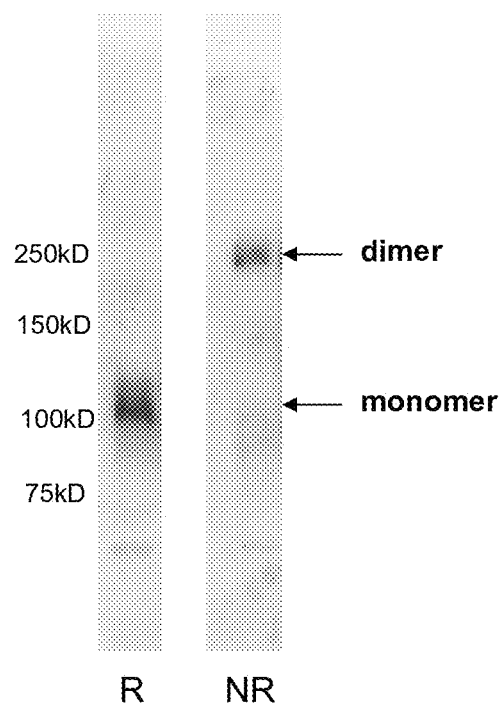
FIG. 20 illustrates Western blot analysis of TAGsNPP1. R, reducing condition; NR, non-reducing condition.

The present invention provides novel human NPP1 fusion proteins that are soluble and contain truncated and biologically active domain(s) of NPP1 (i.e., NPP1 components that contain at least one extracellular catalytic domain of naturally occurring NPP1 for the pyrophosphatase and/or phosphodiesterase activity) and one or more targeting moieties (i.e., "TAG"). The NPP1 fusion proteins of the present invention comprise at least the NPP1 domain essential to carry out the pyrophosphatase and/or phosphodiesterase activity. Accordingly, the invention features isolated fusion proteins comprising the amino acid residues A205 through L591 of SEQ ID NO:1 fused to one or more targeting moieties. The targeting moiety can be recombinantly fused or chemically bonded (e.g., covalent bond, ionic bond, hydrophobic bond and Van der Waals force) to the NPP1 component by methods well known in the art and direct the NPP1 component to a certain target site where the attached NPP1 component will have a desirable effect (e.g., catalysis of a reaction such as solubilizing a substrate such as PPi or preventing the formation of a substrate such as PPi) in a subject to which the fusion protein of the present invention is administered.

TAGNPP1s

All NPP1 fusion proteins ("TAGNPP1s") of the present invention have the N-terminal cytosolic and the transmembrane domains of the naturally occurring human NPP1 removed. Optionally, TAGNPP1s fusion proteins of the present invention can also contain C-terminal truncation of wild-type NPP1 in various lengths. The amino acid sequence of full-length wild-type NPP1 is set forth in SEQ ID NO: 1.

In one embodiment, the fusion protein contains a polypeptide comprising the amino acid residues A205 through L591 of SEQ ID NO:1 ("sssNPP1") fused a TAG on either the N- or C-terminus of the polypeptide ("TAGsssNPP1"). In one embodiment, the fusion protein comprises a polypeptide comprising the amino acid residues A205 through D925 of SEQ ID NO:1 ("ssNPP1") fused to a TAG on either the N- or C-terminus ("TAGssNPP1"). In one embodiment, the fusion protein comprises a polypeptide comprising the amino acid residues P99 through D925 of SEQ ID NO:1 ("sNPP1") fused to a TAG on either the N- or C-terminus of the polypeptide ("TAGsNPP1"). Also contemplated is any consecutive fragment of sNPP1 that comprises at least the amino acid resides A205 through L591 of SEQ ID NO:1 and the polypeptide fragment is fused to a TAG on either the N- or C-terminus.

When expressed in a cell culture or transgenic animal, the TAGNPP1 fusion proteins can further comprise a signal peptide (or leader sequence) at its N-terminus. The signal peptide co-translationally or post-translationally directs transport of the TAGNPP1 fusion proteins through the subcellular organelles of the cell expressing the TAGNPP1 fusion proteins and, thereby determining the post-translational modification of the TAGNPP1 fusion proteins. It is to be understood that because the signal peptide is cleaved at the co-translational or post-translational stage of the fusion protein, the TAGNNP1 fusion proteins are generally devoid of the signal peptide when once secreted and isolated. Accordingly, in the embodiments that are directed to the nucleic acid sequences encoding the TAGNPP1 fusion proteins are described, the leader sequences are also contemplated as used in the present invention. For example, the nucleotide sequence set forth in SEQ ID NO:2 contains an example of the leader sequence for TAGNNP1 at its 5' end.

Each of the fusion proteins disclosed herein is contemplated with one or more targeting moieties ("TAG"). The TAG component according to the present invention comprises four or more negatively charged amino acids such as aspartic acid and glutamic acid. The TAG component can be a stretch of negatively charged amino acid residues, for example, aspartic acids and/or glutamic acids that are between about 4 and about 20 amino acid residues in length. The TAG can be fused to either the N- or C-terminus of the NPP1 component. The TAG can be also fused to both N- and C-termini of the NPP1 component. Accordingly, the amino acid sequence of the TAGsNPP1 fusion protein, for example, includes PSCAKE through the C-terminus end of the NPP1 component and one or more targeting moieties (e.g., polyglutamic acid tag or polyaspartic acid tag) at the N- and/or C-terminus end of the NPP1 component. The fusion protein comprising the NPP1 component having the TAG fused to the C-terminus is a particularly useful embodiment. In one very specific embodiment, TAG having a stretch of eight aspartic acids is employed as can be seen in the exemplary sequences for TAGsNPP1 and TAGssNPP1 in Figures, though any useful number of negatively charged amino acid residues (e.g., 4, 5, 6, 7, 9, 10, 11, 12, 13, 14, 15, 16, 17, or 18) can be used in accordance with the invention. The TAG component is indicated as "A" in Figures.

The invention also encompasses polynucleotides which encode various TAGNPP1 fusion proteins described herein. Accordingly, any nucleic acid sequence which encodes the amino acid sequence of any TAGNPP1 fusion protein can be used to generate recombinant molecules which express the corresponding TAGNPP1 fusion protein. In a particular embodiment, the invention encompasses the polynucleotide comprising the nucleic acid sequence of SEQ ID NO:2 as shown in FIG. 2.

Within certain specific embodiments, the fusion protein comprises multiple polypeptides as described herein, or that comprises at least one polypeptide as described herein and an unrelated sequence. Certain preferred polypeptide can, for example, assist in dimerization and stability or minimize aggregation of the fusion proteins. For example, the additional polypeptide can be the Fc region of the immunoglobulin G1 to increase stability in serum. The use of the Fc segment is well known in the art and described in U.S. Pat. No. 7,902,151; and U.S. Pat. No. 7,858,297, the entire teachings of which are incorporated herein by reference in their entirety. The cysteine rich region of wild-type NPP1 (i.e., PSCAKE through NEPQCP; the amino acid sequence from P99 to P204 of SEQ ID NO:1) can be employed to facilitates dimerization of the TAGNPP1 fusion proteins.

In another embodiment, the polyethylene glycol (PEG) can be conjugated to the TAGNPP1 fusion proteins. Other polypeptides may be selected so as to minimize aggregation and immunogenicity, to increase the solubility of the protein, or to enable the protein to be targeted to desired sites of clinical or biological importance.

TAGNPP1 can be also fused or conjugated to an appropriate polypeptide linker or other sequence for ease of identification, synthesis, or purification of the fusion protein, or to better preserve the native structure of the NPP1 component which can enhance the activity and targeting of the TAGNPP1. Specifically, a peptide linker sequence can be employed to separate the first and the second polypeptide components by a distance sufficient to ensure that each polypeptide folds into its secondary and tertiary structures. Such a peptide linker sequence is incorporated into the fusion protein between the NPP1 component and the TAG component using standard techniques well known in the art. Suitable peptide linker sequences may be chosen based on their ability to adopt a flexible extended conformation and their inability to adopt a secondary structure that could interact with functional portion on the NPP1, TAG or other secondary polypeptides described herein (e.g., Fc). Preferred peptide linker sequences contain Gly, His, Asn and Ser residues. The useful peptide linkers include, without limitation, poly-Gly, poly-His, poly-Asn, or poly-Ser. Other near neutral amino acids, such as Thr and Ala can be also used in the linker sequence Amino acid sequences which can be usefully employed as linkers include those disclosed in Maratea et al., Gene 40:39-46, 1985; Murphy et al., *Proc. Natl. Acad Sci. USA* 83:8258-8262, 1986; U.S. Pat. No. 4,935,233 and U.S. Pat. No. 4,751,180. The linker sequence may be from 1 to about 20 amino acid residues in length. Preferably, the polypeptide linker is between about 8 and about 12 amino acids in length. In a preferred embodiment, the peptide linker used in the invention is GGGGSGGGGS (SEQ ID NO:15), although any functional combination of Gly, Ser, His, or Asn can be employed.

Fusion proteins can also comprise a TAGNPP1 of the present invention together with an unrelated polypeptide. Preferably the unrelated polypeptide is capable of enhancing the targeting of the fusion protein to the site of clinical or biological importance (e.g., site of calcification). For example, peptides that have high affinity to the bone are described in U.S. Pat. No. 7,323,542, the entire teachings of which are incorporated herein by reference.

TAGNPP1 can be prepared using standard methods, including recombinant techniques or chemical conjugation well known in the art. Techniques useful for isolating and characterizing the nucleic acids and proteins of the present invention are well known to those of skill in the art and standard molecular biology and biochemical manuals can be consulted to select suitable protocols for use without undue experimentation. See, for example, Sambrook et al, 1989, "Molecular Cloning: A Laboratory Manual," 2nd ed., Cold Spring Harbor, the content of which is herein incorporated by reference in its entirety. Briefly, DNA sequences encoding the polypeptide components can be assembled separately, and ligated into an appropriate expression vector. For example, the 3' end of the DNA sequence encoding the NPP1 component is ligated, with or without a peptide linker, to the 5' end of a DNA sequence encoding the second polypeptide component such as TAG PEG, or Fc so that the reading frames of the sequences are in phase. This permits translation into a single fusion protein that retains the biological activity of both component polypeptides. The ligated DNA sequences are operably linked to suitable transcriptional or translational regulatory elements including a promoter. The regulatory elements responsible for expression of DNA are located only 5' to the DNA sequence encoding the first polypeptide such as the leader sequence encoding a signal peptide. Similarly, stop codons required to end translation and transcription termination signals are only present 3' to the DNA sequence encoding the second polypeptide.

The invention also encompasses TAGNPP1 variants. A preferred TAGNPP1 variant is one having 80%, 85%, 90%, 95% and more preferably 96% amino acid sequence identity to the amino acid sequence A205 through L591 of SEQ ID NO:1. A most preferred TAGNPP1 variant is one having at least 97% amino acid sequence identity to amino acid sequence A205 through L591 of SEQ ID NO:1.

The invention also relates to a polynucleotide sequence comprising the complement of SEQ ID NO:2 or variants thereof. In addition, the present invention also features polynucleotide sequences which hybridize under stringent conditions to SEQ ID NO:2 and whose the antisense sequence is 85%, 90%, 95%, 97%, 98%, or 99% identical to SEQ ID NO:2. Hybridization conditions are based on the melting temperature (Tm) of the nucleic acid binding complex or probe, as taught in Wahl, G. M. and S. L. Berger (1987; *Methods Enzymol.* 152:399-407) and Kimmel, A. R. (1987; *Methods Enzymol.* 152:507-511), and can be used at a defined stringency.

The invention additionally contemplates nucleic acid sequences encoding polypeptides, oligonucleotides, peptide nucleic acids (PNA), fragments, portions or antisense molecules thereof.

Although nucleotide sequences which encode TAGNPP1 and its variants are preferably capable of hybridizing to the nucleotide sequence of the TAGNPP1 under appropriately selected conditions of stringency, it can be advantageous to produce nucleotide sequences encoding TAGNPP1 or its derivatives possessing a substantially different codon usage. Codons can be selected to increase the rate at which expression of the peptide occurs in a particular prokaryotic or eukaryotic host in accordance with the frequency with which particular codons are utilized by the host. Other reasons for substantially altering the nucleotide sequence encoding TAGNPP1 and its derivatives without altering the encoded amino acid sequences include the production of RNA transcripts having more desirable properties, such as a greater half-life.

Altered nucleic acid sequences encoding TAGNPP1 which are encompassed by the invention include deletions, insertions, or substitutions of different nucleotides resulting in a polynucleotide that encodes the same or a functionally equivalent of TAGNPP1. The encoded protein can also contain deletions, insertions, or substitutions of amino acid residues which produce a silent change and result in a functionally equivalent TAGNPP1. Deliberate amino acid substitutions can be made on the basis of similarity in polarity, charge, solubility, hydrophobicity, hydrophilicity, and/or the amphipathic nature of the residues as long as the biological activity of TAGNPP1 is retained. For example, positively charged amino acid residues include Lys and Arg; negatively charged amino acid residues include Asp and Glu; and amino acids with uncharged polar head groups having similar hydrophilicity can include Leu, Ile, and Val; Gly and Ala; Asp and Gln; Ser and Thr; Phe and Tyr.

Expression Vector

Methods which are well known to those skilled in the art can be used to construct expression vectors containing sequences encoding TAGNPP1 and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y., the teachings of which are incorporated herein by reference in its entirety.

A variety of expression vector/host systems can be utilized to contain and express sequences encoding TAGNPP1. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus) or with bacterial expression vectors (e.g., Ti or pBR322 plasmids); or animal cell systems (e.g., pTT22 vector).

The control elements or regulatory sequences can includes those non-translated regions of the vector-enhancers, promoters, 5' and 3' untranslated regions-which interact with host cellular proteins to carry out transcription and translation. Such elements can vary in their strength and specificity. Depending on the vector system and host utilized, any number of suitable transcription and translation elements, including, tissue-specific, constitutive and inducible promoters, can be used. For example, when cloning in bacterial systems, inducible promoters such as the hybrid lacZ promoter of the Bluescript™ phagemid (Stratagene, LaJolla, Calif.) or pSport1™ plasmid (Gibco BRL) and the like can be used. In mammalian cell systems, promoters from mammalian genes or from mammalian viruses are preferred. If it is necessary to generate a cell line that contains multiple copies of the sequence encoding TAGNPP1, vectors based on SV40 or EBV can be used with an appropriate selectable marker. When an avian expression system is used, suitable vectors for expression various TAGNPP1 constructs are described in U.S. Pat. No. 6,730,822; U.S. Pat. No. 6,825,396; U.S. Pat. No. 6,875,588; U.S. Pat. No. 7,294,507; U.S. Pat. No. 7,521,591; U.S. Pat. No. 7,534,929; and U.S. patent application Ser. No. 11/376,023, the entire teachings of which are incorporated herein by reference in their entirety. Briefly, when an avian expression system is employed to express TAGNPP1, suitable oviduct-specific promoters, for example, and without limitation, ovomucoid promoters, ovalbumin promoters, lysozyme promoters, conalbumin promoters, ovomucin promoters, ovotransferrin promoters and functional portions of each of these promoters are contemplated. Suitable non-specific promoters can include, for example and without limitation, cytomegalovirus (CMV) promoters, MDOT promoters and rous-sarcoma virus (RSV) promoters, murine leukemia virus (MLV) promoters, mouse mammary tumor virus (MMTV) promoters and SV40 promoters and functional portions of each of these promoters. Non-limiting examples of other promoters which can be useful in the present invention include, without limitation, Pol III promoters (for example, type 1, type 2 and type 3 Pol III promoters) such as H1 promoters, U6 promoters, tRNA promoters, RNase MPR promoters and functional portions of each of these promoters. Typically, functional terminator sequences are selected for use in the present invention in accordance with the promoter that is employed.

Host Cells

The present invention includes the production of soluble TAGNPP1 in a transgenic avian (e.g., transgenic chicken) system as is well known in the art, for example, in U.S. Pat. No. 7,534,929, the disclosure of which is incorporated in its entirety herein by reference. Production in the avian system (e.g., in the avian oviduct) of an NPP1 component with or without to a targeting moiety (e.g., ssNPP1, sNPP1, TAG-sNPP1 and TAGssNPP1) is within the scope of the invention. Furthermore, TAGNPP1 produced in any useful protein expression system including, without limitation, transgenic avians, transgenic mammal, cell culture (e.g., CHO cells, HEK293 cells, and COS cells), bacteria such as *E. coli*, transgenic animals such as mammals and avians (e.g., chickens, quail, duck and turkey) and in plant systems including duck weed, is contemplated herein.

A host cell strain can be chosen for its ability to modulate the expression of the inserted sequences or to process the expressed TAGNPP1s in the desired fashion. Such modifications of the polypeptide of TAGNNP1 include, without limitation, acetylation, carboxylation, sialylation, glycosylation, phosphorylation, lipidation, and acylation. Different host cells such as CHO, COS, HeLa, MDCK, HEK293, and W138, which have specific cellular machinery and characteristic mechanisms for such post-translational activities, can be chosen to ensure the correct modification and processing of the fusion protein of the present invention. Avian tumor cell line is also contemplated as a host cell for expressing the polypeptide of the present invention. Examples of useful avian cell lines (e.g., an avian oviduct tumor cell line) which can be employed in the present invention are described in U.S. Pat. Publication No. 2009/0253176, the entire teachings of which are incorporated herein by reference.

Production of TAGNPP1

TAGNPP1 can be produced using any of a variety of well-known techniques. TAGNPP1 encoded by DNA sequences as described above can be readily prepared from the DNA sequences using any of a variety of expression vectors described herein or well known to those of ordinary skill in the art. Expression can be achieved in any appropriate host cell that has been transformed or transfected with an expression vector containing a DNA molecule that encodes a recombinant polypeptide of the present invention. Supernatants from suitable host/vector systems which secrete recombinant fusion protein or polypeptide into culture media can be first concentrated using a commercially available filter. Following concentration, the concentrate can be applied to a suitable purification matrix such as an affinity matrix or an ion exchange resin. One or more reverse phase HPLC steps can be employed to further purify a recombinant polypeptide.

For high-yield production of recombinant proteins, stable expression is preferred. Cell lines stably expressing TAGNPP1 can be transformed using expression vectors which contain viral origins of replication and/or endogenous expression elements and/or a selectable marker gene on the same or on a separate vector. Following the introduction of the vector, cells can be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells can be proliferated using tissue culture techniques appropriate to the cell type. Methods of producing exogenous protein in mammalian cell lines are well known in the art. Illustrative examples of this and other aspects and embodiments of the present invention for the production of heterologous polypeptides such as TAGNPP1 fusion proteins in avian cells are fully disclosed in U.S. patent application Ser. No. 09/877,374, filed Jun. 8, 2001, published as U.S. 2002/0108132-A1 on Aug. 8, 2002, and U.S. patent application Ser. No. 10/251,364, filed Sep. 18, 2002, each of which are incorporated herein by reference in their entirety. Examples of producing exogenous proteins in avian tumor cell lines are also described in U.S. Pat. Publication No. 2009/0253176, the entire teachings of which are incorporated herein by reference in entirety.

The invention specifically contemplates the production of the TAGNPP1 proteins disclosed herein in a transgenic avian system. In one particularly useful embodiment, the invention is drawn to the production of TAGNPP1 which can be produced in the oviduct of a transgenic avian, such as a chicken, in accordance with the invention. Examples of producing exogenous proteins in transgenic avian expression system are also described in U.S. Pat. No. 6,730,822, the entire teachings of which are incorporated herein by reference in entirety. Briefly, a suitable avian vector described above that contains a nucleic acid sequence encoding a TAGNPP1 fusion protein, operably linked to a tissue-specific or constitutive promoter that drives expression of the encoding sequence in the chicken oviduct are introduced into chicken stage X embryonic cells. The transformed embryonic cells are incubated under conditions conducive to hatching live chicks. Live chicks are nurtured into a mature chimeric chicken which are mated with a non-transgenic chicken naturally or via artificial insemination. A transgenic chicken is identified by screening progeny for germ line incorporation of the protein encoding sequence. The transgenic progeny can be mated with another transgenic or a non-transgenic chicken to produce eggs containing the TAGNPP1 fusion protein. The TAGNPP1 is then isolated and purified by methods well known in the art. Accordingly, the invention provides recombinant TAGNPP1 fusion proteins that have been produced by transgenic avians.

Pharmaceutical Composition

The present invention also features pharmaceutical compositions comprising isolated and substantially purified TAGNPP1 or a pharmaceutically acceptable salt thereof. Pharmaceutical composition of the present invention can also include a pharmaceutically acceptable carrier or excipient therefor. Compositions comprising such carriers, including composite molecules, are formulated by well-known conventional methods (see, for example, Remington's Pharmaceutical Sciences, 14th Ed., Mack Publishing Co., Easton, Pa.), the entire teachings of which are incorporated herein by reference. The carrier may comprise a diluent. In one embodiment, the pharmaceutical carrier can be a liquid and the fusion protein may be in the form of a solution. The pharmaceutical carrier can be wax, fat, or alcohol. In another embodiment, the pharmaceutically acceptable carrier may be a solid in the form of a powder, a lyophilized powder, or a tablet. In one embodiment, the carrier may comprise a liposome or a microcapsule.

The pharmaceutical compositions can be in the form of a sterile lyophilized powder for injection upon reconstitution with a diluent. The diluent can be water for injection, bacteriostatic water for injection, or sterile saline. The lyophilized powder may be produced by freeze drying a solution of the fusion protein to produce the protein in dry form. As is known in the art, the lyophilized protein generally has increased stability and a longer shelf life than a liquid solution of the protein.

DEFINITIONS

As used herein, the term "acceptable" with respect to a formulation, composition or ingredient, as used herein, means having no persistent detrimental effect on the general health of the subject being treated.

As used herein, the term "administration" or "administering" refers to providing a fusion protein of the invention to a subject in need of treatment.

"Alterations," as used herein, comprise any alteration in the sequence of polynucleotides encoding TAGNPP1 including deletions, insertions, and point mutations that may be detected using hybridization assays.

The term "animal" is used herein to include all vertebrate animals, including avians and mammals such as rat, mouse and human. It also includes an individual animal in all stages of development, including embryonic and fetal stages.

Where "amino acid sequence" is recited herein to refer to an amino acid sequence of a fusion protein molecule, "amino acid sequence" and like terms, such as "polypeptide" or "protein" are not meant to limit the amino acid sequence to the complete amino acid sequence associated with the recited protein or polypeptide molecule.

The term "avian" as used herein refers to any species, subspecies or strain of organism of the taxonomic class ava, such as, but not limited to, such organisms as chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Ausstralorp, Minorca, Amrox, California Gray, Italian Partridge-colored), as well as strains of turkeys, pheasants, quails, duck, ostriches and other poultry commonly bred in commercial quantities.

The phrase "based on" or "derived from" as in a retroviral vector being based on or derived from a particular retrovirus or based on a nucleotide sequence of a particular retrovirus mean that the genome of the retroviral vector contains a substantial portion of the nucleotide sequence of the genome of the particular retrovirus. The substantial portion may be a particular gene or nucleotide sequence such as the nucleotide sequence encoding the gag, pol and/or env proteins or other structural or functional nucleotide sequence of the virus genome such as sequences encoding the LTRs or may be substantially the complete retrovirus genome, for example, most (e.g., more than 60% or more than 70% or more than 80% or more than 90%) or all of the retrovirus genome, as will be apparent from the context in the specification as the knowledge of one skilled in the art. Examples of retroviral vectors that are based on or derived from a retrovirus are the NL retroviral vectors (e.g., NLB) which are based on the ALV retrovirus as disclosed in Cosset et al., *Journal of Virology* (1991) vol 65, p 3388-3394.

The term "biologically active," as used herein, refers to a fusion protein having structural, regulatory, or biochemical functions of pyrophosphatase/phosphodiesterase of a naturally occurring NPP1 protein.

The term "construct," as used herein, refers to a linear or circular nucleotide sequence such as DNA that has been assembled from more than one segments of nucleotide sequence which have been isolated from a natural source or have been chemically synthesized, or combinations thereof.

The term "complementary," as used herein, refers to two nucleic acid molecules that can form specific interactions with one another. In the specific interactions, an adenine base within one strand of a nucleic acid can form two hydrogen bonds with thymine within a second nucleic acid strand when the two nucleic acid strands are in opposing polarities. Also in the specific interactions, a guanine base within one strand of a nucleic acid can form three hydrogen bonds with cytosine within a second nucleic acid strand when the two nucleic acid strands are in opposing polarities. Complementary nucleic acids as referred to herein, may further comprise modified bases wherein a modified adenine may form hydrogen bonds with a thymine or modified thymine, and a modified cytosine may form hydrogen bonds with a guanine or a modified guanine.

A "deletion," as used herein, refers to a change in either amino acid or nucleotide sequence in which one or more amino acid or nucleotide residues, respectively, are absent.

The term "expressed" or "expression" as used herein refers to the transcription from a gene to give an RNA nucleic acid molecule at least complementary in part to a region of one of the two nucleic acid strands of the gene. The term "expressed" or "expression" as used herein can also refer to the translation of RNA to produce a protein or peptide.

The term "expression vector" as used herein refers to a nucleic acid vector that comprises a gene expression controlling region, such as a promoter or promoter component, operably linked to a nucleotide sequence coding at least one polypeptide.

"Functional portion" or "functional fragment" are used interchangeably and as used herein means a portion or fragment of a whole capable of performing, in whole or in part, a function of the whole. For example, a biologically functional portion of a molecule means a portion of the molecule that performs a biological function of the whole or intact molecule. For example, a functional portion of a gene expression controlling region is a fragment or portion of the specified gene expression controlling region that, in whole or in part, regulates or controls gene expression (e.g., facilitates either in whole or in part) in a biological system (e.g., a promoter). Functional portions may be of any useful size.

The term "gene expression controlling region" as used herein refers to nucleotide sequences that are associated with a coding sequence and which regulate, in whole or in part, expression of the coding sequence, for example, regulate, in whole or in part, the transcription of the coding sequence. Gene expression controlling regions may be isolated from a naturally occurring source or may be chemically synthesized and can be incorporated into a nucleic acid vector to enable regulated transcription in appropriate cells. The "gene expression controlling regions" may precede, but is not limited to preceding, the region of a nucleic acid sequence that is in the region 5' of the end of a coding sequence that may be transcribed into mRNA.

The terms "heterologous," "exogenous" and "foreign" are used interchangeably herein and in general refer to a biomolecule such as a nucleic acid or a protein that is not normally found in a certain organism or in a certain cell, tissue or other component contained in or produced by an organism. For example, a protein that is heterologous or exogenous to an egg is a protein that is not normally found in the egg. As used herein, the terms "heterologous," "exogenous" and "foreign" with reference to nucleic acids, such as DNA and RNA, are used interchangeably and refer to nucleic acid that does not occur naturally as part of a chromosome, a genome or cell in which it is present or which is found in a location(s) and/or in amounts that differ from the location(s) and/or amounts in which it occurs in nature. It can be nucleic acid that is not endogenous to the genome, chromosome or cell and has been exogenously introduced into the genome, chromosome or cell. Examples of heterologous DNA include, but are not limited to, a DNA comprising a gene expression control region and DNA that encodes a product or products, for example, RNA or protein product. Examples of heterologous DNA include, but are not limited to, gene expression controlling regions or promoters disclosed herein once isolated from the avian and as used thereafter, e.g., after re-introduction into an avian genome.

The term "isolated nucleic acid" as used herein covers, for example, (a) a DNA which has the sequence of part of a naturally occurring genomic molecule but is not flanked by at least one of the sequences that flank that part of the molecule in the genome of the species in which it naturally occurs; (b) a nucleic acid which has been incorporated into a vector or into the genomic DNA of a prokaryote or eukaryote in a manner such that the resulting vector or genomic DNA is not identical to naturally occurring DNA from which the nucleic acid was obtained; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions.

An "insertion" or "addition," as used herein, refers to a change in an amino acid or nucleotide sequence resulting in the addition of one or more amino acid or nucleotide residues, respectively, as compared to the TAGNPP1 molecule.

The term "nucleic acid" as used herein refers to any linear or sequential array of nucleotides and nucleosides, for example cDNA, genomic DNA, mRNA, tRNA, oligonucleotides, oligonucleosides and derivatives thereof. For ease of discussion, non-naturally occurring nucleic acids may be referred to herein as constructs. Nucleic acids can include bacterial plasmid vectors including expression, cloning, cosmid and transformation vectors such as, animal viral vectors such as, but not limited to, modified adenovirus, influenza virus, polio virus, pox virus, retroviruses such as avian leukosis virus (ALV) retroviral vector, a murine leukemia virus (MLV) retroviral vector, and a lentivirus vector, and the like and fragments thereof. In addition, the nucleic acid can be an LTR of an avian leukosis virus (ALV) retroviral vector, a murine leukemia virus (MLV) retroviral vector, or a lentivirus vector and fragments thereof. Nucleic acids can also include NL vectors such as NLB, NLD and NLA and fragments thereof and synthetic oligonucleotides such as chemically synthesized DNA or RNA. Nucleic acids can include modified or derivatised nucleotides and nucleosides such as, but not limited to, halogenated nucleotides such as, but not only, 5-bromouracil, and derivatised nucleotides such as biotin-labeled nucleotides.

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand.

The term "operably linked" refers to an arrangement of elements wherein the components so described are configured so as to perform their usual function. Gene expression controlling regions or promoters (e.g., promoter components) operably linked to a coding sequence are capable of effecting the expression of the coding sequence. The controlling sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "oviduct specific promoter" as used herein refers to promoters and promoter components which are functional, i.e., provide for transcription of a coding sequence, to a large extent, for example, primarily (i.e., more than 50% of the transcription product produced in the animal by a particular promoter type being produced in oviduct cells) or exclusively in oviduct cells of a bird. Examples of useful oviduct specific promoters include, without limitation, ovalbumin promoter, ovomucoid promoter, ovoinhibitor promoter, lysozyme promoter and ovotransferrin promoter and functional portions of these promoters, e.g., promoter components.

The terms "polynucleotide," "oligonucleotide," "nucleotide sequence" and "nucleic acid sequence" can be used interchangeably herein and include, but are not limited to, coding sequences, i.e., polynucleotide(s) or nucleic acid sequence(s) which are transcribed and translated into polypeptide in vitro or in vivo when placed under the control of appropriate regulatory or control sequences; controlling sequences, e.g., translational start and stop codons, promoter sequences, ribosome binding sites, polyadenylation signals, transcription factor binding sites, transcription termination sequences, upstream and downstream regulatory domains, enhancers, silencers, DNA sequences to which a transcription factor(s) binds and alters the activity of a gene's promoter either positively (induction) or negatively (repression) and the like. No limitation as to length or to synthetic origin are suggested by the terms described herein.

As used herein, the terms "polypeptide" and "protein" can be used interchangeably and refer to a polymer of amino acids of three or more amino acids in a serial array, linked through peptide bonds. The term "polypeptide" includes proteins such as fusion proteins, protein fragments, protein analogues, oligopeptides and the like. The term "polypeptides" includes polypeptides as defined above that are encoded by nucleic acids, produced through recombinant technology (e.g., isolated from a transgenic bird), or chemically synthesized.

As used herein, the term "promoter" refers to a DNA sequence useful to initiate transcription initiation by an RNA polymerase in an avian cell. A "promoter component" is a DNA sequence that can, by itself or, in combination with other DNA sequences effect or facilitate transcription. Specific promoter components such as ovalbumin promoter components, ovomucoid promoter components and lysozyme promoter components and other promoters and promoter components disclosed and claimed herein do not describe a specific promoter sequence. Rather, they encompass any sequence or sequence fragment of the respective promoter that is useful to effect or facilitate transcription of a coding sequence. For example, an ovomucoid promoter component includes, without limitation, the about 1.8 kb, the about 3.9 kb and the about 10 kb ovomucoid promoters disclosed in U.S. Publication Ser. No. 11/649,543, published May 17, 2007, which is incorporated in its entirety herein by reference. "Promoter components" can also encompass rearranged gene expression controlling regions which function to initiate RNA transcription and hybrid DNA molecules composed of naturally occurring DNA sequences and/or synthetic DNA sequences which function to initiate RNA transcription.

The terms "recombinant nucleic acid" and "recombinant DNA" as used herein refer to combinations of at least two nucleic acid sequences that are not naturally found in a eukaryotic or prokaryotic cell. The nucleic acid sequences may include, but are not limited to, nucleic acid vectors, gene expression regulatory elements, origins of replication, suitable gene sequences that when expressed confer antibiotic resistance, protein-encoding sequences and the like. The term "recombinant polypeptide" or "recombinant protein" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

The term "stringent conditions," as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

A "substitution," as used herein, refers to the replacement of one or more amino acids or nucleotides by different amino acids or nucleotides, respectively.

As used herein, the term "therapeutically effective amount" refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the terms "TAGNPP1," "fusion protein," "TAGNPP1 polypeptide" and "NPP1 component fused to a targeting moiety" are used interchangeably.

As used herein, the term "treat," "treating" or "treatment" refers to methods of alleviating, abating or ameliorating a disease or condition symptoms, preventing additional symptoms, ameliorating or preventing the underlying causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

A "variant" of TAGNPP1, as used herein, refers to an amino acid sequence that is altered by one or more amino acids. Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged Amino acid substitutions may generally be made on the basis of similarity in polarity, charge, solubility, hydrophobicity, hydrophilicity and/or the amphipathic nature of the residues. For example, negatively charged amino acids include Asp and Glu; positively charged amino acids include lysine and arginine; and amino acids with uncharged polar head groups having similar hydrophilicity values include Leu, Ile and Val; Gly and Ala; Asp and Gln; and Ser, Thr, Phe and Tyr. Other groups of amino acids that may represent conservative changes include: Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; and (5) Phe, Tyr, Trp, His. A variant may also, or alternatively, contain nonconservative changes. In a preferred embodiment, variant polypeptides differ from a native sequence by substitution, deletion or addition of five amino acids or fewer, or by, for example, replacement of a Gly with a Trp. Variants may also (or alternatively) be modified by, for example, the deletion or addition of amino acids that have minimal influence on the immunogenicity, secondary structure and hydropathic nature of the NPP1 component. Guidance in determining which amino acid residues can be substituted, inserted, or deleted without abolishing biological or immunological activity can be found using computer programs well known in the art.

The term "vector" and "nucleic acid vector" as used herein refers to a natural or synthetic single or double stranded plasmid or viral nucleic acid molecule that can be transfected or transformed into cells and replicate independently of, or within, the host cell genome. A circular double stranded vector can be linearized by treatment with an appropriate restriction enzyme based on the nucleotide sequence of the vector. A nucleic acid can be inserted into a vector by cutting the vector with restriction enzymes and ligating the desired pieces together.

The term "portion," as used herein, with regard to a fusion protein refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length TAGNPP1 and fragments thereof.

"Transformation" or "transfection," as used herein, describes a process by which exogenous DNA enters and changes a recipient cell using various methods well known in the art. Transformation may rely on any known method for the insertion of foreign nucleic acid sequences into a prokaryotic or eukaryotic host cell. The method is selected based on the host cell being transformed and may include, but is not limited to, electroporation, particle bombardment, viral infection, and lipofection. Such "transformed" cells include stably transformed cells in which the inserted DNA is capable of replicating either as an autonomously replicating plasmid or as part of the host chromosome. They also include cells which transiently express the inserted DNA or RNA for limited periods of time.

EXAMPLES

The present invention is further exemplified by the following examples. The examples are for illustrative purpose only and are not intended, nor should they be construed as limiting the invention in any manner.

Example I

Figure 21:
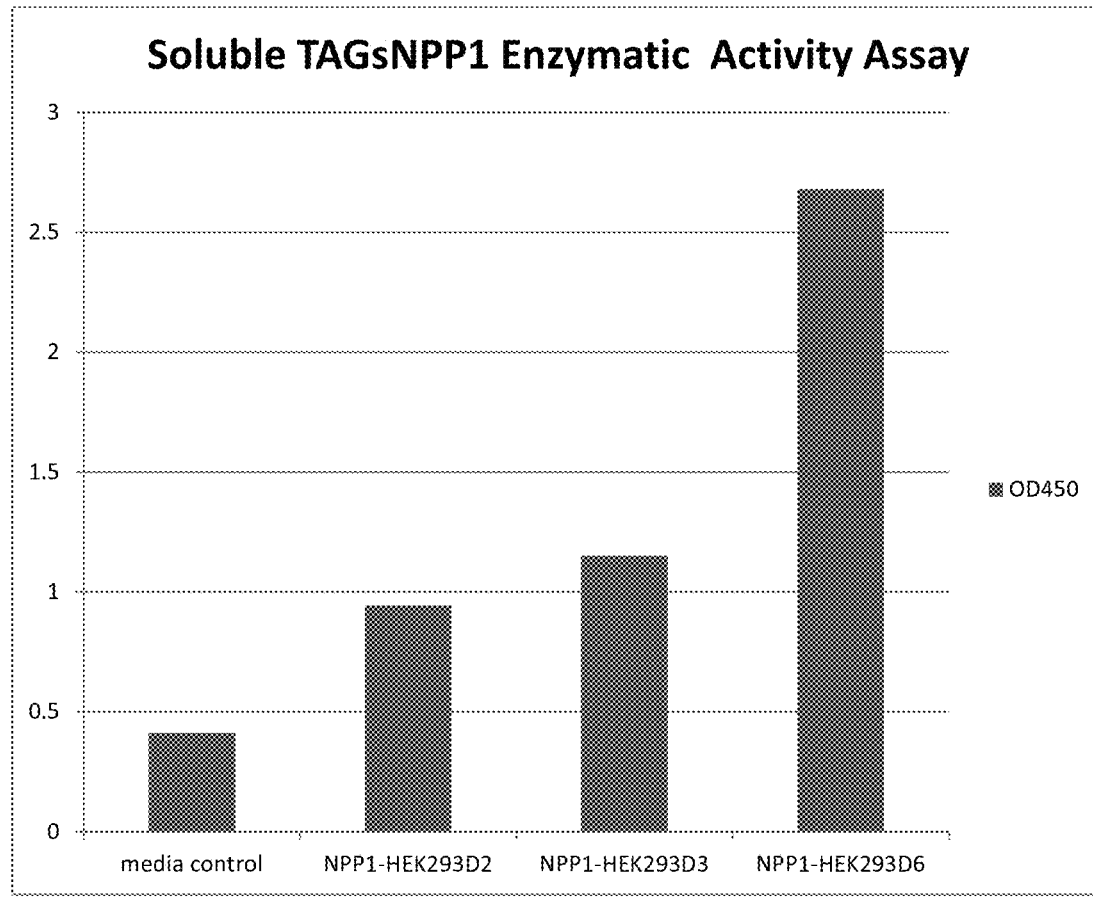
FIG. 21 demonstrates the enzymatic activity of TAG-sNPP1 produced and isolated from HEK293 cells.
Figure 22A:
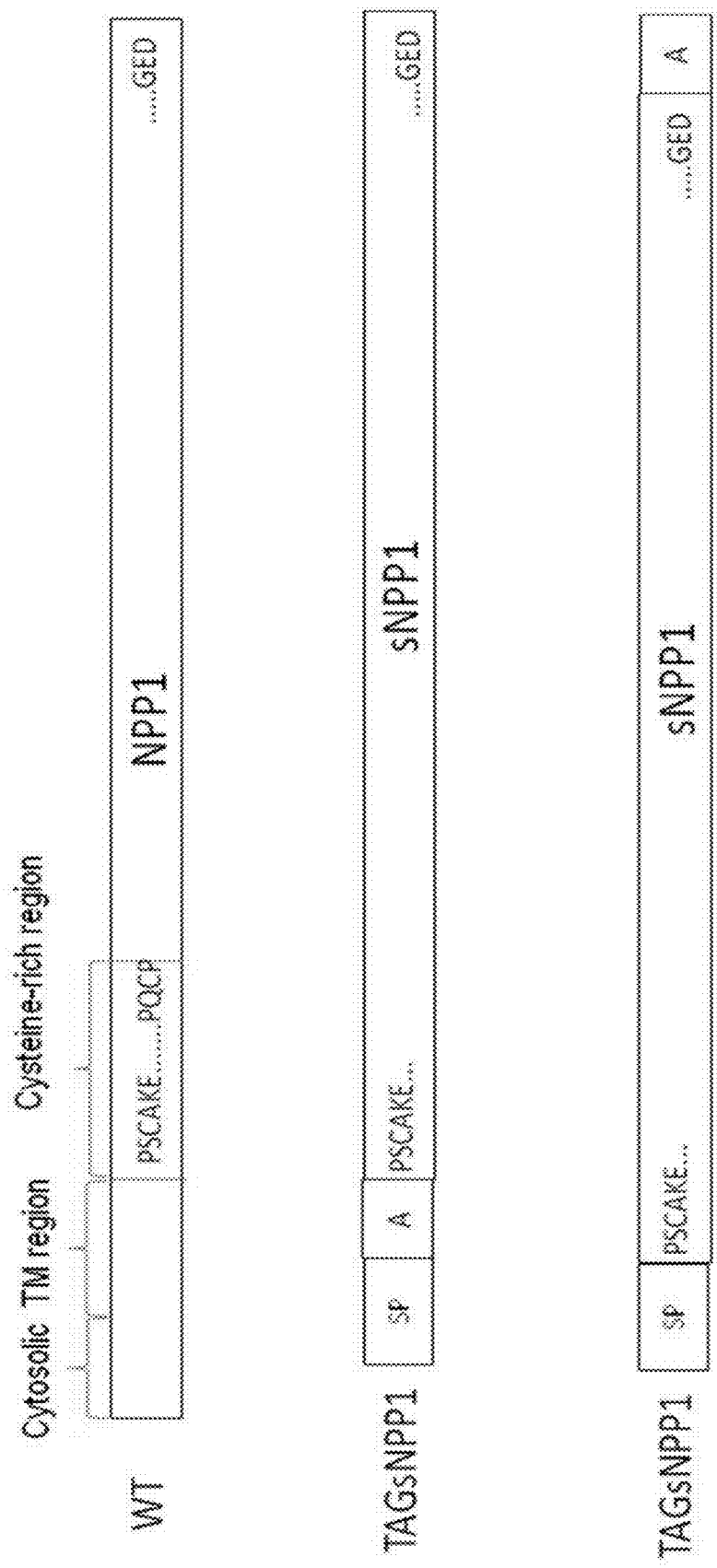

The TAGsNNP1 construct containing the targeting moiety having eight consecutive aspartic acids fused to sNPP1 was ligated into pTT22 vector using EcoRI and HindIII sites (pTT22-sNPP1.D8; FIG. 19). pTT22-sNPP1.D8 was transfected into HEK203E cells and the transformants were cultured to express TAGsNNP1. TAGsNNP1 was isolated from the culture media and partially purified as well known in the art. Following the purification, the pyrophosphase/phosphodiesterase activity of TAGsNPP1 was measured for its ability to hydrolyze thymmidine 5' monophosphate p-nitrophenyl ester. Briefly, TAGsNPP1 was diluted to 1 ng/µL in 50 mM Tris, 250 mM NaCl, pH 9.5. In a plate containing 50 µL of 1 ng/µL TAGsNPP1, 50 µL of 10 mM thymmidine 5' monophosphate p-nitrophenyl ester (Sigma™, Catalog #T4510) substrate was added. The enzyme activity of TAGsNPP1 was measured at 405 nm (absorbance) in kinetic mode for 5 minutes. As shown in FIG. 21, the activity of TAGsNPP1 was detected above the level observed in control containing no TAGsNPP1. Particularly, TAGsNPP1 produced from HEK203D6 exhibited the highest level of the enzymatic activity. This results strongly suggested that the truncated NPP1 fused to a targeting moiety (i.e., D8) sufficiently maintained its normal function as nuclease.

Example II

This non-limiting prophetic example describes how to treat idiopathic infantile arterial calcification by administering a formulation comprising a TAGNPP1 fusion protein.

A clinician uses a diagnostic test to verify that a patient has high levels of calcification in the artery. A genetic test can be also performed for NPP1 defects as described in Rutsch et al. (2003), *Nature Genetics* 34:379-81.

The pharmaceutical compositions of the present invention are preferably administered intravenously, although interadermal, intramuscular or oral administration are employed in certain circumstances.

The clinician determines a dose which may vary depending on the gender, age, health, and weight of the patient. The determination of the appropriate dosage or route of administration is well within the skill of an ordinary physician.

The formulation containing TAGNPP1 can be infused, between about 10 mg/kg and about 1000 mg/kg per week weekly. 10-30 mg/kg can be administered once. During the infusion period, patients are monitored closely and appropriate clinical intervention is taken in the event of an adverse event. Treatment lasts at least 1 month or for the life of the patient. A window of 48 hours may be allowed for each infusion. An infusion schedule in which the rate of infusion increases with time reduces or eliminates adverse events. Infusions for infants can be administered according to the following schedule: 5-10 cc/hr for 60 minutes in each interval.

On the other hand, when continuous intravenous administration is desired, typical example of the slow release systems comprises that 1-100 mg/kg of effective TAGNPP1 proteins can be continuously released for more than 1 day.

While this invention has been particularly shown and described with references to example embodiments thereof, it will be understood by those skilled in the art that various changes in form and details may be made therein without departing from the scope of the invention encompassed by the appended claims.

What is claimed is:

1. A recombinant nucleic acid that encodes a NPP1 fusion protein, wherein the NPP1 fusion protein comprises an NPP1 component, a targeting moiety, and an Fc region of an immunoglobulin, wherein a) the NPP1 component comprises the cysteine-rich region and the C-terminus catalytic domain of NPP1, b) the targeting moiety and the Fc region are each located C-terminally to the NPP1 component, and c) the NPP1 fusion protein has NPP1 enzymatic activity.

2. The recombinant nucleic acid of claim 1, wherein said NPP1 enzymatic activity is pyrophosphatase activity, phosphodiesterase activity or pyrophosphatase and phosphodiesterase activity.

3. The recombinant nucleic acid of claim 1, wherein said NPP1 component consists of P99 through D925 of SEQ ID NO: 1.

4. The recombinant nucleic acid of claim 3, wherein said targeting moiety is a peptide comprising at least four negatively charged amino acid residues.

5. The recombinant nucleic acid of claim 3, wherein said targeting moiety is a peptide comprising between about five and about fifteen negatively charged amino acid residues.

6. The recombinant nucleic acid of claim 5, wherein said negatively charged amino acid residues comprise about eight consecutive aspartic acid or glutamic acid residues.

7. The recombinant nucleic acid of claim 5, wherein said negatively charged amino acid residues comprise at least four aspartic acid residues.

8. The recombinant nucleic acid of claim 5, wherein said negatively charged amino acid residues comprise at least four glutamic acid residues.

9. The recombinant nucleic acid of claim 5, wherein said negatively charged amino acid residues comprise eight consecutive aspartic acid residues.

10. The recombinant nucleic acid of claim 3, wherein said targeting moiety is fused to the C-terminus of said catalytic domain of NPP1.

11. The recombinant nucleic acid of claim 3, wherein said Fc region is fused to the C-terminus of said catalytic domain of NPP1.

12. The recombinant nucleic acid of claim 1, wherein said fusion protein further comprises a polypeptide linker between said targeting moiety and said catalytic domain of NPP1.

13. The recombinant nucleic acid of claim 1, wherein said recombinant nucleic acid further encodes a signal peptide at the N-terminus of the fusion protein.

14. The recombinant nucleic acid of claim 1, wherein said fusion protein forms a homodimer.

15. The recombinant nucleic acid of claim 1, wherein said fusion protein is a monomer.

16. The recombinant nucleic acid of claim 1, wherein the recombinant nucleic acid is an expression vector.

* * * * *

SEQUENCE LISTING

```
<160> NUMBER OF SEQ ID NOS: 18

<210> SEQ ID NO 1
<211> LENGTH: 925
<212> TYPE: PRT
<213> ORGANISM: Homo sapiens

<400> SEQUENCE: 1

Met Glu Arg Asp Gly Cys Ala Gly Gly Ser Arg Gly Gly Glu Gly
1               5                   10                  15

Gly Arg Ala Pro Arg Glu Gly Pro Ala Gly Asn Gly Arg Asp Arg Gly
            20                  25                  30

Arg Ser His Ala Ala Glu Ala Pro Gly Asp Pro Gln Ala Ala Ala Ser
            35                  40                  45

Leu Leu Ala Pro Met Asp Val Gly Glu Glu Pro Leu Glu Lys Ala Ala
            50                  55                  60

Arg Ala Arg Thr Ala Lys Asp Pro Asn Thr Tyr Lys Val Leu Ser Leu
65                  70                  75                  80

Val Leu Ser Val Cys Val Leu Thr Thr Ile Leu Gly Cys Ile Phe Gly
                    85                  90                  95

Leu Lys Pro Ser Cys Ala Lys Glu Val Lys Ser Cys Lys Gly Arg Cys
                    100                 105                 110

Phe Glu Arg Thr Phe Gly Asn Cys Arg Cys Asp Ala Ala Cys Val Glu
                    115                 120                 125

Leu Gly Asn Cys Cys Leu Asp Tyr Gln Glu Thr Cys Ile Glu Pro Glu
                    130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                    165                 170                 175

Cys Ile Asn Tyr Ser Ser Val Cys Gln Gly Glu Lys Ser Trp Val Glu
                    180                 185                 190

Glu Pro Cys Glu Ser Ile Asn Glu Pro Gln Cys Pro Ala Gly Phe Glu
                    195                 200                 205

Thr Pro Pro Thr Leu Leu Phe Ser Leu Asp Gly Phe Arg Ala Glu Tyr
            210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                    245                 250                 255
```

```
Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
            275                 280                 285

Ser Leu Lys Ser Lys Glu Lys Phe Asn Pro Gly Trp Tyr Lys Gly Glu
            290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                    325                 330                 335

Tyr Lys Met Tyr Asn Gly Ser Val Pro Phe Glu Arg Ile Leu Ala
            340                 345                 350

Val Leu Gln Trp Leu Gln Leu Pro Lys Asp Glu Arg Pro His Phe Tyr
            355                 360                 365

Thr Leu Tyr Leu Glu Glu Pro Asp Ser Ser Gly His Ser Tyr Gly Pro
            370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                    405                 410                 415

Asn Leu Ile Leu Ile Ser Asp His Gly Met Glu Gln Gly Ser Cys Lys
                    420                 425                 430

Lys Tyr Ile Tyr Leu Asn Lys Tyr Leu Gly Asp Val Lys Asn Ile Lys
            435                 440                 445

Val Ile Tyr Gly Pro Ala Ala Arg Leu Arg Pro Ser Asp Val Pro Asp
            450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                    485                 490                 495

Lys Arg Leu His Phe Ala Lys Ser Asp Arg Ile Glu Pro Leu Thr Phe
                    500                 505                 510

Tyr Leu Asp Pro Gln Trp Gln Leu Ala Leu Asn Pro Ser Glu Arg Lys
            515                 520                 525

Tyr Cys Gly Ser Gly Phe His Gly Ser Asp Asn Val Phe Ser Asn Met
            530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                    565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
            595                 600                 605

His Pro Leu Val Gln Cys Pro Phe Thr Arg Asn Pro Arg Asp Asn Leu
            610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                    645                 650                 655

Leu Pro Tyr Gly Arg Pro Arg Val Leu Gln Lys Glu Asn Thr Ile Cys
                    660                 665                 670
```

-continued

Leu Leu Ser Gln His Gln Phe Met Ser Gly Tyr Ser Gln Asp Ile Leu
675                 680                 685

Met Pro Leu Trp Thr Ser Tyr Thr Val Asp Arg Asn Asp Ser Phe Ser
690                 695                 700

Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
            725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
            755                 760                 765

Phe Gln Val Ile Trp Arg Tyr Phe His Asp Thr Leu Leu Arg Lys Tyr
770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
            805                 810                 815

Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
            835                 840                 845

Glu Asn Leu Asp Thr Leu Ala Phe Ile Leu Pro His Arg Thr Asp Asn
850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
            885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp
            915                 920                 925

<210> SEQ ID NO 2
<211> LENGTH: 387
<212> TYPE: PRT
<213> ORGANISM: Artificial sequence
<220> FEATURE:
<223> OTHER INFORMATION: Synthetic

<400> SEQUENCE: 2

Ala Gly Phe Glu Thr Pro Pro Thr Leu Leu Phe Ser Leu Asp Gly Phe
1               5                   10                  15

Arg Ala Glu Tyr Leu His Thr Trp Gly Gly Leu Leu Pro Val Ile Ser
            20                  25                  30

Lys Leu Lys Lys Cys Gly Thr Tyr Thr Lys Asn Met Arg Pro Val Tyr
        35                  40                  45

Pro Thr Lys Thr Phe Pro Asn His Tyr Ser Ile Val Thr Gly Leu Tyr
    50                  55                  60

Pro Glu Ser His Gly Ile Ile Asp Asn Lys Met Tyr Asp Pro Lys Met
65                  70                  75                  80

Asn Ala Ser Phe Ser Leu Lys Ser Lys Glu Lys Phe Asn Pro Glu Trp
                85                  90                  95

Tyr Lys Gly Glu Pro Ile Trp Val Thr Ala Lys Tyr Gln Gly Leu Lys
            100                 105                 110

```
Ser Gly Thr Phe Phe Trp Pro Gly Ser Asp Val Glu Ile Asn Gly Ile
            115                 120                 125

Phe Pro Asp Ile Tyr Lys Met Tyr Asn Gly Ser Val Pro Phe Glu Glu
        130                 135                 140

Arg Ile Leu Ala Val Leu Gln Trp Leu Gln Leu Pro Lys Asp Glu Arg
145                 150                 155                 160

Pro His Phe Tyr Thr Leu Tyr Leu Glu Glu Pro Asp Ser Ser Gly His
                165                 170                 175

Ser Tyr Gly Pro Val Ser Ser Glu Val Ile Lys Ala Leu Gln Arg Val
            180                 185                 190

Asp Gly Met Val Gly Met Leu Met Asp Gly Leu Lys Glu Leu Asn Leu
        195                 200                 205

His Arg Cys Leu Asn Leu Ile Leu Ile Ser Asp His Gly Met Glu Gln
        210                 215                 220

Gly Ser Cys Lys Lys Tyr Ile Tyr Leu Asn Lys Tyr Leu Gly Asp Val
225                 230                 235                 240

Lys Asn Ile Lys Val Ile Tyr Gly Pro Ala Ala Arg Leu Arg Pro Ser
                245                 250                 255

Asp Val Pro Asp Lys Tyr Tyr Ser Phe Asn Tyr Glu Gly Ile Ala Arg
            260                 265                 270

Asn Leu Ser Cys Arg Glu Pro Asn Gln His Phe Lys Pro Tyr Leu Lys
        275                 280                 285

His Phe Leu Pro Lys Arg Leu His Phe Ala Lys Ser Asp Arg Ile Glu
        290                 295                 300

Pro Leu Thr Phe Tyr Leu Asp Pro Gln Trp Gln Leu Ala Leu Asn Pro
305                 310                 315                 320

Ser Glu Arg Lys Tyr Cys Gly Ser Gly Phe His Gly Ser Asp Asn Val
                325                 330                 335

Phe Ser Asn Met Gln Ala Leu Phe Val Gly Tyr Gly Pro Gly Phe Lys
            340                 345                 350

His Gly Ile Glu Ala Asp Thr Phe Glu Asn Ile Glu Val Tyr Asn Leu
        355                 360                 365

Met Cys Asp Leu Leu Asn Leu Thr Pro Ala Pro Asn Asn Gly Thr His
        370                 375                 380

Gly Ser Leu
385

<210> SEQ ID NO 3
<211> LENGTH: 420
<212> TYPE: PRT
<213> ORGANISM: Artificial sequence
<220> FEATURE:
<223> OTHER INFORMATION: Synthetic

<400> SEQUENCE: 3

Ile Gly Val Leu Leu Thr Gln Arg Thr Leu Leu Ser Leu Val Leu Ala
1               5                   10                  15

Leu Leu Phe Pro Ser Met Ala Ser Met Asp Asp Asp Asp Asp Asp Asp
            20                  25                  30

Asp Ala Gly Phe Glu Thr Pro Pro Thr Leu Phe Ser Leu Asp Gly
        35                  40                  45

Phe Arg Ala Glu Tyr Leu His Thr Trp Gly Gly Leu Leu Pro Val Ile
    50                  55                  60

Ser Lys Leu Lys Lys Cys Gly Thr Tyr Thr Lys Asn Met Arg Pro Val
65                  70                  75                  80
```

```
Tyr Pro Thr Lys Thr Phe Pro Asn His Tyr Ser Ile Val Thr Gly Leu
                85                  90                  95
Tyr Pro Glu Ser His Gly Ile Ile Asp Asn Lys Met Tyr Asp Pro Lys
            100                 105                 110
Met Asn Ala Ser Phe Ser Leu Lys Ser Lys Glu Lys Phe Asn Pro Glu
            115                 120                 125
Trp Tyr Lys Gly Glu Pro Ile Trp Val Thr Ala Lys Tyr Gln Gly Leu
130                 135                 140
Lys Ser Gly Thr Phe Phe Trp Pro Gly Ser Asp Val Glu Ile Asn Gly
145                 150                 155                 160
Ile Phe Pro Asp Ile Tyr Lys Met Tyr Asn Gly Ser Val Pro Phe Glu
                165                 170                 175
Glu Arg Ile Leu Ala Val Leu Gln Trp Leu Gln Leu Pro Lys Asp Glu
            180                 185                 190
Arg Pro His Phe Tyr Thr Leu Tyr Leu Glu Glu Pro Asp Ser Ser Gly
            195                 200                 205
His Ser Tyr Gly Pro Val Ser Ser Glu Val Ile Lys Ala Leu Gln Arg
            210                 215                 220
Val Asp Gly Met Val Gly Met Leu Met Asp Gly Leu Lys Glu Leu Asn
225                 230                 235                 240
Leu His Arg Cys Leu Asn Leu Ile Leu Ile Ser Asp His Gly Met Glu
                245                 250                 255
Gln Gly Ser Cys Lys Lys Tyr Ile Tyr Leu Asn Lys Tyr Leu Gly Asp
            260                 265                 270
Val Lys Asn Ile Lys Val Ile Tyr Gly Pro Ala Ala Arg Leu Arg Pro
            275                 280                 285
Ser Asp Val Pro Asp Lys Tyr Tyr Ser Phe Asn Tyr Glu Gly Ile Ala
            290                 295                 300
Arg Asn Leu Ser Cys Arg Glu Pro Asn Gln His Phe Lys Pro Tyr Leu
305                 310                 315                 320
Lys His Phe Leu Pro Lys Arg Leu His Phe Ala Lys Ser Asp Arg Ile
                325                 330                 335
Glu Pro Leu Thr Phe Tyr Leu Asp Pro Gln Trp Gln Leu Ala Leu Asn
            340                 345                 350
Pro Ser Glu Arg Lys Tyr Cys Gly Ser Gly Phe His Gly Ser Asp Asn
            355                 360                 365
Val Phe Ser Asn Met Gln Ala Leu Phe Val Gly Tyr Gly Pro Gly Phe
            370                 375                 380
Lys His Gly Ile Glu Ala Asp Thr Phe Glu Asn Ile Glu Val Tyr Asn
385                 390                 395                 400
Leu Met Cys Asp Leu Leu Asn Leu Thr Pro Ala Pro Asn Asn Gly Thr
                405                 410                 415
His Gly Ser Leu
            420

<210> SEQ ID NO 4
<211> LENGTH: 422
<212> TYPE: PRT
<213> ORGANISM: Artificial sequence
<220> FEATURE:
<223> OTHER INFORMATION: Synthetic

<400> SEQUENCE: 4

Ile Gly Val Leu Leu Thr Gln Arg Thr Leu Leu Ser Leu Val Leu Ala
1               5                   10                  15
```

```
Leu Leu Phe Pro Ser Met Ala Ser Met Ala Gly Phe Glu Thr Pro Pro
         20                  25                  30

Thr Leu Leu Phe Ser Leu Asp Gly Phe Arg Ala Glu Tyr Leu His Thr
         35                  40                  45

Trp Gly Gly Leu Leu Pro Val Ile Ser Lys Leu Lys Lys Cys Gly Thr
         50                  55                  60

Tyr Thr Lys Asn Met Arg Pro Val Tyr Pro Thr Lys Thr Phe Pro Asn
65                       70                  75                  80

His Tyr Ser Ile Val Thr Gly Leu Tyr Pro Glu Ser His Gly Ile Ile
                     85                  90                  95

Asp Asn Lys Met Tyr Asp Pro Lys Met Asn Ala Ser Phe Ser Leu Lys
             100                 105                 110

Ser Lys Glu Lys Phe Asn Pro Glu Trp Tyr Lys Gly Glu Pro Ile Trp
         115                 120                 125

Val Thr Ala Lys Tyr Gln Gly Leu Lys Ser Gly Thr Phe Phe Trp Pro
         130                 135                 140

Gly Ser Asp Val Glu Ile Asn Gly Ile Phe Pro Asp Ile Tyr Lys Met
145                 150                 155                 160

Tyr Asn Gly Ser Val Pro Phe Glu Glu Arg Ile Leu Ala Val Leu Gln
                 165                 170                 175

Trp Leu Gln Leu Pro Lys Asp Glu Arg Pro His Phe Tyr Thr Leu Tyr
             180                 185                 190

Leu Glu Glu Pro Asp Ser Ser Gly His Ser Tyr Gly Pro Val Ser Ser
         195                 200                 205

Glu Val Ile Lys Ala Leu Gln Arg Val Asp Gly Met Val Gly Met Leu
210                 215                 220

Met Asp Gly Leu Lys Glu Leu Asn Leu His Arg Cys Leu Asn Leu Ile
225                 230                 235                 240

Leu Ile Ser Asp His Gly Met Glu Gln Gly Ser Cys Lys Lys Tyr Ile
                 245                 250                 255

Tyr Leu Asn Lys Tyr Leu Gly Asp Val Lys Asn Ile Lys Val Ile Tyr
             260                 265                 270

Gly Pro Ala Ala Arg Leu Arg Pro Ser Asp Val Pro Asp Lys Tyr Tyr
         275                 280                 285

Ser Phe Asn Tyr Glu Gly Ile Ala Arg Asn Leu Ser Cys Arg Glu Pro
290                 295                 300

Asn Gln His Phe Lys Pro Tyr Leu Lys His Phe Leu Pro Lys Arg Leu
305                 310                 315                 320

His Phe Ala Lys Ser Asp Arg Ile Glu Pro Leu Thr Phe Tyr Leu Asp
                 325                 330                 335

Pro Gln Trp Gln Leu Ala Leu Asn Pro Ser Glu Arg Lys Tyr Cys Gly
             340                 345                 350

Ser Gly Phe His Gly Ser Asp Asn Val Phe Ser Asn Met Gln Ala Leu
         355                 360                 365

Phe Val Gly Tyr Gly Pro Gly Phe Lys His Gly Ile Glu Ala Asp Thr
         370                 375                 380

Phe Glu Asn Ile Glu Val Tyr Asn Leu Met Cys Asp Leu Leu Asn Leu
385                 390                 395                 400

Thr Pro Ala Pro Asn Asn Gly Thr His Gly Ser Leu Asp Asp Asp Asp
                 405                 410                 415

Asp Asp Asp Asp Asp Asp
                 420
```

<210> SEQ ID NO 5
<211> LENGTH: 2265
<212> TYPE: DNA
<213> ORGANISM: Artificial sequence
<220> FEATURE:
<223> OTHER INFORMATION: Synthetic

<400> SEQUENCE: 5

| | | | | | |
|---|---|---|---|---|---|
| atgggtgtac | tgctcacaca | gaggacgctg | ctcagtctgg | tccttgcact | cctgtttcca | 60 |
| agcatggcga | gcatggatga | cgatgatgac | gacgatgacg | cagggtttga | aacgcctcct | 120 |
| acactcttgt | tttctttgga | tggattcagg | gcagaatatt | tgcacacttg | gggtggactt | 180 |
| cttcctgtta | ttagcaaact | caaaaaatgt | ggaacatata | ctaaaaacat | gagaccggtg | 240 |
| tatccaacaa | aactttccc | caatcactac | agcattgtca | ccggattgta | tccagaatct | 300 |
| catggcataa | tcgacaataa | gatgtatgat | cccaaaatga | atgcttcctt | ttcacttaaa | 360 |
| agtaaagaga | atttaatcc | ggagtggtac | aaaggagaac | caatttgggt | cacagctaag | 420 |
| tatcaaggcc | tcaagtctgg | cacattttc | tggccaggat | cagatgtgga | aattaacgga | 480 |
| attttcccag | acatctataa | aatgtataat | ggttcagtgc | catttgaaga | aaggattttg | 540 |
| gctgttcttc | agtggctgca | gcttccaaaa | gatgaaagac | cacactttta | cactttgtat | 600 |
| ttggaagaac | cagattcttc | aggtcattca | tatggaccag | tcagcagtga | agtcatcaaa | 660 |
| gccttgcaga | gggttgatgg | tatggttggt | atgctgatgg | atggtctgaa | agagctgaac | 720 |
| ttgcacagat | gcctgaacct | catccttatt | tcagatcatg | gcatggaaca | aggcagttgt | 780 |
| aagaaataca | tatatctgaa | taagtatttg | ggggatgtta | aaaatattaa | agttatctat | 840 |
| ggacctgcag | ctcgattgag | accctctgat | gtcccagata | aatactattc | atttaactat | 900 |
| gaaggcattg | cccgaaatct | ttcttgccgg | gaaccaaacc | agcacttcaa | accttatctg | 960 |
| aaacatttct | tgcctaagcg | tttgcacttt | gctaagagtg | atagaattga | gcccttgaca | 1020 |
| ttctatttgg | accctcagtg | gcaacttgca | ttgaatccct | cagaaaggaa | atattgtgga | 1080 |
| agtggatttc | atggctctga | caatgtgttt | tcaaatatgc | aagccctctt | tgttggctat | 1140 |
| ggacctggat | tcaagcatgg | cattgaggct | gacacctttg | aaaacattga | agtctataac | 1200 |
| ttgatgtgtg | atttgctgaa | tttgacaccg | gctcctaata | acggaactca | tggaagtctt | 1260 |
| aaccaccttc | tgaagaatcc | tgtttatacg | ccaaagcatc | ccaaagaagt | gcacccctg | 1320 |
| gtgcagtgcc | ccttcacaag | aaaccccaga | gataaccttg | gctgctcatg | taaccccttcc | 1380 |
| attttgccga | ttgaggattt | tcaaacacag | ttcaatctga | ccgtggcaga | agagaagatt | 1440 |
| attaagcatg | aaactttgcc | ctatggaaga | cctagagttc | tccagaagga | aaacaccatc | 1500 |
| tgtcttcttt | cccagcacca | gtttatgagt | ggatacagcc | aagacatctt | gatgcccctt | 1560 |
| tggacatcct | ataccgtgga | cagaaatgac | agtttctcta | cggaagactt | ctccaactgt | 1620 |
| ctgtaccagg | actttagaat | tcctcttagt | cctgtccata | aatgttcatt | ttataaaaat | 1680 |
| aacaccaaag | tgagttacgg | gttcctctcc | ccaccacaac | tgaataagaa | ttcaagtgga | 1740 |
| atatattctg | aagccttgct | tactacaaat | atagtgccaa | tgtaccagag | ttttcaagtt | 1800 |
| atatggcgct | actttcatga | caccctcttg | cgaaagtatg | cagaagaaag | aaatggtgtc | 1860 |
| aatgtcgtca | gtggtcctgt | gtttgacttt | gattatgatg | acgttgtga | ttccttggag | 1920 |
| aatttgaggc | aaaaaagaag | agtcatccgt | aaccaagaaa | ttttgattcc | aactcatttc | 1980 |
| ttcattgtgc | tgacaagctg | taaagataca | tctcagacgc | ctttgcactg | tgaaaacctg | 2040 |
| gacaccttgg | ctttcatttt | gcctcacagg | actgataaca | gcgagagctg | tgtgcatggg | 2100 |

```
aagcatgact cctcatgggt tgaagaattg ttgatgttgc acagagcacg gatcacagac   2160
gtcgagcaca tcactggact cagctttat caacaaagaa aagagccagt ttcagacatt   2220
ttgaagttga aaacacattt gccaacctt agccaagaag attga                   2265
```

<210> SEQ ID NO 6
<211> LENGTH: 754
<212> TYPE: PRT
<213> ORGANISM: Artificial Sequence
<220> FEATURE:
<223> OTHER INFORMATION: Synthetic

<400> SEQUENCE: 6

```
Ile Gly Val Leu Leu Thr Gln Arg Thr Leu Leu Ser Leu Val Leu Ala
1               5                   10                  15

Leu Leu Phe Pro Ser Met Ala Ser Met Asp Asp Asp Asp Asp Asp Asp
                20                  25                  30

Asp Ala Gly Phe Glu Thr Pro Pro Thr Leu Leu Phe Ser Leu Asp Gly
            35                  40                  45

Phe Arg Ala Glu Tyr Leu His Thr Trp Gly Gly Leu Leu Pro Val Ile
    50                  55                  60

Ser Lys Leu Lys Lys Cys Gly Thr Tyr Thr Lys Asn Met Arg Pro Val
65                  70                  75                  80

Tyr Pro Thr Lys Thr Phe Pro Asn His Tyr Ser Ile Val Thr Gly Leu
                85                  90                  95

Tyr Pro Glu Ser His Gly Ile Ile Asp Asn Lys Met Tyr Asp Pro Lys
            100                 105                 110

Met Asn Ala Ser Phe Ser Leu Lys Ser Lys Lys Phe Asn Pro Glu
    115                 120                 125

Trp Tyr Lys Gly Glu Pro Ile Trp Val Thr Ala Lys Tyr Gln Gly Leu
130                 135                 140

Lys Ser Gly Thr Phe Phe Trp Pro Gly Ser Asp Val Glu Ile Asn Gly
145                 150                 155                 160

Ile Phe Pro Asp Ile Tyr Lys Met Tyr Asn Gly Ser Val Pro Phe Glu
                165                 170                 175

Glu Arg Ile Leu Ala Val Leu Gln Trp Leu Gln Leu Pro Lys Asp Glu
            180                 185                 190

Arg Pro His Phe Tyr Thr Leu Tyr Leu Glu Glu Pro Asp Ser Ser Gly
    195                 200                 205

His Ser Tyr Gly Pro Val Ser Ser Glu Val Ile Lys Ala Leu Gln Arg
210                 215                 220

Val Asp Gly Met Val Gly Met Leu Met Asp Gly Leu Lys Glu Leu Asn
225                 230                 235                 240

Leu His Arg Cys Leu Asn Leu Ile Leu Ile Ser Asp His Gly Met Glu
                245                 250                 255

Gln Gly Ser Cys Lys Lys Tyr Ile Tyr Leu Asn Lys Tyr Leu Gly Asp
            260                 265                 270

Val Lys Asn Ile Lys Val Ile Tyr Gly Pro Ala Ala Arg Leu Arg Pro
    275                 280                 285

Ser Asp Val Pro Asp Lys Tyr Tyr Ser Phe Asn Tyr Glu Gly Ile Ala
290                 295                 300

Arg Asn Leu Ser Cys Arg Glu Pro Asn Gln His Phe Lys Pro Tyr Leu
305                 310                 315                 320

Lys His Phe Leu Pro Lys Arg Leu His Phe Ala Lys Ser Asp Arg Ile
                325                 330                 335
```

```
Glu Pro Leu Thr Phe Tyr Leu Asp Pro Gln Trp Gln Leu Ala Leu Asn
                340                 345                 350

Pro Ser Glu Arg Lys Tyr Cys Gly Ser Gly Phe His Gly Ser Asp Asn
            355                 360                 365

Val Phe Ser Asn Met Gln Ala Leu Phe Val Gly Tyr Gly Pro Gly Phe
        370                 375                 380

Lys His Gly Ile Glu Ala Asp Thr Phe Glu Asn Ile Glu Val Tyr Asn
385                 390                 395                 400

Leu Met Cys Asp Leu Leu Asn Leu Thr Pro Ala Pro Asn Asn Gly Thr
                405                 410                 415

His Gly Ser Leu Asn His Leu Leu Lys Asn Pro Val Tyr Thr Pro Lys
            420                 425                 430

His Pro Lys Glu Val His Pro Leu Val Gln Cys Pro Phe Thr Arg Asn
            435                 440                 445

Pro Arg Asp Asn Leu Gly Cys Ser Cys Asn Pro Ser Ile Leu Pro Ile
        450                 455                 460

Glu Asp Phe Gln Thr Gln Phe Asn Leu Thr Val Ala Glu Glu Lys Ile
465                 470                 475                 480

Ile Lys His Glu Thr Leu Pro Tyr Gly Arg Pro Arg Val Leu Gln Lys
            485                 490                 495

Glu Asn Thr Ile Cys Leu Leu Ser Gln His Gln Phe Met Ser Gly Tyr
            500                 505                 510

Ser Gln Asp Ile Leu Met Pro Leu Trp Thr Ser Tyr Thr Val Asp Arg
            515                 520                 525

Asn Asp Ser Phe Ser Thr Glu Asp Phe Ser Asn Cys Leu Tyr Gln Asp
        530                 535                 540

Phe Arg Ile Pro Leu Ser Pro Val His Lys Cys Ser Phe Tyr Lys Asn
545                 550                 555                 560

Asn Thr Lys Val Ser Tyr Gly Phe Leu Ser Pro Gln Leu Asn Lys
            565                 570                 575

Asn Ser Ser Gly Ile Tyr Ser Glu Ala Leu Leu Thr Thr Asn Ile Val
            580                 585                 590

Pro Met Tyr Gln Ser Phe Gln Val Ile Trp Arg Tyr Phe His Asp Thr
            595                 600                 605

Leu Leu Arg Lys Tyr Ala Glu Glu Arg Asn Gly Val Asn Val Val Ser
        610                 615                 620

Gly Pro Val Phe Asp Phe Asp Tyr Asp Gly Arg Cys Asp Ser Leu Glu
625                 630                 635                 640

Asn Leu Arg Gln Lys Arg Arg Val Ile Arg Asn Gln Glu Ile Leu Ile
            645                 650                 655

Pro Thr His Phe Phe Ile Val Leu Thr Ser Cys Lys Asp Thr Ser Gln
            660                 665                 670

Thr Pro Leu His Cys Glu Asn Leu Asp Thr Leu Ala Phe Ile Leu Pro
        675                 680                 685

His Arg Thr Asp Asn Ser Glu Ser Cys Val His Gly Lys His Asp Ser
            690                 695                 700

Ser Trp Val Glu Glu Leu Leu Met Leu His Arg Ala Arg Ile Thr Asp
705                 710                 715                 720

Val Glu His Ile Thr Gly Leu Ser Phe Tyr Gln Gln Arg Lys Glu Pro
            725                 730                 735

Val Ser Asp Ile Leu Lys Leu Lys Thr His Leu Pro Thr Phe Ser Gln
            740                 745                 750

Glu Asp
```

<210> SEQ ID NO 7
<211> LENGTH: 2238
<212> TYPE: DNA
<213> ORGANISM: Artificial Sequence
<220> FEATURE:
<223> OTHER INFORMATION: Synthetic

<400> SEQUENCE: 7

| | | | | | |
|---|---|---|---|---|---|
| atgggtgtac | tgctcacaca | gaggacgctg | ctcagtctgg | tccttgcact | cctgtttcca    60 |
| agcatggcga | gcatggcagg | gtttgaaacg | cctcctacac | tcttgttttc | tttggatgga   120 |
| ttcagggcag | aatatttgca | cacttggggt | ggacttcttc | ctgttattag | caaactcaaa   180 |
| aaatgtggaa | catatactaa | aaacatgaga | ccggtgtatc | caacaaaaac | tttccccaat   240 |
| cactacagca | ttgtcaccgg | attgtatcca | gaatctcatg | gcataatcga | caataagatg   300 |
| tatgatccca | aaatgaatgc | ttccttttca | cttaaaagta | agagaaaatt | taatccggag   360 |
| tggtacaaag | agaaccaat  | ttgggtcaca | gctaagtatc | aaggcctcaa | gtctggcaca   420 |
| ttttctggc  | caggatcaga | tgtggaaatt | aacggaattt | tcccagacat | ctataaaatg   480 |
| tataatggtt | cagtgccatt | tgaagaaagg | attttggctg | ttcttcagtg | gctgcagctt   540 |
| ccaaaagatg | aaagaccaca | cttttacact | ttgtatttgg | aagaaccaga | ttcttcaggt   600 |
| cattcatatg | gaccagtcag | cagtgaagtc | atcaaagcct | tgcagagggt | tgatggtatg   660 |
| gttggtatgc | tgatggatgg | tctgaaagag | ctgaacttgc | acagatgcct | gaacctcatc   720 |
| cttatttcag | atcatggcat | ggaacaaggc | agttgtaaga | atacatata  | tctgaataag   780 |
| tatttggggg | atgttaaaaa | tattaaagtt | atctatggac | ctgcagctcg | attgagaccc   840 |
| tctgatgtcc | cagataaata | ctattcattt | aactatgaag | gcattgcccg | aaatcttttct  900 |
| tgccgggaac | caaccagca  | cttcaaacct | tatctgaaac | atttcttgcc | taagcgtttg   960 |
| cactttgcta | gagtgatag  | aattgagccc | ttgacattct | atttggaccc | tcagtggcaa  1020 |
| cttgcattga | atccctcaga | aaggaaatat | tgtggaagtg | gatttcatgg | ctctgacaat  1080 |
| gtgttttcaa | atatgcaagc | cctctttgtt | ggctatggac | ctggattcaa | gcatggcatt  1140 |
| gaggctgaca | cctttgaaaa | cattgaagtc | tataacttga | tgtgtgattt | gctgaatttg  1200 |
| acaccggctc | ctaataacgg | aactcatgga | agtcttaacc | accttctgaa | gaatcctgtt  1260 |
| tatacgccaa | agcatcccaa | agaagtgcac | cccctggtgc | agtgcccctt | cacaagaaac  1320 |
| cccagagata | accttggctg | ctcatgtaac | ccttccattt | tgccgattga | ggattttcaa  1380 |
| acacagttca | atctgaccgt | ggcagaagag | aagattatta | gcatgaaaac | tttgcccctat 1440 |
| ggaagaccta | gagttctcca | gaaggaaaac | accatctgtc | ttctttccca | gcaccagttt  1500 |
| atgagtggat | acagccaaga | catcttgatg | cccctttgga | catcctatac | cgtggacaga  1560 |
| aatgacagtt | tctctacgga | agacttctcc | aactgtctgt | accaggactt | agaattcct   1620 |
| cttagtcctg | tccataaatg | ttcatttat  | aaaaataaca | ccaaagtgag | ttacgggttc  1680 |
| ctctcccccac | cacaactgaa | taagaattca | agtggaatat | attctgaagc | cttgcttact  1740 |
| acaaatatag | tgccaatgta | ccagagtttt | caagttatat | ggcgctactt | tcatgacacc  1800 |
| ctcttgcgaa | agtatgcaga | agaaagaaat | ggtgtcaatg | tcgtcagtgg | tcctgtgttt  1860 |
| gactttgatt | atgatggacg | ttgtgattcc | ttggagaatt | tgaggcaaaa | aagaagagtc  1920 |
| atccgtaacc | aagaaatttt | gattccaact | catttcttca | ttgtgctgac | aagctgtaaa  1980 |
| gatacatctc | agacgccttt | gcactgtgaa | aacctggaca | ccttggcttt | cattttgcct  2040 |

-continued

```
cacaggactg ataacagcga gagctgtgtg catgggaagc atgactcctc atgggttgaa    2100
gaattgttga tgttgcacag agcacggatc acagacgtcg agcacatcac tggactcagc    2160
ttttatcaac aaagaaaaga gccagtttca gacattttga agttgaaaac acatttgcca    2220
acctttagcc aagaagat                                                  2238
```

<210> SEQ ID NO 8
<211> LENGTH: 746
<212> TYPE: PRT
<213> ORGANISM: Artificial sequence
<220> FEATURE:
<223> OTHER INFORMATION: Synthetic

<400> SEQUENCE: 8

```
Ile Gly Val Leu Leu Thr Gln Arg Thr Leu Leu Ser Leu Val Leu Ala
1               5                   10                  15

Leu Leu Phe Pro Ser Met Ala Ser Met Ala Gly Phe Glu Thr Pro Pro
            20                  25                  30

Thr Leu Leu Phe Ser Leu Asp Gly Phe Arg Ala Glu Tyr Leu His Thr
        35                  40                  45

Trp Gly Gly Leu Leu Pro Val Ile Ser Lys Leu Lys Lys Cys Gly Thr
50                  55                  60

Tyr Thr Lys Asn Met Arg Pro Val Tyr Pro Thr Lys Thr Phe Pro Asn
65                  70                  75                  80

His Tyr Ser Ile Val Thr Gly Leu Tyr Pro Glu Ser His Gly Ile Ile
                85                  90                  95

Asp Asn Lys Met Tyr Asp Pro Lys Met Asn Ala Ser Phe Ser Leu Lys
            100                 105                 110

Ser Lys Glu Lys Phe Asn Pro Glu Trp Tyr Lys Gly Glu Pro Ile Trp
        115                 120                 125

Val Thr Ala Lys Tyr Gln Gly Leu Lys Ser Gly Thr Phe Phe Trp Pro
130                 135                 140

Gly Ser Asp Val Glu Ile Asn Gly Ile Phe Pro Asp Ile Tyr Lys Met
145                 150                 155                 160

Tyr Asn Gly Ser Val Pro Phe Glu Glu Arg Ile Leu Ala Val Leu Gln
                165                 170                 175

Trp Leu Gln Leu Pro Lys Asp Glu Arg Pro His Phe Tyr Thr Leu Tyr
            180                 185                 190

Leu Glu Glu Pro Asp Ser Ser Gly His Ser Tyr Gly Pro Val Ser Ser
        195                 200                 205

Glu Val Ile Lys Ala Leu Gln Arg Val Asp Gly Met Val Gly Met Leu
210                 215                 220

Met Asp Gly Leu Lys Glu Leu Asn Leu His Arg Cys Leu Asn Leu Ile
225                 230                 235                 240

Leu Ile Ser Asp His Gly Met Glu Gln Gly Ser Cys Lys Lys Tyr Ile
                245                 250                 255

Tyr Leu Asn Lys Tyr Leu Gly Asp Val Lys Asn Ile Lys Val Ile Tyr
            260                 265                 270

Gly Pro Ala Ala Arg Leu Arg Pro Ser Asp Val Pro Asp Lys Tyr Tyr
        275                 280                 285

Ser Phe Asn Tyr Glu Gly Ile Ala Arg Asn Leu Ser Cys Arg Glu Pro
        290                 295                 300

Asn Gln His Phe Lys Pro Tyr Leu Lys His Phe Leu Pro Lys Arg Leu
305                 310                 315                 320

His Phe Ala Lys Ser Asp Arg Ile Glu Pro Leu Thr Phe Tyr Leu Asp
```

```
            325                 330                 335
Pro Gln Trp Gln Leu Ala Leu Asn Pro Ser Glu Arg Lys Tyr Cys Gly
            340                 345                 350
Ser Gly Phe His Gly Ser Asp Asn Val Phe Ser Asn Met Gln Ala Leu
            355                 360                 365
Phe Val Gly Tyr Gly Pro Phe Lys His Gly Ile Glu Ala Asp Thr
    370                 375                 380
Phe Glu Asn Ile Glu Val Tyr Asn Leu Met Cys Asp Leu Leu Asn Leu
385                 390                 395                 400
Thr Pro Ala Pro Asn Asn Gly Thr His Gly Ser Leu Asn His Leu Leu
                405                 410                 415
Lys Asn Pro Val Tyr Thr Pro Lys His Pro Lys Glu Val His Pro Leu
            420                 425                 430
Val Gln Cys Pro Phe Thr Arg Asn Pro Arg Asp Asn Leu Gly Cys Ser
            435                 440                 445
Cys Asn Pro Ser Ile Leu Pro Ile Glu Asp Phe Gln Thr Gln Phe Asn
450                 455                 460
Leu Thr Val Ala Glu Glu Lys Ile Ile Lys His Glu Thr Leu Pro Tyr
465                 470                 475                 480
Gly Arg Pro Arg Val Leu Gln Lys Glu Asn Thr Ile Cys Leu Leu Ser
            485                 490                 495
Gln His Gln Phe Met Ser Gly Tyr Ser Gln Asp Ile Leu Met Pro Leu
                500                 505                 510
Trp Thr Ser Tyr Thr Val Asp Arg Asn Asp Ser Phe Ser Thr Glu Asp
            515                 520                 525
Phe Ser Asn Cys Leu Tyr Gln Asp Phe Arg Ile Pro Leu Ser Pro Val
            530                 535                 540
His Lys Cys Ser Phe Tyr Lys Asn Asn Thr Lys Val Ser Tyr Gly Phe
545                 550                 555                 560
Leu Ser Pro Pro Gln Leu Asn Lys Asn Ser Ser Gly Ile Tyr Ser Glu
                565                 570                 575
Ala Leu Leu Thr Thr Asn Ile Val Pro Met Tyr Gln Ser Phe Gln Val
                580                 585                 590
Ile Trp Arg Tyr Phe His Asp Thr Leu Leu Arg Lys Tyr Ala Glu Glu
            595                 600                 605
Arg Asn Gly Val Asn Val Val Ser Gly Pro Val Phe Asp Phe Asp Tyr
            610                 615                 620
Asp Gly Arg Cys Asp Ser Leu Glu Asn Leu Arg Gln Lys Arg Arg Val
625                 630                 635                 640
Ile Arg Asn Gln Glu Ile Leu Ile Pro Thr His Phe Ile Val Leu
                645                 650                 655
Thr Ser Cys Lys Asp Thr Ser Gln Thr Pro Leu His Cys Glu Asn Leu
                660                 665                 670
Asp Thr Leu Ala Phe Ile Leu Pro His Arg Thr Asp Asn Ser Glu Ser
            675                 680                 685
Cys Val His Gly Lys His Asp Ser Ser Trp Val Glu Glu Leu Leu Met
            690                 695                 700
Leu His Arg Ala Arg Ile Thr Asp Val Glu His Ile Thr Gly Leu Ser
705                 710                 715                 720
Phe Tyr Gln Gln Arg Lys Glu Pro Val Ser Asp Ile Leu Lys Leu Lys
                725                 730                 735
Thr His Leu Pro Thr Phe Ser Gln Glu Asp
                740                 745
```

<210> SEQ ID NO 9
<211> LENGTH: 2556
<212> TYPE: DNA
<213> ORGANISM: Artificial sequence
<220> FEATURE:
<223> OTHER INFORMATION: Synthetic

<400> SEQUENCE: 9

| | | | | | |
|---|---|---|---|---|---|
| atgggtgtac | tgctcacaca | gaggacgctg | ctcagtctgg | tccttgcact | cctgtttcca | 60 |
| agcatggcga | gcatgccaag | ttgtgccaaa | gaagttaaaa | gttgcaaagg | tcgctgtttc | 120 |
| gagagaacat | ttgggaactg | tcgctgtgat | gctgcctgtg | ttgagcttgg | aaactgctgt | 180 |
| ttggattacc | aggagacgtg | catagaacca | gaacatatat | ggacttgcaa | caaattcagg | 240 |
| tgtggtgaga | aaagattgac | cagaagcctc | tgtgcctgtt | cagatgattg | caaggacaag | 300 |
| ggcgactgct | gcatcaacta | cagttcagtg | tgtcaaggtg | agaaagttg | ggtggaagaa | 360 |
| ccatgtgaga | gcattaatga | gccacagtgc | cagcagggt | ttgaaacgcc | tcctacactc | 420 |
| ttgttttctt | tggatggatt | cagggcagaa | tatttgcaca | cttggggtgg | acttcttcct | 480 |
| gttattagca | aactcaaaaa | atgtggaaca | tatactaaaa | acatgagacc | ggtgtatcca | 540 |
| acaaaaactt | tccccaatca | ctacagcatt | gtcaccggat | tgtatccaga | atctcatggc | 600 |
| ataatcgaca | ataagatgta | tgatcccaaa | atgaatgctt | cctttcact | taaaagtaaa | 660 |
| gagaaattta | atccggagtg | gtacaaagga | gaaccaattt | gggtcacagc | taagtatcaa | 720 |
| ggcctcaagt | ctggcacatt | tttctggcca | ggatcagatg | tggaaattaa | cggaattttc | 780 |
| ccagacatct | ataaaatgta | taatggttca | gtgccatttg | aagaaaggat | tttggctgtt | 840 |
| cttcagtggc | tgcagcttcc | aaaagatgaa | agaccacact | tttacacttt | gtatttggaa | 900 |
| gaaccagatt | cttcaggtca | ttcatatgga | ccagtcagca | gtgaagtcat | caaagccttg | 960 |
| cagagggttg | atggtatggt | tggtatgctg | atggatggtc | tgaaagagct | gaacttgcac | 1020 |
| agatgcctga | acctcatcct | tatttcagat | catggcatgg | aacaaggcag | ttgtaagaaa | 1080 |
| tacatatatc | tgaataagta | tttgggggat | gttaaaaata | ttaaagttat | ctatggacct | 1140 |
| gcagctcgat | tgagacccc | tgatgtccca | gataaatact | attcatttaa | ctatgaaggc | 1200 |
| attgcccgaa | atctttcttg | ccgggaacca | aaccagcact | tcaaacctta | tctgaaacat | 1260 |
| ttcttgccta | agcgtttgca | ctttgctaag | agtgatagaa | ttgagccctt | gacattctat | 1320 |
| ttggaccctc | agtggcaact | tgcattgaat | ccctcagaaa | ggaaatattg | tggaagtgga | 1380 |
| tttcatggct | ctgacaatgt | gttttcaaat | atgcaagccc | tctttgttgg | ctatggacct | 1440 |
| ggattcaagc | atggcattga | ggctgacacc | tttgaaaaca | ttgaagtcta | taacttgatg | 1500 |
| tgtgatttgc | tgaatttgac | accggctcct | aataacggaa | ctcatggaag | tcttaaccac | 1560 |
| cttctgaaga | atcctgttta | tacgccaaag | catcccaaag | aagtgcaccc | cctggtgcag | 1620 |
| tgccccttca | caagaaaccc | cagagataac | cttggctgct | catgtaaccc | ttccatttg | 1680 |
| ccgattgagg | attttcaaac | acagttcaat | ctgaccgtgg | cagaagagaa | gattattaag | 1740 |
| catgaaactt | tgcccctatgg | aagacctaga | gttctccaga | aggaaaacac | catctgtctt | 1800 |
| ctttcccagc | accagtttat | gagtggatac | agccaagaca | tcttgatgcc | ctttggaca | 1860 |
| tcctataccg | tggacagaaa | tgacagtttc | tctacggaag | acttctccaa | ctgtctgtac | 1920 |
| caggacttta | gaattcctct | tagtcctgtc | cataaatgtt | cattttataa | aataacacc | 1980 |
| aaagtgagtt | acgggttcct | ctccccacca | caactgaata | agaattcaag | tggaatatat | 2040 |

```
tctgaagcct tgcttactac aaatatagtg ccaatgtacc agagttttca agttatatgg    2100
cgctactttc atgacaccct cttgcgaaag tatgcagaag aaagaaatgg tgtcaatgtc    2160
gtcagtggtc ctgtgtttga ctttgattat gatggacgtt gtgattcctt ggagaatttg    2220
aggcaaaaaa gaagagtcat ccgtaaccaa gaaattttga ttccaactca tttcttcatt    2280
gtgctgacaa gctgtaaaga tacatctcag acgcctttgc actgtgaaaa cctggacacc    2340
ttggctttca ttttgcctca caggactgat aacagcgaga gctgtgtgca tgggaagcat    2400
gactcctcat gggttgaaga attgttgatg ttgcacagag cacggatcac agacgtcgag    2460
cacatcactg gactcagctt ttatcaacaa agaaaagagc cagtttcaga cattttgaag    2520
ttgaaaacac atttgccaac ctttagccaa gaagat                              2556
```

<210> SEQ ID NO 10
<211> LENGTH: 852
<212> TYPE: PRT
<213> ORGANISM: Artificial seqeunce
<220> FEATURE:
<223> OTHER INFORMATION: Synthetic

<400> SEQUENCE: 10

```
Ile Gly Val Leu Leu Thr Gln Arg Thr Leu Leu Ser Leu Val Leu Ala
1               5                   10                  15

Leu Leu Phe Pro Ser Met Ala Ser Met Pro Ser Cys Ala Lys Glu Val
            20                  25                  30

Lys Ser Cys Lys Gly Arg Cys Phe Glu Arg Thr Phe Gly Asn Cys Arg
        35                  40                  45

Cys Asp Ala Ala Cys Val Glu Leu Gly Asn Cys Cys Leu Asp Tyr Gln
    50                  55                  60

Glu Thr Cys Ile Glu Pro Glu His Ile Trp Thr Cys Asn Lys Phe Arg
65                  70                  75                  80

Cys Gly Glu Lys Arg Leu Thr Arg Ser Leu Cys Ala Cys Ser Asp Asp
                85                  90                  95

Cys Lys Asp Lys Gly Asp Cys Cys Ile Asn Tyr Ser Ser Val Cys Gln
            100                 105                 110

Gly Glu Lys Ser Trp Val Glu Glu Pro Cys Glu Ser Ile Asn Glu Pro
        115                 120                 125

Gln Cys Pro Ala Gly Phe Glu Thr Pro Pro Thr Leu Leu Phe Ser Leu
    130                 135                 140

Asp Gly Phe Arg Ala Glu Tyr Leu His Thr Trp Gly Gly Leu Leu Pro
145                 150                 155                 160

Val Ile Ser Lys Leu Lys Lys Cys Gly Thr Tyr Thr Lys Asn Met Arg
                165                 170                 175

Pro Val Tyr Pro Thr Lys Thr Phe Pro Asn His Tyr Ser Ile Val Thr
            180                 185                 190

Gly Leu Tyr Pro Glu Ser His Gly Ile Ile Asp Asn Lys Met Tyr Asp
        195                 200                 205

Pro Lys Met Asn Ala Ser Phe Ser Leu Lys Ser Lys Glu Lys Phe Asn
    210                 215                 220

Pro Glu Trp Tyr Lys Gly Glu Pro Ile Trp Val Thr Ala Lys Tyr Gln
225                 230                 235                 240

Gly Leu Lys Ser Gly Thr Phe Phe Trp Pro Gly Ser Asp Val Glu Ile
                245                 250                 255

Asn Gly Ile Phe Pro Asp Ile Tyr Lys Met Tyr Asn Gly Ser Val Pro
            260                 265                 270
```

-continued

```
Phe Glu Glu Arg Ile Leu Ala Val Leu Gln Trp Leu Gln Leu Pro Lys
            275                 280                 285

Asp Glu Arg Pro His Phe Tyr Thr Leu Tyr Leu Glu Glu Pro Asp Ser
        290                 295                 300

Ser Gly His Ser Tyr Gly Pro Val Ser Ser Glu Val Ile Lys Ala Leu
305                 310                 315                 320

Gln Arg Val Asp Gly Met Val Gly Met Leu Met Asp Gly Leu Lys Glu
                325                 330                 335

Leu Asn Leu His Arg Cys Leu Asn Leu Ile Leu Ile Ser Asp His Gly
            340                 345                 350

Met Glu Gln Gly Ser Cys Lys Lys Tyr Ile Tyr Leu Asn Lys Tyr Leu
        355                 360                 365

Gly Asp Val Lys Asn Ile Lys Val Ile Tyr Gly Pro Ala Ala Arg Leu
370                 375                 380

Arg Pro Ser Asp Val Pro Asp Lys Tyr Tyr Ser Phe Asn Tyr Glu Gly
385                 390                 395                 400

Ile Ala Arg Asn Leu Ser Cys Arg Glu Pro Asn Gln His Phe Lys Pro
                405                 410                 415

Tyr Leu Lys His Phe Leu Pro Lys Arg Leu His Phe Ala Lys Ser Asp
            420                 425                 430

Arg Ile Glu Pro Leu Thr Phe Tyr Leu Asp Pro Gln Trp Gln Leu Ala
        435                 440                 445

Leu Asn Pro Ser Glu Arg Lys Tyr Cys Gly Ser Gly Phe His Gly Ser
    450                 455                 460

Asp Asn Val Phe Ser Asn Met Gln Ala Leu Phe Val Gly Tyr Gly Pro
465                 470                 475                 480

Gly Phe Lys His Gly Ile Glu Ala Asp Thr Phe Glu Asn Ile Glu Val
                485                 490                 495

Tyr Asn Leu Met Cys Asp Leu Leu Asn Leu Thr Pro Ala Pro Asn Asn
            500                 505                 510

Gly Thr His Gly Ser Leu Asn His Leu Leu Lys Asn Pro Val Tyr Thr
        515                 520                 525

Pro Lys His Pro Lys Glu Val His Pro Leu Val Gln Cys Pro Phe Thr
    530                 535                 540

Arg Asn Pro Arg Asp Asn Leu Gly Cys Ser Cys Asn Pro Ser Ile Leu
545                 550                 555                 560

Pro Ile Glu Asp Phe Gln Thr Gln Phe Asn Leu Thr Val Ala Glu Glu
                565                 570                 575

Lys Ile Ile Lys His Glu Thr Leu Pro Tyr Gly Arg Pro Arg Val Leu
            580                 585                 590

Gln Lys Glu Asn Thr Ile Cys Leu Leu Ser Gln His Gln Phe Met Ser
        595                 600                 605

Gly Tyr Ser Gln Asp Ile Leu Met Pro Leu Trp Thr Ser Tyr Thr Val
    610                 615                 620

Asp Arg Asn Asp Ser Phe Ser Thr Glu Asp Phe Ser Asn Cys Leu Tyr
625                 630                 635                 640

Gln Asp Phe Arg Ile Pro Leu Ser Pro Val His Lys Cys Ser Phe Tyr
                645                 650                 655

Lys Asn Asn Thr Lys Val Ser Tyr Gly Phe Leu Ser Pro Pro Gln Leu
            660                 665                 670

Asn Lys Asn Ser Ser Gly Ile Tyr Ser Glu Ala Leu Leu Thr Thr Asn
        675                 680                 685

Ile Val Pro Met Tyr Gln Ser Phe Gln Val Ile Trp Arg Tyr Phe His
```

```
                       690                 695                 700
Asp Thr Leu Leu Arg Lys Tyr Ala Glu Glu Arg Asn Gly Val Asn Val
705                 710                 715                 720

Val Ser Gly Pro Val Phe Asp Phe Asp Tyr Asp Gly Arg Cys Asp Ser
                725                 730                 735

Leu Glu Asn Leu Arg Gln Lys Arg Arg Val Ile Arg Asn Gln Glu Ile
                740                 745                 750

Leu Ile Pro Thr His Phe Phe Ile Val Leu Thr Ser Cys Lys Asp Thr
            755                 760                 765

Ser Gln Thr Pro Leu His Cys Glu Asn Leu Asp Thr Leu Ala Phe Ile
        770                 775                 780

Leu Pro His Arg Thr Asp Asn Ser Glu Ser Cys Val His Gly Lys His
785                 790                 795                 800

Asp Ser Ser Trp Val Glu Glu Leu Leu Met Leu His Arg Ala Arg Ile
                805                 810                 815

Thr Asp Val Glu His Ile Thr Gly Leu Ser Phe Tyr Gln Gln Arg Lys
                820                 825                 830

Glu Pro Val Ser Asp Ile Leu Lys Leu Lys Thr His Leu Pro Thr Phe
            835                 840                 845

Ser Gln Glu Asp
    850
```

```
<210> SEQ ID NO 11
<211> LENGTH: 2580
<212> TYPE: DNA
<213> ORGANISM: Artificial sequence
<220> FEATURE:
<223> OTHER INFORMATION: Synthetic

<400> SEQUENCE: 11
atgggtgtac tgctcacaca gaggacgctg ctcagtctgg tccttgcact cctgtttcca      60
agcatggcga gcatggatga cgatgatgac gacgatgacc caagttgtgc caaagaagtt     120
aaaagttgca aggtcgctg tttcgagaga acatttggga actgtcgctg tgatgctgcc     180
tgtgttgagc ttggaaactg ctgtttggat taccaggaga cgtgcataga accagaacat     240
atatggactt gcaacaaatt caggtgtggt gagaaaagat tgaccagaag cctctgtgcc     300
tgttcagatg attgcaagga caagggcgac tgctgcatca actacagttc agtgtgtcaa     360
ggtgagaaaa gttgggtgga agaaccatgt gagagcatta atgagccaca gtgcccagca     420
gggtttgaaa cgcctcctac actcttgttt tctttggatg gattcagggc agaatatttg     480
cacacttggg gtgacttct tcctgttatt agcaaactca aaaatgtgg aacatatact      540
aaaaacatga ccgggtgta ccaacaaaa actttcccca atcactacag cattgtcacc      600
ggattgtatc cagaatctca tggcataatc gacaataaga tgtatgatcc caaaatgaat     660
gcttcctttt cacttaaaag taagagaaa tttaatccgg agtggtacaa aggagaacca     720
atttgggtca cagctaagta tcaaggcctc aagtctggca ttttttctg gccaggatca     780
gatgtggaaa ttaacggaat tttcccagac atctataaaa tgtataatgg ttcagtgcca     840
tttgaagaaa ggattttggc tgttcttcag tggctgcagc ttccaaaaga tgaaagacca     900
cactttttaca ctttgtattt ggaagaacca gattcttcag gtcattcata tggaccagtc     960
agcagtgaag tcatcaaagc cttgcagagg gttgatggta tggttggtat gctgatggat    1020
ggtctgaaaa agctgaactt gcacagatgc ctgaacctca tccttattc agatcatggc    1080
atggaacaag gcagttgtaa gaaatacata tatctgaata agtatttggg ggatgttaaa    1140
```

```
aatattaaag ttatctatgg acctgcagct cgattgagac cctctgatgt cccagataaa    1200
tactattcat ttaactatga aggcattgcc cgaaatcttt cttgccggga accaaaccag    1260
cacttcaaac cttatctgaa acatttcttg cctaagcgtt tgcactttgc taagagtgat    1320
agaattgagc ccttgacatt ctatttggac cctcagtggc aacttgcatt gaatccctca    1380
gaaaggaaat attgtggaag tggatttcat ggctctgaca atgtgttttc aaatatgcaa    1440
gccctctttg ttggctatgg acctggattc aagcatggca ttgaggctga cacctttgaa    1500
aacattgaag tctataactt gatgtgtgat ttgctgaatt tgacaccggc tcctaataac    1560
ggaactcatg gaagtcttaa ccaccttctg aagaatcctg tttatacgcc aaagcatccc    1620
aaagaagtgc accccctggt gcagtgcccc ttcacaagaa ccccagaga taaccttggc    1680 tgctcatgta acccttccat tttgccgatt gaggattttc aaacacagtt caatctgacc    1740
gtggcagaag agaagattat taagcatgaa actttgccct atggaagacc tagagttctc    1800
cagaaggaaa acaccatctg tcttctttcc cagcaccagt ttatgagtgg atacagccaa    1860
gacatcttga tgccccttg gacatcctat accgtggaca gaaatgacag tttctctacg    1920
gaagacttct ccaactgtct gtaccaggac tttagaattc ctcttagtcc tgtccataaa    1980
tgttcatttt ataaaaataa caccaaagtg agttacgggt tcctctcccc accacaactg    2040
aataagaatt caagtggaat atattctgaa gccttgctta ctacaaatat agtgccaatg    2100
taccagagtt ttcaagttat atggcgctac tttcatgaca ccctcttgcg aaagtatgca    2160
gaagaaagaa atggtgtcaa tgtcgtcagt ggtcctgtgt ttgactttga ttatgatgga    2220
cgttgtgatt ccttggagaa tttgaggcaa aaaagaagag tcatccgtaa ccaagaaatt    2280
ttgattccaa ctcatttctt cattgtgctg acaagctgta aagatacatc tcagacgcct    2340
ttgcactgtg aaaacctgga caccttggct ttcattttgc ctcacaggac tgataacagc    2400
gagagctgtg tgcatgggaa gcatgactcc tcatgggttg aagaattgtt gatgttgcac    2460
agagcacgga tcacagacgt cgagcacatc actggactca gctttttatca acaaagaaaa    2520 gagccagttt cagacatttt gaagttgaaa acacatttgc caacctttag ccaagaagat    2580
```

<210> SEQ ID NO 12
<211> LENGTH: 860
<212> TYPE: PRT
<213> ORGANISM: Artificial sequence
<220> FEATURE:
<223> OTHER INFORMATION: Synthetic

<400> SEQUENCE: 12

```
Ile Gly Val Leu Leu Thr Gln Arg Thr Leu Leu Ser Leu Val Leu Ala
1               5                  10                  15

Leu Leu Phe Pro Ser Met Ala Ser Met Asp Asp Asp Asp Asp Asp
            20                  25                  30

Asp Pro Ser Cys Ala Lys Glu Val Lys Ser Cys Lys Gly Arg Cys Phe
        35                  40                  45

Glu Arg Thr Phe Gly Asn Cys Arg Cys Asp Ala Ala Cys Val Glu Leu
    50                  55                  60

Gly Asn Cys Cys Leu Asp Tyr Gln Glu Thr Cys Ile Glu Pro Glu His
65                  70                  75                  80

Ile Trp Thr Cys Asn Lys Phe Arg Cys Gly Glu Lys Arg Leu Thr Arg
                85                  90                  95

Ser Leu Cys Ala Cys Ser Asp Asp Cys Lys Asp Lys Gly Asp Cys Cys
            100                 105                 110
```

-continued

```
Ile Asn Tyr Ser Ser Val Cys Gln Gly Glu Lys Ser Trp Val Glu
            115                 120                 125
Pro Cys Glu Ser Ile Asn Glu Pro Gln Cys Pro Ala Gly Phe Glu Thr
130                 135                 140
Pro Pro Thr Leu Leu Phe Ser Leu Asp Gly Phe Arg Ala Glu Tyr Leu
145                 150                 155                 160
His Thr Trp Gly Gly Leu Leu Pro Val Ile Ser Lys Leu Lys Cys
            165                 170                 175
Gly Thr Tyr Thr Lys Asn Met Arg Pro Val Tyr Pro Thr Lys Thr Phe
            180                 185                 190
Pro Asn His Tyr Ser Ile Val Thr Gly Leu Tyr Pro Glu Ser His Gly
            195                 200                 205
Ile Ile Asp Asn Lys Met Tyr Asp Pro Lys Met Asn Ala Ser Phe Ser
210                 215                 220
Leu Lys Ser Lys Glu Lys Phe Asn Pro Glu Trp Tyr Lys Gly Glu Pro
225                 230                 235                 240
Ile Trp Val Thr Ala Lys Tyr Gln Gly Leu Lys Ser Gly Thr Phe Phe
            245                 250                 255
Trp Pro Gly Ser Asp Val Glu Ile Asn Gly Ile Phe Pro Asp Ile Tyr
            260                 265                 270
Lys Met Tyr Asn Gly Ser Val Pro Phe Glu Glu Arg Ile Leu Ala Val
            275                 280                 285
Leu Gln Trp Leu Gln Leu Pro Lys Asp Glu Arg Pro His Phe Tyr Thr
            290                 295                 300
Leu Tyr Leu Glu Glu Pro Asp Ser Ser Gly His Ser Tyr Gly Pro Val
305                 310                 315                 320
Ser Ser Glu Val Ile Lys Ala Leu Gln Arg Val Asp Gly Met Val Gly
            325                 330                 335
Met Leu Met Asp Gly Leu Lys Glu Leu Asn Leu His Arg Cys Leu Asn
            340                 345                 350
Leu Ile Leu Ile Ser Asp His Gly Met Glu Gln Gly Ser Cys Lys Lys
            355                 360                 365
Tyr Ile Tyr Leu Asn Lys Tyr Leu Gly Asp Val Lys Asn Ile Lys Val
            370                 375                 380
Ile Tyr Gly Pro Ala Ala Arg Leu Arg Pro Ser Asp Val Pro Asp Lys
385                 390                 395                 400
Tyr Tyr Ser Phe Asn Tyr Glu Gly Ile Ala Arg Asn Leu Ser Cys Arg
            405                 410                 415
Glu Pro Asn Gln His Phe Lys Pro Tyr Leu Lys His Phe Leu Pro Lys
            420                 425                 430
Arg Leu His Phe Ala Lys Ser Asp Arg Ile Glu Pro Leu Thr Phe Tyr
            435                 440                 445
Leu Asp Pro Gln Trp Gln Leu Ala Leu Asn Pro Ser Glu Arg Lys Tyr
450                 455                 460
Cys Gly Ser Gly Phe His Gly Ser Asp Asn Val Phe Ser Asn Met Gln
465                 470                 475                 480
Ala Leu Phe Val Gly Tyr Gly Pro Gly Phe Lys His Gly Ile Glu Ala
            485                 490                 495
Asp Thr Phe Glu Asn Ile Glu Val Tyr Asn Leu Met Cys Asp Leu Leu
            500                 505                 510
Asn Leu Thr Pro Ala Pro Asn Asn Gly Thr His Gly Ser Leu Asn His
            515                 520                 525
```

Leu Leu Lys Asn Pro Val Tyr Thr Pro Lys His Pro Lys Glu Val His
    530                 535                 540

Pro Leu Val Gln Cys Pro Phe Thr Arg Asn Pro Arg Asp Asn Leu Gly
545                 550                 555                 560

Cys Ser Cys Asn Pro Ser Ile Leu Pro Ile Glu Asp Phe Gln Thr Gln
                565                 570                 575

Phe Asn Leu Thr Val Ala Glu Glu Lys Ile Ile Lys His Glu Thr Leu
            580                 585                 590

Pro Tyr Gly Arg Pro Arg Val Leu Gln Lys Glu Asn Thr Ile Cys Leu
        595                 600                 605

Leu Ser Gln His Gln Phe Met Ser Gly Tyr Ser Gln Asp Ile Leu Met
    610                 615                 620

Pro Leu Trp Thr Ser Tyr Thr Val Asp Arg Asn Asp Ser Phe Ser Thr
625                 630                 635                 640

Glu Asp Phe Ser Asn Cys Leu Tyr Gln Asp Phe Arg Ile Pro Leu Ser
                645                 650                 655

Pro Val His Lys Cys Ser Phe Tyr Lys Asn Asn Thr Lys Val Ser Tyr
            660                 665                 670

Gly Phe Leu Ser Pro Pro Gln Leu Asn Lys Asn Ser Ser Gly Ile Tyr
        675                 680                 685

Ser Glu Ala Leu Leu Thr Thr Asn Ile Val Pro Met Tyr Gln Ser Phe
    690                 695                 700

Gln Val Ile Trp Arg Tyr Phe His Asp Thr Leu Leu Arg Lys Tyr Ala
705                 710                 715                 720

Glu Glu Arg Asn Gly Val Asn Val Val Ser Gly Pro Val Phe Asp Phe
                725                 730                 735

Asp Tyr Asp Gly Arg Cys Asp Ser Leu Glu Asn Leu Arg Gln Lys Arg
            740                 745                 750

Arg Val Ile Arg Asn Gln Glu Ile Leu Ile Pro Thr His Phe Phe Ile
        755                 760                 765

Val Leu Thr Ser Cys Lys Asp Thr Ser Gln Thr Pro Leu His Cys Glu
    770                 775                 780

Asn Leu Asp Thr Leu Ala Phe Ile Leu Pro His Arg Thr Asp Asn Ser
785                 790                 795                 800

Glu Ser Cys Val His Gly Lys His Asp Ser Ser Trp Val Glu Glu Leu
                805                 810                 815

Leu Met Leu His Arg Ala Arg Ile Thr Asp Val Glu His Ile Thr Gly
            820                 825                 830

Leu Ser Phe Tyr Gln Gln Arg Lys Glu Pro Val Ser Asp Ile Leu Lys
        835                 840                 845

Leu Lys Thr His Leu Pro Thr Phe Ser Gln Glu Asp
    850                 855                 860

<210> SEQ ID NO 13
<211> LENGTH: 2580
<212> TYPE: DNA
<213> ORGANISM: Artificial sequence
<220> FEATURE:
<223> OTHER INFORMATION: Synthetic

<400> SEQUENCE: 13
gtgggtgtac tgctcacaca gaggacgctg ctcagtctgg tccttgcact cctgtttcca      60
agcatggcga gcatgccaag ttgtgccaaa gaagttaaaa gttgcaaagg tcgctgtttc     120
gagagaacat ttgggaactg tcgctgtgat gctgcctgtg ttgagcttgg aaactgctgt     180

-continued

```
ttggattacc aggagacgtg catagaacca gaacatatat ggacttgcaa caaattcagg    240
tgtggtgaga aaagattgac cagaagcctc tgtgcctgtt cagatgattg caaggacaag    300
ggcgactgct gcatcaacta cagttcagtg tgtcaaggtg agaaaagttg ggtggaagaa    360
ccatgtgaga gcattaatga gccacagtgc ccagcagggt ttgaaacgcc tcctacactc    420
ttgttttctt tggatggatt cagggcagaa tatttgcaca cttggggtgg acttcttcct    480
gttattagca aactcaaaaa atgtggaaca tatactaaaa acatgagacc ggtgtatcca    540
acaaaaactt tccccaatca ctacagcatt gtcaccggat tgtatccaga atctcatggc    600
ataatcgaca ataagatgta tgatcccaaa atgaatgctt cctttttcact taaaagtaaa    660 gagaaattta atccggagtg gtacaaagga gaaccaattt gggtcacagc taagtatcaa    720
ggcctcaagt ctggcacatt tttctggcca ggatcagatg tggaaattaa cggaattttc    780
ccagacatct ataaaatgta taatggttca gtgccatttg aagaaggat tttggctgtt    840 cttcagtggc tgcagcttcc aaaagatgaa agaccacact tttacacttt gtatttggaa    900
gaaccagatt cttcaggtca ttcatatgga ccagtcagca gtgaagtcat caaagccttg    960
cagagggttg atggtatggt tggtatgctg atggatggtc tgaaagagct gaacttgcac   1020
agatgcctga acctcatcct tatttcagat catggcatgg aacaaggcag ttgtaagaaa   1080
tacatatatc tgaataagta tttgggggat gttaaaaata ttaaagttat ctatggacct   1140
gcagctcgat tgagaccctc tgatgtccca gataaatact attcatttaa ctatgaaggc   1200
attgcccgaa atctttcttg ccgggaacca aaccagcact caaaccctta tctgaaacat   1260
ttcttgccta agcgtttgca ctttgctaag agtgatagaa ttgagccctt gacattctat   1320
ttggaccctc agtggcaact tgcattgaat ccctcagaaa ggaaatattg tggaagtgga   1380
tttcatggct ctgacaatgt gttttcaaat atgcaagccc tctttgttgg ctatggacct   1440
ggattcaagc atggcattga ggctgacacc tttgaaaaca ttgaagtcta taacttgatg   1500
tgtgatttgc tgaatttgac accggctcct aataacggaa ctcatggaag tcttaaccac   1560
cttctgaaga atcctgttta tacgccaaag catcccaaag aagtgcaccc cctggtgcag   1620
tgccccttca caagaaaccc cagagataac cttggctgct catgtaaccc ttccattttg   1680
ccgattgagg attttcaaac acagttcaat ctgaccgtgg cagaagagaa gattattaag   1740
catgaaactt tgccctatgg aagacctaga gttctccaga aggaaaacac catctgtctt   1800 cttttcccagc accagtttat gagtggatac agccaagaca tcttgatgcc ccttttggaca  1860 tcctataccg tggacagaaa tgacagtttc tctacgaaag acttctccaa ctgtctgtac   1920
caggacttta gaattcctct tagtcctgtc cataaatgtt cattttataa aataacacc    1980 aaagtgagtt acgggttcct ctccccacca caactgaata agaattcaag tggaatatat   2040
tctgaagcct tgcttactac aaatatagtg ccaatgtacc agagttttca agttatatgg   2100
cgctactttc atgacaccct cttgcgaaag tatgcagaag aaagaaatgg tgtcaatgtc   2160
gtcagtggtc ctgtgtttga ctttgattat gatggacgtt gtgattcctt ggagaatttg   2220
aggcaaaaaa gaagagtcat ccgtaaccaa gaaattttga ttccaactca tttcttcatt   2280
gtgctgacaa gctgtaaaga tacatctcag acgcctttgc actgtgaaaa cctgacacac   2340
ttggctttca ttttgcctca caggactgat aacagcgaga gctgtgtgca tgggaagcat   2400
gactcctcat gggttgaaga attgttgatg ttgcacagag cacgatcac agacgtcgag    2460 cacatcactg gactcagctt ttatcaacaa agaaaagagc cagttcaga cattttgaag   2520 ttgaaaacac atttgccaac ctttagccaa gaagatgatg acgatgatga cgacgattga   2580
```

<210> SEQ ID NO 14
<211> LENGTH: 859
<212> TYPE: PRT
<213> ORGANISM: Artificial sequence
<220> FEATURE:
<223> OTHER INFORMATION: Synthetic

<400> SEQUENCE: 14

```
Gln Gly Val Leu Leu Thr Gln Arg Thr Leu Leu Ser Leu Val Leu Ala
1               5                   10                  15

Leu Leu Phe Pro Ser Met Ala Ser Met Pro Ser Cys Ala Lys Glu Val
            20                  25                  30

Lys Ser Cys Lys Gly Arg Cys Phe Glu Arg Thr Phe Gly Asn Cys Arg
        35                  40                  45

Cys Asp Ala Ala Cys Val Glu Leu Gly Asn Cys Cys Leu Asp Tyr Gln
    50                  55                  60

Glu Thr Cys Ile Glu Pro Glu His Ile Trp Thr Cys Asn Lys Phe Arg
65                  70                  75                  80

Cys Gly Glu Lys Arg Leu Thr Arg Ser Leu Cys Ala Cys Ser Asp Asp
                85                  90                  95

Cys Lys Asp Lys Gly Asp Cys Cys Ile Asn Tyr Ser Ser Val Cys Gln
            100                 105                 110

Gly Glu Lys Ser Trp Val Glu Pro Cys Glu Ser Ile Asn Glu Pro
        115                 120                 125

Gln Cys Pro Ala Gly Phe Glu Thr Pro Pro Thr Leu Leu Phe Ser Leu
    130                 135                 140

Asp Gly Phe Arg Ala Glu Tyr Leu His Thr Trp Gly Gly Leu Leu Pro
145                 150                 155                 160

Val Ile Ser Lys Leu Lys Lys Cys Gly Thr Tyr Thr Lys Asn Met Arg
                165                 170                 175

Pro Val Tyr Pro Thr Lys Thr Phe Pro Asn His Tyr Ser Ile Val Thr
            180                 185                 190

Gly Leu Tyr Pro Glu Ser His Gly Ile Ile Asp Asn Lys Met Tyr Asp
        195                 200                 205

Pro Lys Met Asn Ala Ser Phe Ser Leu Lys Ser Lys Glu Lys Phe Asn
    210                 215                 220

Pro Glu Trp Tyr Lys Gly Glu Pro Ile Trp Val Thr Ala Lys Tyr Gln
225                 230                 235                 240

Gly Leu Lys Ser Gly Thr Phe Phe Trp Pro Gly Ser Asp Val Glu Ile
                245                 250                 255

Asn Gly Ile Phe Pro Asp Ile Tyr Lys Met Tyr Asn Gly Ser Val Pro
            260                 265                 270

Phe Glu Glu Arg Ile Leu Ala Val Leu Gln Trp Leu Gln Leu Pro Lys
        275                 280                 285

Asp Glu Arg Pro His Phe Tyr Thr Leu Tyr Leu Glu Glu Pro Asp Ser
    290                 295                 300

Ser Gly His Ser Tyr Gly Pro Val Ser Ser Glu Val Ile Lys Ala Leu
305                 310                 315                 320

Gln Arg Val Asp Gly Met Val Gly Met Leu Met Asp Gly Leu Lys Glu
                325                 330                 335

Leu Asn Leu His Arg Cys Leu Asn Leu Ile Leu Ile Ser Asp His Gly
            340                 345                 350

Met Glu Gln Gly Ser Cys Lys Lys Tyr Ile Tyr Leu Asn Lys Tyr Leu
        355                 360                 365
```

```
Gly Asp Val Lys Asn Ile Lys Val Ile Tyr Gly Pro Ala Ala Arg Leu
    370                 375                 380

Arg Pro Ser Asp Val Pro Asp Lys Tyr Tyr Ser Phe Asn Tyr Glu Gly
385                 390                 395                 400

Ile Ala Arg Asn Leu Ser Cys Arg Glu Pro Asn Gln His Phe Lys Pro
                405                 410                 415

Tyr Leu Lys His Phe Leu Pro Lys Arg Leu His Phe Ala Lys Ser Asp
            420                 425                 430

Arg Ile Glu Pro Leu Thr Phe Tyr Leu Asp Pro Gln Trp Gln Leu Ala
        435                 440                 445

Leu Asn Pro Ser Glu Arg Lys Tyr Cys Gly Ser Gly Phe His Gly Ser
450                 455                 460

Asp Asn Val Phe Ser Asn Met Gln Ala Leu Phe Val Gly Tyr Gly Pro
465                 470                 475                 480

Gly Phe Lys His Gly Ile Glu Ala Asp Thr Phe Glu Asn Ile Glu Val
                485                 490                 495

Tyr Asn Leu Met Cys Asp Leu Leu Asn Leu Thr Pro Ala Pro Asn Asn
            500                 505                 510

Gly Thr His Gly Ser Leu Asn His Leu Leu Lys Asn Pro Val Tyr Thr
        515                 520                 525

Pro Lys His Pro Lys Glu Val His Pro Leu Val Gln Cys Pro Phe Thr
    530                 535                 540

Arg Asn Pro Arg Asp Asn Leu Gly Cys Ser Cys Asn Pro Ser Ile Leu
545                 550                 555                 560

Pro Ile Glu Asp Phe Gln Thr Gln Phe Asn Leu Thr Val Ala Glu Glu
                565                 570                 575

Lys Ile Ile Lys His Glu Thr Leu Pro Tyr Gly Arg Pro Arg Val Leu
            580                 585                 590

Gln Lys Glu Asn Thr Ile Cys Leu Leu Ser Gln His Gln Phe Met Ser
        595                 600                 605

Gly Tyr Ser Gln Asp Ile Leu Met Pro Leu Trp Thr Ser Tyr Thr Val
    610                 615                 620

Asp Arg Asn Asp Ser Phe Ser Thr Glu Asp Phe Ser Asn Cys Leu Tyr
625                 630                 635                 640

Gln Asp Phe Arg Ile Pro Leu Ser Pro Val His Lys Cys Ser Phe Tyr
                645                 650                 655

Lys Asn Asn Thr Lys Val Ser Tyr Gly Phe Leu Ser Pro Pro Gln Leu
            660                 665                 670

Asn Lys Asn Ser Ser Gly Ile Tyr Ser Glu Ala Leu Leu Thr Thr Asn
        675                 680                 685

Ile Val Pro Met Tyr Gln Ser Phe Gln Val Ile Trp Arg Tyr Phe His
    690                 695                 700

Asp Thr Leu Leu Arg Lys Tyr Ala Glu Glu Arg Asn Gly Val Asn Val
705                 710                 715                 720

Val Ser Gly Pro Val Phe Asp Phe Asp Tyr Asp Gly Arg Cys Asp Ser
                725                 730                 735

Leu Glu Asn Leu Arg Gln Lys Arg Arg Val Ile Arg Asn Gln Glu Ile
            740                 745                 750

Leu Ile Pro Thr His Phe Phe Ile Val Leu Thr Ser Cys Lys Asp Thr
        755                 760                 765

Ser Gln Thr Pro Leu His Cys Glu Asn Leu Asp Thr Leu Ala Phe Ile
    770                 775                 780
```

```
Leu Pro His Arg Thr Asp Asn Ser Glu Ser Cys Val His Gly Lys His
785                 790                 795                 800

Asp Ser Ser Trp Val Glu Glu Leu Leu Met Leu His Arg Ala Arg Ile
            805                 810                 815

Thr Asp Val Glu His Ile Thr Gly Leu Ser Phe Tyr Gln Gln Arg Lys
        820                 825                 830

Glu Pro Val Ser Asp Ile Leu Lys Leu Lys Thr His Leu Pro Thr Phe
    835                 840                 845

Ser Gln Glu Asp Asp Asp Asp Asp Asp
    850                 855
```

<210> SEQ ID NO 15
<211> LENGTH: 10
<212> TYPE: PRT
<213> ORGANISM: Artificial sequence
<220> FEATURE:
<223> OTHER INFORMATION: Synthetic

<400> SEQUENCE: 15

```
Gly Gly Gly Gly Ser Gly Gly Gly Gly Ser
1               5                   10
```

<210> SEQ ID NO 16
<211> LENGTH: 232
<212> TYPE: PRT
<213> ORGANISM: Artificial sequence
<220> FEATURE:
<223> OTHER INFORMATION: Synthetic

<400> SEQUENCE: 16

```
Glu Pro Lys Ser Cys Asp Lys Thr His Thr Cys Pro Pro Cys Pro Ala
1               5                   10                  15

Pro Glu Ala Ala Gly Ala Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

```
Ser Leu Ser Leu Ser Pro Gly Lys
225                 230
```

<210> SEQ ID NO 17
<211> LENGTH: 662
<212> TYPE: PRT
<213> ORGANISM: Artificial sequence
<220> FEATURE:
<223> OTHER INFORMATION: Synthetic

<400> SEQUENCE: 17

```
Ile Gly Val Leu Leu Thr Gln Arg Thr Leu Leu Ser Leu Val Leu Ala
1               5                   10                  15

Leu Leu Phe Pro Ser Met Ala Ser Met Glu Pro Lys Ser Cys Asp Lys
            20                  25                  30

Thr His Thr Cys Pro Pro Cys Pro Ala Pro Glu Ala Ala Gly Ala Pro
        35                  40                  45

Ser Val Phe Leu Phe Pro Pro Lys Pro Lys Asp Thr Leu Met Ile Ser
    50                  55                  60

Arg Thr Pro Glu Val Thr Cys Val Val Val Asp Val Ser His Glu Asp
65                  70                  75                  80

Pro Glu Val Lys Phe Asn Trp Tyr Val Asp Gly Val Glu Val His Asn
                85                  90                  95

Ala Lys Thr Lys Pro Arg Glu Glu Gln Tyr Asn Ser Thr Tyr Arg Val
            100                 105                 110

Val Ser Val Leu Thr Val Leu His Gln Asp Trp Leu Asn Gly Lys Glu
        115                 120                 125

Tyr Lys Cys Lys Val Ser Asn Lys Ala Leu Pro Ala Pro Ile Glu Lys
    130                 135                 140

Thr Ile Ser Lys Ala Lys Gly Gln Pro Arg Glu Pro Gln Val Tyr Thr
145                 150                 155                 160

Leu Pro Pro Ser Arg Glu Glu Met Thr Lys Asn Gln Val Ser Leu Thr
                165                 170                 175

Cys Leu Val Lys Gly Phe Tyr Pro Ser Asp Ile Ala Val Glu Trp Glu
            180                 185                 190

Ser Asn Gly Gln Pro Glu Asn Asn Tyr Lys Thr Thr Pro Pro Val Leu
        195                 200                 205

Asp Ser Asp Gly Ser Phe Phe Leu Tyr Ser Lys Leu Thr Val Asp Lys
    210                 215                 220

Ser Arg Trp Gln Gln Gly Asn Val Phe Ser Cys Ser Val Met His Glu
225                 230                 235                 240

Ala Leu His Asn His Tyr Thr Gln Lys Ser Leu Ser Leu Ser Pro Gly
                245                 250                 255

Lys Asp Asp Asp Asp Asp Asp Asp Gly Gly Gly Gly Ser Gly Gly
            260                 265                 270

Gly Gly Ser Ala Gly Phe Glu Thr Pro Pro Thr Leu Leu Phe Ser Leu
        275                 280                 285

Asp Gly Phe Arg Ala Glu Tyr Leu His Thr Trp Gly Gly Leu Leu Pro
    290                 295                 300

Val Ile Ser Lys Leu Lys Lys Cys Gly Thr Tyr Thr Lys Asn Met Arg
305                 310                 315                 320

Pro Val Tyr Pro Thr Lys Thr Phe Pro Asn His Tyr Ser Ile Val Thr
                325                 330                 335

Gly Leu Tyr Pro Glu Ser His Gly Ile Ile Asp Asn Lys Met Tyr Asp
            340                 345                 350
```

```
Pro Lys Met Asn Ala Ser Phe Ser Leu Lys Ser Lys Glu Lys Phe Asn
            355                 360                 365

Pro Glu Trp Tyr Lys Gly Glu Pro Ile Trp Val Thr Ala Lys Tyr Gln
370                 375                 380

Gly Leu Lys Ser Gly Thr Phe Phe Trp Pro Gly Ser Asp Val Glu Ile
385                 390                 395                 400

Asn Gly Ile Phe Pro Asp Ile Tyr Lys Met Tyr Asn Gly Ser Val Pro
                405                 410                 415

Phe Glu Glu Arg Ile Leu Ala Val Leu Gln Trp Leu Gln Leu Pro Lys
                420                 425                 430

Asp Glu Arg Pro His Phe Tyr Thr Leu Tyr Leu Glu Pro Asp Ser
                435                 440                 445

Ser Gly His Ser Tyr Gly Pro Val Ser Ser Glu Val Ile Lys Ala Leu
            450                 455                 460

Gln Arg Val Asp Gly Met Val Gly Met Leu Met Asp Gly Leu Lys Glu
465                 470                 475                 480

Leu Asn Leu His Arg Cys Leu Asn Leu Ile Leu Ser Asp His Gly
                485                 490                 495

Met Glu Gln Gly Ser Cys Lys Lys Tyr Ile Tyr Leu Asn Lys Tyr Leu
            500                 505                 510

Gly Asp Val Lys Asn Ile Lys Val Ile Tyr Gly Pro Ala Ala Arg Leu
            515                 520                 525

Arg Pro Ser Asp Val Pro Asp Lys Tyr Tyr Ser Phe Asn Tyr Glu Gly
            530                 535                 540

Ile Ala Arg Asn Leu Ser Cys Arg Glu Pro Asn Gln His Phe Lys Pro
545                 550                 555                 560

Tyr Leu Lys His Phe Leu Pro Lys Arg Leu His Phe Ala Lys Ser Asp
                565                 570                 575

Arg Ile Glu Pro Leu Thr Phe Tyr Leu Asp Pro Gln Trp Gln Leu Ala
                580                 585                 590

Leu Asn Pro Ser Glu Arg Lys Tyr Cys Gly Ser Gly Phe His Gly Ser
            595                 600                 605

Asp Asn Val Phe Ser Asn Met Gln Ala Leu Phe Val Gly Tyr Gly Pro
            610                 615                 620

Gly Phe Lys His Gly Ile Glu Ala Asp Thr Phe Glu Asn Ile Glu Val
625                 630                 635                 640

Tyr Asn Leu Met Cys Asp Leu Leu Asn Leu Thr Pro Ala Pro Asn Asn
                645                 650                 655

Gly Thr His Gly Ser Leu
            660

<210> SEQ ID NO 18
<211> LENGTH: 662
<212> TYPE: PRT
<213> ORGANISM: Artificial sequence
<220> FEATURE:
<223> OTHER INFORMATION: Synthetic

<400> SEQUENCE: 18

Ile Gly Val Leu Leu Thr Gln Arg Thr Leu Leu Ser Leu Val Leu Ala
1               5                   10                  15

Leu Leu Phe Pro Ser Met Ala Ser Met Glu Pro Lys Ser Cys Asp Lys
                20                  25                  30

Thr His Thr Cys Pro Pro Cys Pro Ala Pro Glu Ala Ala Gly Ala Pro
            35                  40                  45
```

-continued

```
Ser Val Phe Leu Phe Pro Pro Lys Pro Lys Asp Thr Leu Met Ile Ser
     50                  55                  60
Arg Thr Pro Glu Val Thr Cys Val Val Val Asp Val Ser His Glu Asp
 65                  70                  75                  80
Pro Glu Val Lys Phe Asn Trp Tyr Val Asp Gly Val Glu Val His Asn
                 85                  90                  95
Ala Lys Thr Lys Pro Arg Glu Glu Gln Tyr Asn Ser Thr Tyr Arg Val
            100                 105                 110
Val Ser Val Leu Thr Val Leu His Gln Asp Trp Leu Asn Gly Lys Glu
            115                 120                 125
Tyr Lys Cys Lys Val Ser Asn Lys Ala Leu Pro Ala Pro Ile Glu Lys
            130                 135                 140
Thr Ile Ser Lys Ala Lys Gly Gln Pro Arg Glu Pro Gln Val Tyr Thr
145                 150                 155                 160
Leu Pro Pro Ser Arg Glu Glu Met Thr Lys Asn Gln Val Ser Leu Thr
                165                 170                 175
Cys Leu Val Lys Gly Phe Tyr Pro Ser Asp Ile Ala Val Glu Trp Glu
                180                 185                 190
Ser Asn Gly Gln Pro Glu Asn Asn Tyr Lys Thr Thr Pro Pro Val Leu
            195                 200                 205
Asp Ser Asp Gly Ser Phe Phe Leu Tyr Ser Lys Leu Thr Val Asp Lys
210                 215                 220
Ser Arg Trp Gln Gln Gly Asn Val Phe Ser Cys Ser Val Met His Glu
225                 230                 235                 240
Ala Leu His Asn His Tyr Thr Gln Lys Ser Leu Ser Leu Ser Pro Gly
                245                 250                 255
Lys Ala Gly Phe Glu Thr Pro Thr Leu Leu Phe Ser Leu Asp Gly
            260                 265                 270
Phe Arg Ala Glu Tyr Leu His Thr Trp Gly Gly Leu Leu Pro Val Ile
            275                 280                 285
Ser Lys Leu Lys Lys Cys Gly Thr Tyr Thr Lys Asn Met Arg Pro Val
            290                 295                 300
Tyr Pro Thr Lys Thr Phe Pro Asn His Tyr Ser Ile Val Thr Gly Leu
305                 310                 315                 320
Tyr Pro Glu Ser His Gly Ile Ile Asp Asn Lys Met Tyr Asp Pro Lys
                325                 330                 335
Met Asn Ala Ser Phe Ser Leu Lys Ser Lys Glu Lys Phe Asn Pro Glu
            340                 345                 350
Trp Tyr Lys Gly Glu Pro Ile Trp Val Thr Ala Lys Tyr Gln Gly Leu
            355                 360                 365
Lys Ser Gly Thr Phe Phe Trp Pro Gly Ser Asp Val Glu Ile Asn Gly
            370                 375                 380
Ile Phe Pro Asp Ile Tyr Lys Met Tyr Asn Gly Ser Val Pro Phe Glu
385                 390                 395                 400
Glu Arg Ile Leu Ala Val Leu Gln Trp Leu Gln Leu Pro Lys Asp Glu
                405                 410                 415
Arg Pro His Phe Tyr Thr Leu Tyr Leu Glu Glu Pro Asp Ser Ser Gly
            420                 425                 430
His Ser Tyr Gly Pro Val Ser Ser Glu Val Ile Lys Ala Leu Gln Arg
            435                 440                 445
Val Asp Gly Met Val Gly Met Leu Met Asp Gly Leu Lys Glu Leu Asn
            450                 455                 460
```

-continued

```
Leu His Arg Cys Leu Asn Leu Ile Leu Ile Ser Asp His Gly Met Glu
465                 470                 475                 480

Gln Gly Ser Cys Lys Lys Tyr Ile Tyr Leu Asn Lys Tyr Leu Gly Asp
                485                 490                 495

Val Lys Asn Ile Lys Val Ile Tyr Gly Pro Ala Ala Arg Leu Arg Pro
            500                 505                 510

Ser Asp Val Pro Asp Lys Tyr Tyr Ser Phe Asn Tyr Glu Gly Ile Ala
        515                 520                 525

Arg Asn Leu Ser Cys Arg Glu Pro Asn Gln His Phe Lys Pro Tyr Leu
    530                 535                 540

Lys His Phe Leu Pro Lys Arg Leu His Phe Ala Lys Ser Asp Arg Ile
545                 550                 555                 560

Glu Pro Leu Thr Phe Tyr Leu Asp Pro Gln Trp Gln Leu Ala Leu Asn
                565                 570                 575

Pro Ser Glu Arg Lys Tyr Cys Gly Ser Gly Phe His Gly Ser Asp Asn
            580                 585                 590

Val Phe Ser Asn Met Gln Ala Leu Phe Val Gly Tyr Gly Pro Gly Phe
        595                 600                 605

Lys His Gly Ile Glu Ala Asp Thr Phe Glu Asn Ile Glu Val Tyr Asn
    610                 615                 620

Leu Met Cys Asp Leu Leu Asn Leu Thr Pro Ala Pro Asn Asn Gly Thr
625                 630                 635                 640

His Gly Ser Leu Gly Gly Gly Gly Ser Gly Gly Gly Gly Ser Asp Asp
                645                 650                 655

Asp Asp Asp Asp Asp Asp
            660
```